(12) United States Patent
Gorin et al.

(10) Patent No.: US 7,863,415 B2
(45) Date of Patent: Jan. 4, 2011

(54) AMINO ACID AND PEPTIDE CONJUGATES OF AMILORIDE AND METHODS OF USE THEREOF

(75) Inventors: Fredric A. Gorin, Davis, CA (US); Michael H. Nantz, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 90 days.

(21) Appl. No.: 11/040,831

(22) Filed: Jan. 21, 2005

(65) Prior Publication Data

US 2006/0160746 A1 Jul. 20, 2006

Related U.S. Application Data

(60) Provisional application No. 60/538,972, filed on Jan. 23, 2004.

(51) Int. Cl.
*A61K 38/04* (2006.01)
*A61K 38/00* (2006.01)

(52) U.S. Cl. ..................................... 530/329
(58) Field of Classification Search .................. None
See application file for complete search history.

(56) References Cited

PUBLICATIONS

Pato, et al, "Synthesis of macromolecular conjugates of a urokinase inhibitor: amiloride," Journal of Bioactive and compatible Polymers, (1999), vol. 14(2), 99-121.*
Thornber, "Isosterism and Molecular Modification in Drug Design," Chem Soc. Rev. (1979), vol. 8(4), pp. 563-580.*
Tompa P., et al, "On the sequential determinants of calpain cleavage," J Biol Chem. May 14, 2004;279(20):20775-85.*
Bischof, G. et al., "Effect of extracellular pH on intracellular pH-regulation and growth in a human colon carcinoma cell-line," *Biochimia et Biophysics Acta*, 1996, vol. 1282, pp. 131-139.
Boyer, M.J. et al., "Regulation of Intracellular pH in Tumor Cell Lines: Influence of Microenvironmental Conditions," *Cancer Research*, Aug. 15, 1992, vol. 52, pp. 4441-4447.
Chen, E.I. et al., "A Unique Substrate Recognition Profile for Matrix Metallproteinase-2," *The Journal of Biological Chemistry*, Feb. 8, 2002, vol. 277, No. 6, pp. 4485-4491.
Cohen, G.M., "Caspases: the executioners of apoptosis," *Biochem. J.*, 1997, vol. 326, pp. 1-16.
Cragoe, E.J., JR. et al., "Pyrazine Diuretics. II. N-Amidino-3-amino-5-substituted 6-Halopyrazinecarboxamides," *J. Med. Chem.*, Jan. 1967, vol. 10, pp. 66-75.
Denault, J-B. et al., "Capases: Keys in the Ignition of Cell Death," *Chemical Reviews*, 2002, vol. 102, No. 12, pp. 4489-4499.
Dobson, G.P. et al., "Phosphofructokinase control in muscle: nature and reversal of pH-dependent ATP inhibition," *Am. J. Physiol.*, 1986, vol. 250, pp. R71-R76.
Frelin, C. et al., "Amiloride and its analogs as tools to inhibit $Na^+$ transport via the $Na^+$ channel, the $Na^+/H^+$ antiport and the $Na+/Ca^{2+}$ exchanger," *Biochimie*, 1988, vol. 70, pp. 1285-1290.

García-Cañero, R. et al., "$Na^+$:$H^+$ exchange inhibition induces intracellular acidosis and differentially impairs cell growth and viability of human and rat hepatocarcinoma cells," *Toxicology Letters*, 1999, vol. 106, pp. 215-228.
Gennaro, A.R. et al. (eds.), *Remington's Pharmaceutical Sciences, 17th Edition*, 1985, Mack Publishing Co.: Easton, PA, Table of Contents only, 7 pages.
Ghosh, A.K. et al., "Solid-Phase Synthesis of N-Acyl-N-Alkyl/Aryl Disubstituted Guanidines," *J. Org. Chem.*, 2001, vol. 66, No. 6, pp. 2161-2164.
Gorin, F.A. et al., "Novel Analogues of Enkephalin: Identification of Functional Groups Required for Biological Activity," *Journal of Medicinal Chemsitry*, 1980, vol. 23, No. 10, pp. 1113-1122.
Gorin. F. et al., "Perinecrotic glioma proliferation and metabolic profile within an intracerebral tumor xenograft," *Acta Neuropathol*, 2004, vol. 107, pp. 235-244.
Gumina, R.J. et al., "Inhibition of the $Na^+/H^+$ Exchanger Confers Greater Cardioprotection Against 90 Minutes of Myocardial Ischemia Than Ischemic Preconditioning in Dogs," *Circulation*, 1999, vol. 100, pp. 2519-2526.
Hasuda, K. et al., "Antitumor Activity of Nigericin and 5-(N-ehtyl-N-isopropyl)amiloride: An Approach to Therapy Based on Cellular Acidification and the Inhibition of Regulation of Intracellular pH," *Oncology Research*, 1994, vol. 6, No. 6, pp. 259-268.
Hegde, M. et al., "Amiloride Kills Malignant Giloma Cells Independent of Its Inhibition of the Sodium-Hydrogen Exchanger," *The Journal of Pharmacology and Experimental Therapeutics*, 2004, vol. 310, No. 1, pp. 67-74.
Henkel, B. et al., "Investigation on Solid-Phase Peptide Synthesis in N-to-C Direction (inverse Synthesis)," *Liebigs Ann. Recueil*, 1997, pp. 2161-2168.
Horvat, B. et al., "Tumour Cell Proliferation is Abolished by Inhibitors of $Na^+/H^+$ and $HCO^-_3/Cl^-$Exchange," *Eur. J. Cancer*, 1993, vol. 29A, No. 1, pp. 132-137.
Klein, H.H. et al., "Myocardial Protection by $Na^{30}$-$H^+$ Exchange Inhibition is Ischemic, Reperfused Porcine Hearts," *Circulation*, Aug. 15, 1995, vol. 92, No. 4, pp. 912-917.
Lah, T.T. et al., "Clinical and experimental studies of cysteine cathepsins and their inhibitors in human brain tumors," *The International Journal of Biological Markers*, 2000, vol. 15, , No. 1, pp. 90-93.

(Continued)

*Primary Examiner* — Cecilia Tsang
*Assistant Examiner* — Thomas S Heard
(74) *Attorney, Agent, or Firm* — Townsend and Townsend and Crew LLP

(57) ABSTRACT

The present invention provides compositions comprising amiloride amino acid and peptide conjugates. Efficient methods are also provided for administering the amiloride conjugates of the present invention for treating cancer or a central nervous system disease or disorder or for preventing or reducing ischemia-reperfusion injury. Further, kits are provided for the treatment of a central nervous system disease or disorder or for the prevention or reduction of ischemia-reperfusion injury using the amiloride conjugates of the present invention.

3 Claims, 11 Drawing Sheets

OTHER PUBLICATIONS

L'Allemain, G. et al., "Blockage of the $Na^{30}/H^+$ Antiport Abolishes Growth Factor-induced DNA Synthesis in Fibroblasts," *The Journal of Biological Chemistry*, Apr. 10, 1984, vol. 259, No. 7, pp. 4313-4319.

Levicăr, N. et al., "Proteases in brain tumour progession," *Acta Neurochir*, 2003, vol. 145, pp. 825-838.

Marshall, G.R., "Peptide Interactions with G-Protein Coupled Receptors," *Biopolymers*, 2001, vol. 60, pp. 246-277.

Masereel, B. et al., "An overview of inhibitors of $Na^{30}/H^+$ exchanger," *European Journal of Medicinal Chemistry*, 2003, vol. 38, pp. 547-554.

Miller, S.M. et al., "Comparison of the Proteolytic Susceptibilites of Homologous L-Amino Acid, D-Amino Acid, and N-Substituted Glycine Peptide and Peptoid Oligomers," *Drug Development Research*, 1995, vol. 25, pp. 20-32.

Molineaus, C.J. et al., "An inhibitor of Endopeptidase-24.15 Blocks the Degradation of Intraventricularly Administered Dynorphins," *Journal of Neurochemistry*, 1990, vol. 55, No. 2, pp. 611-618.

Musgrove, E. et al., "Relationship between Cytoplasmic pH and Proliferation during Exponential Growth and Cellular Quiescence," *Experimental Cell Research.*, 1987, vol. 172, pp. 65-75.

Numata, M. et al., "Molecular Cloning and Characterization of a Novel $(Na^+,K^+)/H^+$ Exchanger Localized to the *trans*-Golgi Network," *The Journal of Biological Chemistry*, May 18, 2001, vol. 276, No. 20, pp. 17387-17394.

Orlowski, J. et al., "$Na^+/H^+$ Exchanges of Mammalian Cells," *The Journal of Biological Chemistry*, Sep. 5, 1997, vol. 272, No. 36, pp. 22373-22376.

Palandoken, H. et al., "Amiloride Peptide Conjugates: Prodrugs for Sodium-Proton Exchange Inhibition," *The Journal of Pharmacology and Experimental Therapeutics*, 2004, vol. 312, No. 3, pp. 961-967.

Piper, H.M. et al., "The role of $Na^+/H^+$ exchange in ischemia-reperfusion," *Basic Res. Cardiol*, 1996, vol. 91, No. 3, pp. 191-202.

Roques, B.P. et al., "Neutral Endopeptidase 24.11: Structure, Inhibition, and Experimental and Clinical Pharmacology," *Pharmacological Reviews*, 1993, vol. 45, No. 1, pp. 87-146.

Sasaki, T. et al., "Comparative Specificity and Kinetic Studies on Porcine Calpain I and Calpain II with Naturally Occurring Peptides and Synthetic Fluorogenic Substrates," *The Journal of Biological Chemistry*, Oct. 25, 1984, vol. 259, No. 20, pp. 12489-12494.

Satoh, J. et al., "Importance of $Ca^{2+}$ influx by $Na^+/Ca^{2+}$ exchange under normal and sodium-loaded conditions in mammalian ventricles," *Molecular and Cellular Biochemistry*, 2003, vol. 242, pp. 11-17.

Scholz, W. et al., "Protective effects of HOE642, a selective sodium-hydrogen exchange subtype 1 inhibitor, on cardiac ischaemia and reperfusion," *Cardiovascular Research*, 1995, vol. 29, pp. 260-268.

Suzuki, Y. et al., "SM-20220, a $Na^+/H^+$ exchanger inhibitor: effects on ischemic brain damage through edema and neutrophil accumulation in a rat middle cerebral artery occlusion model," *Brain Research*, 2002, vol. 945, pp. 242-248.

Szolgay-Daniel, E. et al., "Effects of Amiloride Treatment on U-118 MG Human Glioma and HT-29 Human colon Carcinoma Cells," *Cancer Research*, Feb. 1, 1991, vol. 51, pp. 1039-1044.

Tardif, J-C et al., "Effect of inhibition of the $Na^+/H^+$ exchanger with cariporide on left ventricular function in acute coronary syndromes: Results from the echocardiographic substudy of the GUARDIAN trial," *Can. J. Cardiol.*, Mar. 1, 2004, vol. 20, No. 3, pp. 317-322.

Thornberry, N.A. et al., "A Combinatorial Approach Defines Specificities of Members of the Caspase Family and Granzyme B," *The Journal of Biological Chemistry*, Jul. 18, 1997, vol. 272, No. 29, pp. 17907-17911.

Wong, P. et al., "Cytostatic potential of novel agents that inhibit the regulation of intracellular pH," British Journal of Cancer, 2002, vol. 87, No. 2, pp. 238-245.

* cited by examiner

SEQUENCE LISTING

<160> NUMBER OF SEQ ID NOS: 57

<210> SEQ ID NO 1
<211> LENGTH: 6
<212> TYPE: PRT
<213> ORGANISM: Artificial Sequence
<220> FEATURE:
<223> OTHER INFORMATION: peptide analog of Leu-enkephalin
<220> FEATURE:
<221> NAME/KEY: MOD_RES
<222> LOCATION: (6)..(6)
<223> OTHER INFORMATION: AMIDATION

<400> SEQUENCE: 1

Gly Gly Gly Gly Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: enkephalinase resistant peptide analog of
      Leu-enkephalin
<220> FEATURE:
<221> NAME/KEY: MISC_FEATURE
<222> LOCATION: (2)..(2)
<223> OTHER INFORMATION: Xaa is D-Alanine
<220> FEATURE:
<221> NAME/KEY: MOD_RES
<222> LOCATION: (5)..(5)
<223> OTHER INFORMATION: AMIDATION

<400> SEQUENCE: 2

Tyr Xaa Gly Phe Gly
1               5

<210> SEQ ID NO 3
<211> LENGTH: 9
<212> TYPE: PRT
<213> ORGANISM: Artificial Sequence
<220> FEATURE:
<223> OTHER INFORMATION: peptide selectively cleaved by MMP-2
<220> FEATURE:
<221> NAME/KEY: MOD_RES
<222> LOCATION: (9)..(9)
<223> OTHER INFORMATION: AMIDATION

<400> SEQUENCE: 3

Glu Ser Leu Ala Tyr Tyr Thr Ala Gly
1               5

<210> SEQ ID NO 4
<211> LENGTH: 9
<212> TYPE: PRT
<213> ORGANISM: Artificial Sequence
<220> FEATURE:
<223> OTHER INFORMATION: peptide selectively cleaved by MMP-2
<220> FEATURE:
<221> NAME/KEY: MOD_RES
<222> LOCATION: (9)..(9)
<223> OTHER INFORMATION: AMIDATION

<400> SEQUENCE: 4

Arg Ser Leu Ser Arg Leu Thr Ala Gly
1               5

<210> SEQ ID NO 5

```
<211> LENGTH: 9
<212> TYPE: PRT
<213> ORGANISM: Artificial Sequence
<220> FEATURE:
<223> OTHER INFORMATION: peptide resistant to cleavage by MMP-2
<220> FEATURE:
<221> NAME/KEY: MISC_FEATURE
<222> LOCATION: (4)..(4)
<223> OTHER INFORMATION: Xaa is D-Alanine
<220> FEATURE:
<221> NAME/KEY: MOD_RES
<222> LOCATION: (9)..(9)
<223> OTHER INFORMATION: AMIDATION

<400> SEQUENCE: 5

Glu Ser Leu Xaa Tyr Tyr Thr Ala Gly
1               5

<210> SEQ ID NO 6
<211> LENGTH: 9
<212> TYPE: PRT
<213> ORGANISM: Artificial Sequence
<220> FEATURE:
<223> OTHER INFORMATION: peptide resistant to cleavage by MMP-2
<220> FEATURE:
<221> NAME/KEY: MISC_FEATURE
<222> LOCATION: (6)..(6)
<223> OTHER INFORMATION: Xaa is D-Leucine
<220> FEATURE:
<221> NAME/KEY: MOD_RES
<222> LOCATION: (9)..(9)
<223> OTHER INFORMATION: AMIDATION

<400> SEQUENCE: 6

Arg Ser Leu Ser Arg Xaa Thr Ala Gly
1               5

<210> SEQ ID NO 7
<211> LENGTH: 10
<212> TYPE: PRT
<213> ORGANISM: Artificial Sequence
<220> FEATURE:
<223> OTHER INFORMATION: peptide selectively cleaved by MMP-2
<220> FEATURE:
<221> NAME/KEY: MOD_RES
<222> LOCATION: (10)..(10)
<223> OTHER INFORMATION: AMIDATION

<400> SEQUENCE: 7

Arg Ser Leu Ser Arg Leu Thr Ala Gly Gly
1               5                   10

<210> SEQ ID NO 8
<211> LENGTH: 4
<212> TYPE: PRT
<213> ORGANISM: Artificial Sequence
<220> FEATURE:
<223> OTHER INFORMATION: peptide analog of Leu-enkephalin
<220> FEATURE:
<221> NAME/KEY: MOD_RES
<222> LOCATION: (1)..(1)
<223> OTHER INFORMATION: Attached through an amide linkage to
      3,5-diamino-N-(N-(2-(2-(2-(2-amino-3-(4-hydroxyphenyl)
      propanamido)acetamido)acetamido)acetyl)carbamimidoyl)-6-
      chloropyrazine-2-carboxamide
<220> FEATURE:
<221> NAME/KEY: MOD_RES
<222> LOCATION: (4)..(4)
<223> OTHER INFORMATION: AMIDATION

<400> SEQUENCE: 8

Gly Gly Phe Leu
```

<210> SEQ ID NO 9
<211> LENGTH: 4
<212> TYPE: PRT
<213> ORGANISM: Artificial Sequence
<220> FEATURE:
<223> OTHER INFORMATION: Known peptide substrate of Calpain II
<220> FEATURE:
<221> NAME/KEY: MOD_RES
<222> LOCATION: (1)..(1)
<223> OTHER INFORMATION: SUCCINYLATED at the N-terminus
<220> FEATURE:
<221> NAME/KEY: MOD_RES
<222> LOCATION: (4)..(4)
<223> OTHER INFORMATION: modified at the C-terminus by 7-amino-4-methyl-
      2H-chromen-2-one

<400> SEQUENCE: 9

Leu Leu Val Tyr
1

<210> SEQ ID NO 10
<211> LENGTH: 10
<212> TYPE: PRT
<213> ORGANISM: Artificial Sequence
<220> FEATURE:
<223> OTHER INFORMATION: modified peptide substrate of Calpain II
<220> FEATURE:
<221> NAME/KEY: MOD_RES
<222> LOCATION: (1)..(1)
<223> OTHER INFORMATION: SUCCINYLATED at the N-terminus
<220> FEATURE:
<221> NAME/KEY: MOD_RES
<222> LOCATION: (4)..(10)
<223> OTHER INFORMATION: peptide is modified through a linkage to the C5
      of amiloride
<220> FEATURE:
<221> NAME/KEY: MISC_FEATURE
<222> LOCATION: (5)..(10)
<223> OTHER INFORMATION: Xaa is any amino acid or absent

<400> SEQUENCE: 10

Leu Leu Val Tyr Xaa Xaa Xaa Xaa Xaa Xaa
1               5                   10

<210> SEQ ID NO 11
<211> LENGTH: 16
<212> TYPE: PRT
<213> ORGANISM: Artificial Sequence
<220> FEATURE:
<223> OTHER INFORMATION: modified peptide substrate of Calpain II
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified through a linkage to the C5
      of amiloride

<400> SEQUENCE: 11

Xaa Xaa Xaa Xaa Xaa Xaa Leu Leu Val Tyr Xaa Xaa Xaa Xaa Xaa Xaa
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: modified peptide substrate of Calpain II

```
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (10)..(16)
<223> OTHER INFORMATION: AMIDATION at the C-terminus

<400> SEQUENCE: 12

Xaa Xaa Xaa Xaa Xaa Xaa Leu Leu Val Tyr Xaa Xaa Xaa Xaa Xaa Xaa
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: modified peptide substrate of Calpain II
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified at the C-terminus by a
      methyl group through an ester linkage

<400> SEQUENCE: 13

Xaa Xaa Xaa Xaa Xaa Xaa Leu Leu Val Tyr Xaa Xaa Xaa Xaa Xaa Xaa
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: modified peptide substrate of Calpain II
<220> FEATURE:
<221> NAME/KEY: MOD_RES
<222> LOCATION: (1)..(7)
<223> OTHER INFORMATION: peptide is modified at the through a linkage to
      the C2 of amiloride
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified through a linkage to the C5
      of a second molecule of amiloride

<400> SEQUENCE: 14

Xaa Xaa Xaa Xaa Xaa Xaa Leu Leu Val Tyr Xaa Xaa Xaa Xaa Xaa Xaa
1               5                   10                  15

<210> SEQ ID NO 15
<211> LENGTH: 4
<212> TYPE: PRT
<213> ORGANISM: Artificial Sequence
<220> FEATURE:
```

```
<223> OTHER INFORMATION: known peptide substrate of Caspase 3
<220> FEATURE:
<221> NAME/KEY: MOD_RES
<222> LOCATION: (1)..(1)
<223> OTHER INFORMATION: AMIDATION
<220> FEATURE:
<221> NAME/KEY: MOD_RES
<222> LOCATION: (4)..(4)
<223> OTHER INFORMATION: peptide is modified at the C-terminus by
      4-nitroaniline

<400> SEQUENCE: 15

Asp Glu Val Asp
1

<210> SEQ ID NO 16
<211> LENGTH: 10
<212> TYPE: PRT
<213> ORGANISM: Artificial Sequence
<220> FEATURE:
<223> OTHER INFORMATION: modified peptide substrate of Caspase 3
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(10)
<223> OTHER INFORMATION: peptide is modified through a linkage to the C5
      of amiloride
<220> FEATURE:
<221> NAME/KEY: MISC_FEATURE
<222> LOCATION: (5)..(10)
<223> OTHER INFORMATION: Xaa is any amino acid or absent

<400> SEQUENCE: 16

Asp Glu Val Asp Xaa Xaa Xaa Xaa Xaa Xaa
1               5                   10

<210> SEQ ID NO 17
<211> LENGTH: 16
<212> TYPE: PRT
<213> ORGANISM: Artificial Sequence
<220> FEATURE:
<223> OTHER INFORMATION: modified peptide substrate of Caspase 3
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified through a linkage to the C5
      of amiloride

<400> SEQUENCE: 17

Xaa Xaa Xaa Xaa Xaa Xaa Asp Glu Val Asp Xaa Xaa Xaa Xaa Xaa Xaa
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: modified peptide substrate of Caspase 3
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
```

```
                                of amiloride
<220> FEATURE:
<221> NAME/KEY: MOD_RES
<222> LOCATION: (10)..(16)
<223> OTHER INFORMATION: AMIDATION at the C-terminus

<400> SEQUENCE: 18

Xaa Xaa Xaa Xaa Xaa Xaa Asp Glu Val Asp Xaa Xaa Xaa Xaa Xaa Xaa
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: modified peptide substrate of Caspase 3
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C5
      of amiloride
<220> FEATURE:
<221> NAME/KEY: MOD_RES
<222> LOCATION: (10)..(16)
<223> OTHER INFORMATION: peptide is modified at the C-terminus by a
      methyl group through an ester linkage

<400> SEQUENCE: 19

Xaa Xaa Xaa Xaa Xaa Xaa Asp Glu Val Asp Xaa Xaa Xaa Xaa Xaa Xaa
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: modified peptide substrate of Caspase 3
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified through a linkage to the C5
      of amiloride

<400> SEQUENCE: 20

Xaa Xaa Xaa Xaa Xaa Xaa Asp Glu Val Asp Xaa Xaa Xaa Xaa Xaa Xaa
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: known peptide substrate of Caspase 9
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
```

```
<223> OTHER INFORMATION: peptide is modified at the C-terminus by
      4-nitroaniline

<400> SEQUENCE: 21

Leu Glu His Asp
1

<210> SEQ ID NO 22
<211> LENGTH: 10
<212> TYPE: PRT
<213> ORGANISM: Artificial Sequence
<220> FEATURE:
<223> OTHER INFORMATION: modified peptide substrate of Caspase 9
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(10)
<223> OTHER INFORMATION: peptide is modified through a linkage to the C5
      of amiloride
<220> FEATURE:
<221> NAME/KEY: MISC_FEATURE
<222> LOCATION: (5)..(10)
<223> OTHER INFORMATION: Xaa is any amino acid or absent

<400> SEQUENCE: 22

Leu Glu His Asp Xaa Xaa Xaa Xaa Xaa Xaa
1               5                   10

<210> SEQ ID NO 23
<211> LENGTH: 16
<212> TYPE: PRT
<213> ORGANISM: Artificial Sequence
<220> FEATURE:
<223> OTHER INFORMATION: modified peptide substrate of Caspase 9
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified through a linkage to the C5
      of amiloride

<400> SEQUENCE: 23

Xaa Xaa Xaa Xaa Xaa Xaa Leu Glu His Asp Xaa Xaa Xaa Xaa Xaa Xaa
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: modified peptide substrate of Caspase 9
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (10)..(16)
<223> OTHER INFORMATION: the peptide is modified by AMIDATION at the
      C-terminus

<400> SEQUENCE: 24
```

```
Xaa Xaa Xaa Xaa Xaa Xaa Leu Glu His Asp Xaa Xaa Xaa Xaa Xaa Xaa
1               5                   10                  15
```

<210> SEQ ID NO 25
<211> LENGTH: 16
<212> TYPE: PRT
<213> ORGANISM: Artificial Sequence
<220> FEATURE:
<223> OTHER INFORMATION: modified peptide substrate of Caspase 9
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (10)..(16)
<223> OTHER INFORMATION: peptide is modified at the C-terminus by a
      methyl group through an ester linkage

<400> SEQUENCE: 25

```
Xaa Xaa Xaa Xaa Xaa Xaa Leu Glu His Asp Xaa Xaa Xaa Xaa Xaa Xaa
1               5                   10                  15
```

<210> SEQ ID NO 26
<211> LENGTH: 16
<212> TYPE: PRT
<213> ORGANISM: Artificial Sequence
<220> FEATURE:
<223> OTHER INFORMATION: modified peptide substrate of Caspase 9
<220> FEATURE:
<221> NAME/KEY: MISC_FEATURE
<222> LOCATION: (1)..(16)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (10)..(16)
<223> OTHER INFORMATION: peptide is modified through a linkage to the C5
      of amiloride

<400> SEQUENCE: 26

```
Xaa Xaa Xaa Xaa Xaa Xaa Leu Glu His Asp Xaa Xaa Xaa Xaa Xaa Xaa
1               5                   10                  15
```

<210> SEQ ID NO 27
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (14)..(20)
<223> OTHER INFORMATION: peptide is modified through a linkage to the C5
      of amiloride

<400> SEQUENCE: 27

```
Xaa Xaa Xaa Xaa Xaa Xaa Glu Ser Leu Ala Tyr Tyr Thr Ala Xaa Xaa
1               5                   10                  15
```

```
Xaa Xaa Xaa Xaa
            20

<210> SEQ ID NO 28
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (14)..(20)
<223> OTHER INFORMATION: the peptide is modified by AMIDATION at the
      C-terminus

<400> SEQUENCE: 28

Xaa Xaa Xaa Xaa Xaa Xaa Glu Ser Leu Ala Tyr Tyr Thr Ala Xaa Xaa
1               5                   10                  15

Xaa Xaa Xaa Xaa
            20

<210> SEQ ID NO 29
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (14)..(20)
<223> OTHER INFORMATION: peptide is modified at the C-terminus by a
      methyl group through an ester linkage

<400> SEQUENCE: 29

Xaa Xaa Xaa Xaa Xaa Xaa Glu Ser Leu Ala Tyr Tyr Thr Ala Xaa Xaa
1               5                   10                  15

Xaa Xaa Xaa Xaa
            20

<210> SEQ ID NO 30
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
``` of amiloride
<220> FEATURE:
<221> NAME/KEY: MOD_RES
<222> LOCATION: (14)..(20)
<223> OTHER INFORMATION: peptide is modified through a linkage to the C5
      of amiloride

<400> SEQUENCE: 30

Xaa Xaa Xaa Xaa Xaa Xaa Glu Ser Leu Ala Tyr Tyr Thr Ala Xaa Xaa
1               5                   10                  15

Xaa Xaa Xaa Xaa
            20

<210> SEQ ID NO 31
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (14)..(20)
<223> OTHER INFORMATION: peptide is modified through a linkage to the C5
      of amiloride

<400> SEQUENCE: 31

Xaa Xaa Xaa Xaa Xaa Xaa Arg Ser Leu Ser Arg Leu Thr Ala Xaa Xaa
1               5                   10                  15

Xaa Xaa Xaa Xaa
            20

<210> SEQ ID NO 32
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (14)..(20)
<223> OTHER INFORMATION: the peptide is modified by AMIDATION at the
      C-terminus

<400> SEQUENCE: 32

Xaa Xaa Xaa Xaa Xaa Xaa Arg Ser Leu Ser Arg Leu Thr Ala Xaa Xaa
1               5                   10                  15

Xaa Xaa Xaa Xaa
            20

<210> SEQ ID NO 33
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE

```
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (14)..(20)
<223> OTHER INFORMATION: peptide is modified at the C-terminus by a
      methyl group through an ester linkage

<400> SEQUENCE: 33

Xaa Xaa Xaa Xaa Xaa Xaa Arg Ser Leu Ser Arg Leu Thr Ala Xaa Xaa
1               5                   10                  15

Xaa Xaa Xaa Xaa
            20

<210> SEQ ID NO 34
<211> LENGTH: 20
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(20)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (14)..(20)
<223> OTHER INFORMATION: peptide is modified through a linkage to the C5
      of amiloride

<400> SEQUENCE: 34

Xaa Xaa Xaa Xaa Xaa Xaa Arg Ser Leu Ser Arg Leu Thr Ala Xaa Xaa
1               5                   10                  15

Xaa Xaa Xaa Xaa
            20

<210> SEQ ID NO 35
<211> LENGTH: 21
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(21)
<223> OTHER INFORMATION: Xaa is any amino acid or absent
<220> FEATURE:
<221> NAME/KEY: MOD_RES
<222> LOCATION: (15)..(21)
<223> OTHER INFORMATION: peptide is modified through a linkage to the C5
      of amiloride

<400> SEQUENCE: 35

Xaa Xaa Xaa Xaa Xaa Xaa Arg Ser Leu Ser Arg Leu Thr Ala Gly Xaa
1               5                   10                  15

Xaa Xaa Xaa Xaa Xaa
            20

<210> SEQ ID NO 36
<211> LENGTH: 21
```

```
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(21)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (15)..(21)
<223> OTHER INFORMATION: the peptide is modified by AMIDATION at the
      C-terminus

<400> SEQUENCE: 36

Xaa Xaa Xaa Xaa Xaa Xaa Arg Ser Leu Ser Arg Leu Thr Ala Gly Xaa
1               5                   10                  15

Xaa Xaa Xaa Xaa Xaa
            20

<210> SEQ ID NO 37
<211> LENGTH: 21
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(21)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (15)..(21)
<223> OTHER INFORMATION: peptide is modified at the C-terminus by a
      methyl group through an ester linkage

<400> SEQUENCE: 37

Xaa Xaa Xaa Xaa Xaa Xaa Arg Ser Leu Ser Arg Leu Thr Ala Gly Xaa
1               5                   10                  15

Xaa Xaa Xaa Xaa Xaa
            20

<210> SEQ ID NO 38
<211> LENGTH: 21
<212> TYPE: PRT
<213> ORGANISM: Artificial Sequence
<220> FEATURE:
<223> OTHER INFORMATION: modified peptide substrate of MMP-2
<220> FEATURE:
<221> NAME/KEY: MISC_FEATURE
<222> LOCATION: (1)..(21)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride
<220> FEATURE:
<221> NAME/KEY: MOD_RES
<222> LOCATION: (15)..(21)
<223> OTHER INFORMATION: peptide is modified through a linkage to the C5
      of amiloride
```

```
<400> SEQUENCE: 38

Xaa Xaa Xaa Xaa Xaa Xaa Arg Ser Leu Ser Arg Leu Thr Ala Gly Xaa
1               5                   10                  15

Xaa Xaa Xaa Xaa Xaa
            20

<210> SEQ ID NO 39
<211> LENGTH: 5
<212> TYPE: PRT
<213> ORGANISM: Artificial Sequence
<220> FEATURE:
<223> OTHER INFORMATION: enkephalin analogue compound 3b
<220> FEATURE:
<221> NAME/KEY: MOD_RES
<222> LOCATION: (1)..(1)
<223> OTHER INFORMATION: peptide is modified at the N-terminus through
      an amino linkage to the C5 of amiloride
<220> FEATURE:
<221> NAME/KEY: MISC_FEATURE
<222> LOCATION: (2)..(2)
<223> OTHER INFORMATION: Xaa is D-alanine
<220> FEATURE:
<221> NAME/KEY: MISC_FEATURE
<222> LOCATION: (5)..(5)
<223> OTHER INFORMATION: Xaa is D-leucine

<400> SEQUENCE: 39

Gly Xaa Gly Phe Xaa
1               5

<210> SEQ ID NO 40
<211> LENGTH: 6
<212> TYPE: PRT
<213> ORGANISM: Artificial Sequence
<220> FEATURE:
<223> OTHER INFORMATION: enkephalin analogue compound 3c
<220> FEATURE:
<221> NAME/KEY: MOD_RES
<222> LOCATION: (1)..(1)
<223> OTHER INFORMATION: peptide is modified at the N-terminus through
      an amino linkage to the C5 of amiloride

<400> SEQUENCE: 40

Gly Gly Gly Gly Phe Leu
1               5

<210> SEQ ID NO 41
<211> LENGTH: 5
<212> TYPE: PRT
<213> ORGANISM: Artificial Sequence
<220> FEATURE:
<223> OTHER INFORMATION: enkephalin analogue for the preparation of
      compound 3d

<400> SEQUENCE: 41

Gly Gly Gly Phe Leu
1               5

<210> SEQ ID NO 42
<211> LENGTH: 5
<212> TYPE: PRT
<213> ORGANISM: Artificial Sequence
<220> FEATURE:
<223> OTHER INFORMATION: [Leu]-enkephalin peptide

<400> SEQUENCE: 42

Tyr Gly Gly Phe Leu
1               5
```

```
<210> SEQ ID NO 43
<211> LENGTH: 4
<212> TYPE: PRT
<213> ORGANISM: Artificial Sequence
<220> FEATURE:
<223> OTHER INFORMATION: C(2) amiloride conjugate
<220> FEATURE:
<221> NAME/KEY: MOD_RES
<222> LOCATION: (4)..(4)
<223> OTHER INFORMATION: peptide is modified at the C-terminus through a
      guanidino linkage to the C2 of amiloride

<400> SEQUENCE: 43

Gly Gly Gly Gly
1

<210> SEQ ID NO 44
<211> LENGTH: 5
<212> TYPE: PRT
<213> ORGANISM: Artificial Sequence
<220> FEATURE:
<223> OTHER INFORMATION: C(2) amiloride conjugate
<220> FEATURE:
<221> NAME/KEY: MOD_RES
<222> LOCATION: (5)..(5)
<223> OTHER INFORMATION: peptide is modified at the C-terminus through a
      guanidino linkage to the C2 of amiloride

<400> SEQUENCE: 44

Gly Gly Gly Gly Gly
1               5

<210> SEQ ID NO 45
<211> LENGTH: 4
<212> TYPE: PRT
<213> ORGANISM: Artificial Sequence
<220> FEATURE:
<223> OTHER INFORMATION: enkephalin peptide analog
<220> FEATURE:
<221> NAME/KEY: MISC_FEATURE
<222> LOCATION: (2)..(2)
<223> OTHER INFORMATION: Xaa is d-alanine
<220> FEATURE:
<221> NAME/KEY: MOD_RES
<222> LOCATION: (4)..(4)
<223> OTHER INFORMATION: peptide is modified by AMIDATION at the
      C-terminus

<400> SEQUENCE: 45

Thr Xaa Gly Phe
1

<210> SEQ ID NO 46
<211> LENGTH: 4
<212> TYPE: PRT
<213> ORGANISM: Artificial Sequence
<220> FEATURE:
<223> OTHER INFORMATION: C(2) amiloride conjugate enkephalin peptide
      analog
<220> FEATURE:
<221> NAME/KEY: MOD_RES
<222> LOCATION: (4)..(4)
<223> OTHER INFORMATION: peptide is modified at the C-terminus through a
      guanidino linkage to the C2 of amiloride

<400> SEQUENCE: 46

Tyr Gly Gly Gly
1

<210> SEQ ID NO 47
```

```
<211> LENGTH: 5
<212> TYPE: PRT
<213> ORGANISM: Artificial Sequence
<220> FEATURE:
<223> OTHER INFORMATION: C(2) amiloride conjugate enkephalin peptide
      analog
<220> FEATURE:
<221> NAME/KEY: MISC_FEATURE
<222> LOCATION: (4)..(4)
<223> OTHER INFORMATION: Xaa is D-alanine
<220> FEATURE:
<221> NAME/KEY: MOD_RES
<222> LOCATION: (5)..(5)
<223> OTHER INFORMATION: peptide is modified at the C-terminus through a
      guanidino linkage to the C2 of amiloride

<400> SEQUENCE: 47

Tyr Gly Gly Xaa Gly
1               5

<210> SEQ ID NO 48
<211> LENGTH: 5
<212> TYPE: PRT
<213> ORGANISM: Artificial Sequence
<220> FEATURE:
<223> OTHER INFORMATION: C(2) amiloride conjugate enkephalin peptide
      analog
<220> FEATURE:
<221> NAME/KEY: MISC_FEATURE
<222> LOCATION: (2)..(2)
<223> OTHER INFORMATION: Xaa is D-alanine
<220> FEATURE:
<221> NAME/KEY: MOD_RES
<222> LOCATION: (5)..(5)
<223> OTHER INFORMATION: peptide is modified at the C-terminus through a
      guanidino linkage to the C2 of amiloride

<400> SEQUENCE: 48

Tyr Xaa Gly Pro Gly
1               5

<210> SEQ ID NO 49
<211> LENGTH: 9
<212> TYPE: PRT
<213> ORGANISM: Artificial Sequence
<220> FEATURE:
<223> OTHER INFORMATION: C(2) amiloride conjugate MMP2 peptide substrate
<220> FEATURE:
<221> NAME/KEY: MOD_RES
<222> LOCATION: (9)..(9)
<223> OTHER INFORMATION: peptide is modified at the C-terminus through a
      guanidino linkage to the C2 of amiloride

<400> SEQUENCE: 49

Glu Ser Leu Ala Tyr Tyr Thr Ala Gly
1               5

<210> SEQ ID NO 50
<211> LENGTH: 9
<212> TYPE: PRT
<213> ORGANISM: Artificial Sequence
<220> FEATURE:
<223> OTHER INFORMATION: C(2) amiloride conjugate MMP2 peptide substrate
<220> FEATURE:
<221> NAME/KEY: MOD_RES
<222> LOCATION: (9)..(9)
<223> OTHER INFORMATION: peptide is modified at the C-terminus through a
      guanidino linkage to the C2 of amiloride

<400> SEQUENCE: 50

Arg Ser Leu Ser Arg Leu Thr Ala Gly
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: C(2) amiloride conjugate MMP2 peptide substrate
      analog
<220> FEATURE:
<221> NAME/KEY: MISC_FEATURE
<222> LOCATION: (4)..(4)
<223> OTHER INFORMATION: Xaa is D-alanine
<220> FEATURE:
<221> NAME/KEY: MOD_RES
<222> LOCATION: (9)..(9)
<223> OTHER INFORMATION: peptide is modified at the C-terminus through a
      guanidino linkage to the C2 of amiloride

<400> SEQUENCE: 51

Glu Ser Leu Xaa Tyr Tyr Thr Ala Gly
1               5

<210> SEQ ID NO 52
<211> LENGTH: 9
<212> TYPE: PRT
<213> ORGANISM: Artificial Sequence
<220> FEATURE:
<223> OTHER INFORMATION: C(2) amiloride conjugate MMP2 peptide substrate
      analog
<220> FEATURE:
<221> NAME/KEY: MISC_FEATURE
<222> LOCATION: (6)..(6)
<223> OTHER INFORMATION: Xaa is D-leucine
<220> FEATURE:
<221> NAME/KEY: MOD_RES
<222> LOCATION: (9)..(9)
<223> OTHER INFORMATION: peptide is modified at the C-terminus through a
      guanidino linkage to the C2 of amiloride

<400> SEQUENCE: 52

Arg Ser Leu Ser Arg Xaa Thr Ala Gly
1               5

<210> SEQ ID NO 53
<211> LENGTH: 10
<212> TYPE: PRT
<213> ORGANISM: Artificial Sequence
<220> FEATURE:
<223> OTHER INFORMATION: C(2) amiloride conjugate MMP2 peptide substrate
<220> FEATURE:
<221> NAME/KEY: MOD_RES
<222> LOCATION: (10)..(10)
<223> OTHER INFORMATION: peptide is modified at the C-terminus through a
      guanidino linkage to the C2 of amiloride

<400> SEQUENCE: 53

Arg Ser Leu Ser Arg Leu Thr Ala Gly Gly
1               5                   10

<210> SEQ ID NO 54
<211> LENGTH: 4
<212> TYPE: PRT
<213> ORGANISM: Artificial Sequence
<220> FEATURE:
<223> OTHER INFORMATION: C(5) amiloride peptide conjugate
<220> FEATURE:
<221> NAME/KEY: MOD_RES
<222> LOCATION: (1)..(1)
<223> OTHER INFORMATION: peptide is modified at the N-terminus through
      an amino linkage to the C5 of amiloride

<400> SEQUENCE: 54
```

```
Gly Gly Gly Gly
1

<210> SEQ ID NO 55
<211> LENGTH: 5
<212> TYPE: PRT
<213> ORGANISM: Artificial Sequence
<220> FEATURE:
<223> OTHER INFORMATION: C(5) amiloride peptide conjugate
<220> FEATURE:
<221> NAME/KEY: MOD_RES
<222> LOCATION: (1)..(1)
<223> OTHER INFORMATION: peptide is modified at the N-terminus through
      an amino linkage to the C5 of amiloride

<400> SEQUENCE: 55

Gly Gly Gly Gly Gly
1               5

<210> SEQ ID NO 56
<211> LENGTH: 5
<212> TYPE: PRT
<213> ORGANISM: Artificial Sequence
<220> FEATURE:
<223> OTHER INFORMATION: C(5) amiloride peptide conjugate analog
<220> FEATURE:
<221> NAME/KEY: MOD_RES
<222> LOCATION: (1)..(1)
<223> OTHER INFORMATION: peptide is modified at the N-terminus through
      an amino linkage to the C5 of amiloride
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 56

Gly Xaa Gly Xaa Gly
1               5

<210> SEQ ID NO 57
<211> LENGTH: 14
<212> TYPE: PRT
<213> ORGANISM: Artificial Sequence
<220> FEATURE:
<223> OTHER INFORMATION: C(5) amiloride conjugate calpain peptide
      substrate
<220> FEATURE:
<221> NAME/KEY: MISC_FEATURE
<222> LOCATION: (1)..(14)
<223> OTHER INFORMATION: Xaa is any amino acid or absent
<220> FEATURE:
<221> NAME/KEY: MOD_RES
<222> LOCATION: (1)..(7)
<223> OTHER INFORMATION: peptide is modified through a linkage to the C2
      of amiloride

<400> SEQUENCE: 57

Xaa Xaa Xaa Xaa Xaa Xaa Leu Tyr Xaa Xaa Xaa Xaa Xaa Xaa
1               5                   10
```

AMINO ACID AND PEPTIDE CONJUGATES OF AMILORIDE AND METHODS OF USE THEREOF

CROSS-REFERENCES TO RELATED APPLICATIONS

The present application claims priority to U.S. Provisional Application No. 60/538,972, filed Jan. 23, 2004, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under 5R01 NS040489 awarded by the National Institutes of Health. The Government has certain rights in the invention.

BACKGROUND OF THE INVENTION

High-grade malignant gliomas (i.e., astrocytomas) are the most commonly occurring type of lethal adult brain tumor and are increasing in incidence (Legler et al., *J. National Cancer Inst.*, 91:1382-1390 (1999)). The median survival is approximately 9-12 months following diagnosis, as the tumors are usually refractory to aggressive multimodal therapy (Brandes et al., *Amer. J. Clin. Onc.*, 22:387-390 (1999)). Gliomas exhibit increased glycolytic fluxes associated with elevated lactate/pyruvate ratios that would indicate an acidotic intracellular pH (pH$_i$) (Miccoli et al., *Biochem. J.*, 313:957-962 (1996)). However, several $^{31}$P spectroscopic (i.e., NMR) studies measured intracellular human glioma pH in situ and reported alkaline values (pH 7.12-7.24) as compared with the surrounding brain (pH 6.99-7.05) (Hubesch et al., *Radiology*, V174:401-409 (1990); Rutter et al, *Invest. Radiology*, V30:359-366 (1995)). An alkaline pH$_i$ has also been reported in tumor cell lines (Wike-Hooley et al., *Radiother. Oncol.*, 2:343-366 (1984); Vaupel et al., *Adv. Exp. Med. Biol.*, 248:835-845 (1989)). In particular, several human and rat malignant glioma cell lines were reported to exhibit intracellular alkalosis (pH$_i$ 7.2-7.5) when compared to rat astrocyte primary cultures (pH$_i$ 6.9-7.0) (McLean et al., *Amer. J. Physiol. Cell Physiol.*, 278:C676-688 (2000)).

Malignant gliomas, like many highly proliferative tumors, have increased glycolytic fluxes with elevated levels of intracellular lactate and pyruvate (Oudard et al., *Anticancer Res.*, 17:1903-1911 (1997); Erecinska et al., *J. Neurochem.*, 65:2765-2772 (1995)). Glycolytic rates are optimal at an alkalotic pH$_i$ and inhibition of glycolytic flux is sensitive to modest reductions in pH$_i$. (Dobson et al., *Amer. J. Physiol.*, 250:R71-76 (1986)). Obligate tumor DNA synthesis and cell cycle progression are also optimal at an alkalotic pH$_i$ (Hasuda et al., *One. Res.*, V6:259-268 (1994)). For example, a reduction in pH$_i$ has been associated with reduced rates of proliferation and growth arrest in transformed cell types (Musgrove et al., *Exp. Cell Res.*, 172:65-75 (1987); Rotin et al., *Cancer Res.*, 49:205-211 (1989); Horvat et al., *Eur. J. Cancer*, 29A:132-217 (1992)).

The inhibitory effect of a reduction in pH$_i$ on tumor cell proliferation is thought to be primarily due to the glycolytic enzyme phosphofructokinase (PFK), which has a pH optimum of 7.2 and is the rate limiting step for glycolysis. In addition, hexokinase activity and intracellular distribution are affected by even modest reductions from an optimal alkaline pH$_i$ (Miccoli et al., id), as its activity is required for glucose entry into the glycolytic pathway and is increased in gliomas and in many other proliferative tumors (Katabi et al., *Hum. Gene Ther.*, 10:155-164 (1999); Sebastian et al., *Tumour Biol.*, 19:253-260 (1998)). As such, given the elevated glucose consumption, lactate production, and hypoxic or anoxic environments of malignant gliomas, these tumors may be particularly sensitive to pH$_i$ reductions. For example, reducing the pH$_i$ in rat C6 gliomas from 7.3 to 6.4 decreased the enzymatic product of PFK by 50% after 15 minutes while doubling the accumulation of substrate (Erecinska et al., id). Lactate and pyruvate levels decreased by 54% and 69%, respectively, during this brief period. Thus, these data confirm that glycolysis in C6 glioma cells is extremely sensitive to modest reductions in pH$_i$.

The alkalosis in glioma cells was reported to result from the persistent activation of NHE1, a ubiquitously-expressed type 1 Na$^+$—H$^+$ exchanger involved in intracellular pH and volume regulation (McLean et al., supra; Hegde et al., *J. Pharmacol. Exp. Ther.*, 310:67-74 (2004)). The Na$^+$—H$^+$ exchanger (NHE) represents a family of sodium-dependent transport proteins that participate in various cellular functions (Orlowski et al., *J. Biol. Chem.*, 272:22373-22376 (1997)). Seven isoforms (i.e., NHE1-7) have been identified (Numata et al., *J. Biol. Chem.*, 276:17387-17394 (2001); Brett et al., *Am. J. Physiol.*, 282:C1031-1041 (2002); Slepkov et al., *Biochem. Cell Biol.*, 80:499-508 (2002)). NHE1 and NHE5-7 are particularly important in maintaining the pH$_i$ in human heart and brain. Additionally, increased NHE1 activity has also been observed in other cancer cell lines, including colon and bladder (Bischof et al., *Biochimica et Biophysica Acta*, 1282:131-139 (1996); Boyer et al., *Cancer Res.*, 52:4441-4447 (1992)).

Amiloride (3,5-diamino-6-chloro-N-(diaminomethylene) pyrazinecarboxamide), originally developed as an antidiuretic drug, displays antiproliferative effects on several cancer cell lines (Horvat et al., id; Hasuda et al., id; Garcá-Cañero et al., *Tox. Letters*, 106:215-228 (1999); Wong et al., *Brit. J. Cancer*, 87:238-245 (2002)), including glioma cells (Szolgay-Daniel et al., *Cancer Res.*, 51:1039-1044 (1991)). Amiloride is thought to block tumor cell proliferation through inhibition of specific ion transport systems; in particular, amiloride displays inhibitory activity toward several classes of Na$^+$-dependent membrane transporters, including NHE1, NCX (a Na$^+$-Ca$^{2+}$ exchanger), the Na$^+$/K$^+$-ATPase, Na$^+$-coupled solute transport, voltage-gated Na$^+$ channels, etc. However, the hydrophobic nature of amiloride, its weak inhibitory activity toward transporters such as NHE1, and its inability to cross the blood brain barrier (BBB) make it unsuitable as an effective drug for treating cancers such as gliomas.

In addition to amiloride, various amiloride derivatives have been synthesized and their activities on ion transporters and glioma cells have been determined. However, such amiloride derivatives are also unsuitable as effective drugs for cancer therapy due to their non-specificity, toxicity, and/or inability to access the central nervous system (i.e., cross the BBB). Agents that selectively inhibit NHE, such as cariporide, do not kill glioma cells and direct acidification does not kill glioma cells (Hegde et al., *J. Pharmacol. Exp. Ther.*, 310:67-74 (2004)). Additional inhibition of NCX is required to confer cytotoxicity to cancer cells as is observed with amiloride and dichlorobenzamil, which inhibit both NHE and NCX. Amiloride and dichlorobenzamil are hydrophobic compounds that are rapidly taken up by glioma cells that likely contribute to their nonspecific toxicity (Palandoken et al., *J. Pharmacol. Exp. Ther.*, October 27; Epub. (2004)). Although conjugation of alkyl, alkenyl, or benzyl moieties to either the C(2) guanidine group or the C(5) amino group of amiloride has been reported to increase the inhibitory efficacy of NHE1 and/or other ion transporters (e.g., NCX) (L'Allemain et al., *J. Biol. Chem.*, 259:4313-4319 (1984); Frelin et al., *Biochimie*, 70:1285-1290 (1988)), these derivatives suffer from the same disadvantages as amiloride (e.g., non-specificity, toxicity, and/or inablity to access the central nervous system). For example, a benyl derivative of amiloride, 2,4-dichlorobenzamil (DCB), is highly toxic and causes lethality when administered.

Thus, there is a need to develop amiloride derivatives (e.g., amiloride conjugates) that (1) target particular cells and/or tissues with high specificity and potency; (2) are low in toxicity to non-targeted cells and/or tissues; (3) are able to be transported across the BBB to access the central nervous system; and (4) kill tumor cell populations residing in hypoxic-ischemic tumor microenvironments that are normally resistant to conventional chemotherapy or radiotherapy. The present invention satisfies this and other needs.

BRIEF SUMMARY OF THE INVENTION

The present invention provides novel amiloride conjugates and methods of use thereof. The amiloride conjugates exhibit high specificity and potency, low toxicity, and are transported across the BBB into the central nervous system. In particular, the amiloride conjugates of the present invention have the following advantages: (1) amiloride-peptide conjugates with peptidase cleavage sites are not only capable of traversing the BBB, but upon cleavage by brain- or tumor-specific peptidases in the central nervous system, release hydrophilic proteolytic products (e.g., C2am-Gly, C5am-Gly) that act at the tumor cell surface, thus minimizing toxic side-effects; (2) amiloride-peptide conjugates with peptidase cleavage sites are biologically inactive NHE inhibitor prodrugs that can be administered prior to the onset of ischemia and subsequently activated by peptidases selectively expressed by the ischemic tissue (e.g., brain, heart); and (3) the conjugates kill hypoxic-ischemic tumor cells (i.e., tumor cells with little or no blood supply) that are not normally killed by conventional therapy.

As such, in one aspect, the present invention provides a conjugate having the formula:

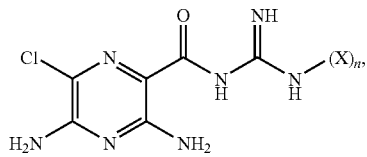

wherein X is n independently selected amino acids and n is an integer greater than or equal to 1.

In another aspect, the present invention provides a conjugate having the formula:

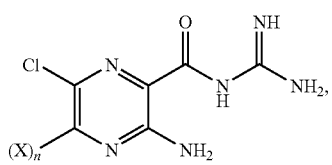

wherein X is n independently selected amino acids and n is an integer greater than or equal to 1.

In yet another aspect, the present invention provides a conjugate having the formula:

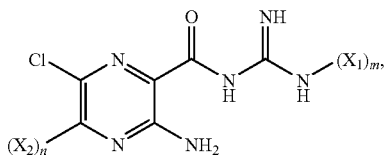

wherein $X_1$ and $X_2$ are m and n independently selected amino acids, respectively, and m and n are independently selected integers greater than or equal to 1.

In still yet another aspect, the present invention provides a conjugate having the formula:

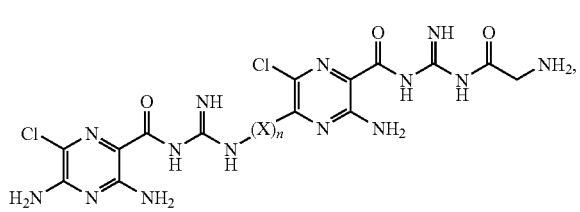

wherein X is n independently selected amino acids and n is an integer greater than or equal to 1.

In a further aspect, the present invention provides a method for treating cancer in a subject in need thereof, the method comprising:

administering to the subject a therapeutically effective amount of a conjugate having the formula:

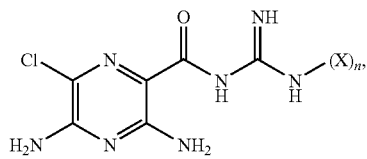

wherein X is n independently selected amino acids and n is an integer greater than or equal to 1.

In another aspect, the present invention provides a method for treating cancer in a subject in need thereof, the method comprising:

administering to the subject a therapeutically effective amount of a conjugate having the formula:

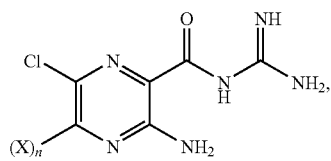

wherein X is n independently selected amino acids and n is an integer greater than or equal to 1.

In yet another aspect, the present invention provides a method for treating cancer in a subject in need thereof, the method comprising:

administering to the subject a therapeutically effective amount of a conjugate having the formula:

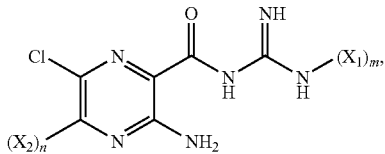

wherein $X_1$ and $X_2$ are m and n independently selected amino acids, respectively, and m and n are independently selected integers greater than or equal to 1.

In still yet another aspect, the present invention provides a method for treating cancer in a subject in need thereof, the method comprising:

administering to the subject a therapeutically effective amount of a conjugate having the formula:

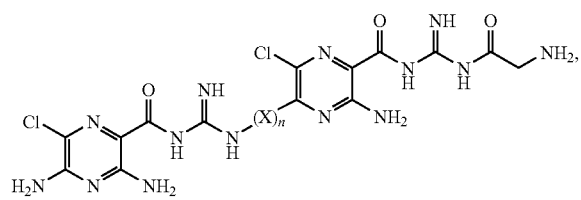

wherein X is n independently selected amino acids and n is an integer greater than or equal to 1.

The present invention also provides methods for administering hydrophobic amiloride-peptide conjugates that can then be converted in vivo to hydrophilic agents upon the action of a peptidase.

In one aspect, the present invention provides a method for treating a central nervous system disease or disorder in a subject in need thereof, the method comprising:

administering to the subject a therapeutically effective amount of a conjugate having the formula:

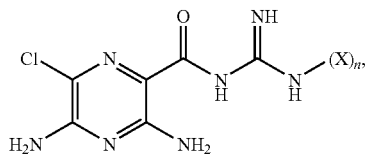

wherein X is a peptide comprising n independently selected amino acids and n is an integer greater than 1, and wherein the peptide is selectively cleaved by a peptidase in the central nervous system.

In another aspect, the present invention provides a method for treating a central nervous system disease or disorder in a subject in need thereof, the method comprising:

administering to the subject a therapeutically effective amount of a conjugate having the formula:

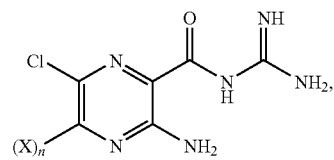

wherein X is a peptide comprising n independently selected amino acids and n is an integer greater than 1, and wherein the peptide is selectively cleaved by a peptidase in the central nervous system.

In yet another aspect, the present invention provides a method for treating a central nervous system disease or disorder in a subject in need thereof, the method comprising:

administering to the subject a therapeutically effective amount of a conjugate having the formula:

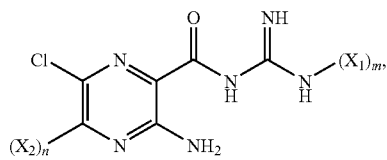

wherein $X_1$ and $X_2$ are peptides comprising m and n independently selected amino acids, respectively, and m and n are independently selected integers greater than 1, and wherein at least one of the peptides is selectively cleaved by a peptidase in the central nervous system.

In still yet another aspect, the present invention provides a method for treating a central nervous system disease or disorder in a subject in need thereof, the method comprising:

administering to the subject a therapeutically effective amount of a conjugate having the formula:

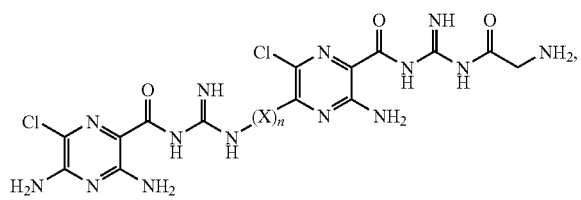

wherein X is a peptide comprising n independently selected amino acids and n is an integer greater than 1, and wherein the peptide is selectively cleaved by a peptidase in the central nervous system.

In a further aspect, the present invention provides a method for preventing or reducing ischemia-reperfusion injury in a subject in need thereof, the method comprising:

administering to the subject prior to the onset of ischemia a therapeutically effective amount of a conjugate having the formula:

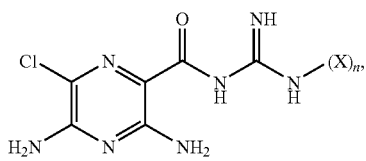

wherein X is a peptide comprising n independently selected amino acids and n is an integer greater than 1, and wherein the peptide is selectively cleaved by a peptidase in the ischemic tissue.

In another aspect, the present invention provides a method for preventing or reducing ischemia-reperfusion injury in a subject in need thereof, the method comprising:
administering to the subject prior to the onset of ischemia a therapeutically effective amount of a conjugate having the formula:

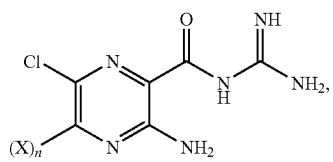

wherein X is a peptide comprising n independently selected amino acids and n is an integer greater than 1, and wherein the peptide is selectively cleaved by a peptidase in the ischemic tissue.

In yet another aspect, the present invention provides a method for preventing or reducing ischemia-reperfusion injury in a subject in need thereof, the method comprising:
administering to the subject prior to the onset of ischemia a therapeutically effective amount of a conjugate having the formula:

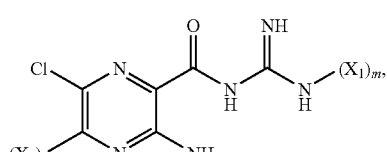

wherein $X_1$ and $X_2$ are peptides comprising m and n independently selected amino acids, respectively, and m and n are independently selected integers greater than 1, and wherein at least one of the peptides is selectively cleaved by a peptidase in the ischemic tissue.

In still yet another aspect, the present invention provides a method for preventing or reducing ischemia-reperfusion injury in a subject in need thereof, the method comprising:
administering to the subject prior to the onset of ischemia a therapeutically effective amount of a conjugate having the formula:

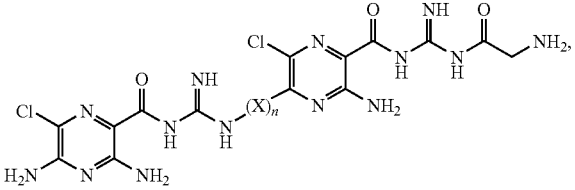

wherein X is a peptide comprising n independently selected amino acids and n is an integer greater than 1, and wherein the peptide is selectively cleaved by a peptidase in the ischemic tissue.

In addition, the present invention provides kits for administering hydrophobic amiloride-peptide conjugates that can then be converted in vivo to hydrophilic agents upon the action of a peptidase.

In one aspect, the present invention provides a kit for the treatment of a central nervous system disease or disorder, the kit comprising:
(a) a container holding a conjugate having the formula:

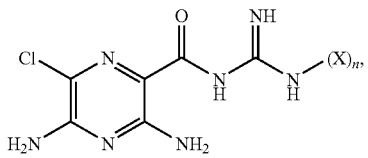

wherein X is a peptide comprising n independently selected amino acids, n is an integer greater than 1, and the peptide contains a cleavage site recognized (i.e., selectively cleaved) by a peptidase in the central nervous system; and (b) directions for use of the conjugate in the treatment of the central nervous system disease or disorder.

In another aspect, the present invention provides a kit for the treatment of a central nervous system disease or disorder, the kit comprising:
(a) a container holding a conjugate having the formula:

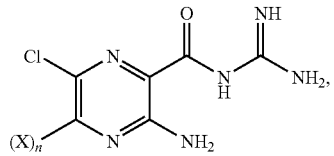

wherein X is a peptide comprising n independently selected amino acids, n is an integer greater than 1, and the peptide contains a cleavage site recognized by a peptidase in the central nervous system; and (b) directions for use of the conjugate in the treatment of the central nervous system disease or disorder.

In yet another aspect, the present invention provides a kit for the treatment of a central nervous system disease or disorder, the kit comprising:

(a) a container holding a conjugate having the formula:

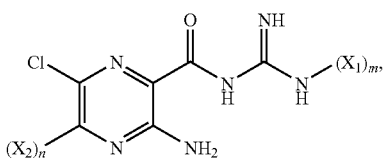

wherein $X_1$ and $X_2$ are peptides comprising m and n independently selected amino acids, respectively; and m and n are independently selected integers greater than 1, and at least one of the peptides contains a cleavage site recognized by a peptidase in the central nervous system; and (b) directions for use of the conjugate in the treatment of the central nervous system disease or disorder.

In still yet another aspect, the present invention provides a kit for the treatment of a central nervous system disease or disorder, the kit comprising:

(a) a container holding a conjugate having the formula:

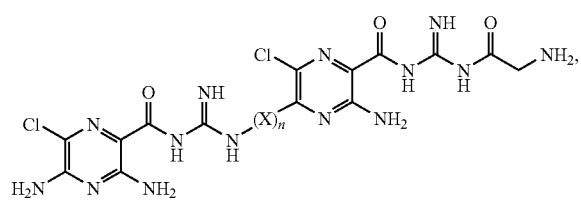

wherein X is a peptide comprising n independently selected amino acids, n is an integer greater than 1, and the peptide contains a cleavage site recognized by a peptidase in the central nervous system; and (b) directions for use of the conjugate in the treatment of the central nervous system disease or disorder.

In a further aspect, the present invention provides a kit for the prevention or reduction of ischemia-reperfusion injury, the kit comprising:

(a) a container holding a conjugate having the formula:

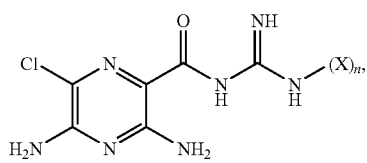

wherein X is a peptide comprising n independently selected amino acids, n is an integer greater than 1, and the peptide contains a cleavage site recognized (i.e., selectively cleaved) by a peptidase in the ischemic tissue; and (b) directions for use of the conjugate in the prevention or reduction of the ischemia-reperfusion injury.

In another aspect, the present invention provides a kit for the prevention or reduction of ischemia-reperfusion injury, the kit comprising:

(a) a container holding a conjugate having the formula:

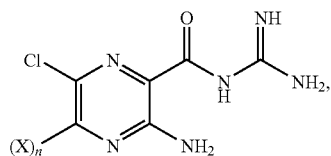

wherein X is a peptide comprising n independently selected amino acids, n is an integer greater than 1, and the peptide contains a cleavage site recognized by a peptidase in the ischemic tissue; and (b) directions for use of the conjugate in the prevention or reduction of the ischemia-reperfusion injury.

In yet another aspect, the present invention provides a kit for the prevention or reduction of ischemia-reperfusion injury, the kit comprising:

(a) a container holding a conjugate having the formula:

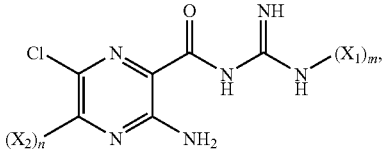

wherein $X_1$ and $X_2$ are peptides comprising m and n independently selected amino acids, respectively; and m and n are independently selected integers greater than 1, and at least one of the peptides contains a cleavage site recognized by a peptidase in the ischemic tissue; and (b) directions for use of the conjugate in the prevention or reduction of the ischemia-reperfusion injury.

In still yet another aspect, the present invention provides a kit for the prevention or reduction of ischemia-reperfusion injury, the kit comprising:

(a) a container holding a conjugate having the formula:

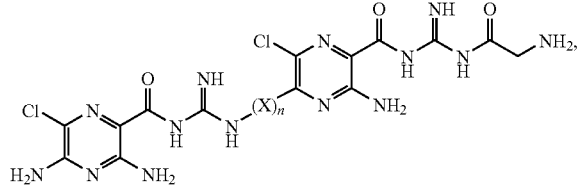

wherein X is a peptide comprising n independently selected amino acids, n is an integer greater than 1, and the peptide contains a cleavage site recognized by a peptidase in the ischemic tissue; and (b) directions for use of the conjugate in the prevention or reduction of the ischemia-reperfusion injury.

Other objects, features, and advantages of the present invention will be apparent to one of skill in the art from the following detailed description and figures.

BRIEF DESCRIPTION OF THE DRAWINGS

In FIG. 1A, increased activation of NHE1 (1) in tumor cells causes intracellular alkalosis with an accumulation of $[Na^+]_i$ and $[Ca^{2+}]_i$.

FIG. 1B shows that the cell death is achieved by the inhibition of NCX (2), which results in $[Ca^{2+}]_i$ accumulation, and the inhibition of NHE1, which results in a reduction in $pH_i$, impairing glycolysis and leading to the release of additional calcium from energetically sensitive intracellular stores such as the mitochondria (mito, 4) and the endoplasmic reticulum (ER, 5).

In FIG. 5A, amiloride did not affect balance and fine motor coordination in tumor-implanted rats. FIG. 5B shows that amiloride treatment did affect spatial learning performance in tumor-implanted rats. FIG. 5C shows that amiloride treatment did not affect memory in a spatial learning task in tumor-implanted rats.

FIG. 9 shows fluorescent microscopy images of U87 glioma cells following 90 min incubation with (A) 50 μM amiloride; (B) 50 μM ethylisopropylamiloride (EIPA); or following 180 min incubation with (C) 50 μM compound 3a. In FIG. 9C, a single trypan-positive, dying or dead U87 cell demonstrates intracellular accumulation of compound 3a (arrow). FIG. 9D shows a bright-field microscopy image of the same cells as in FIG. 9C with the corresponding trypan-positive cell shown by an arrow (bar=10 μm). Viable cells did not accumulate compound 3a. Fluorescent determinations were performed three times for each compound.

DETAILED DESCRIPTION OF THE INVENTION

I. Definitions

Figure 1:
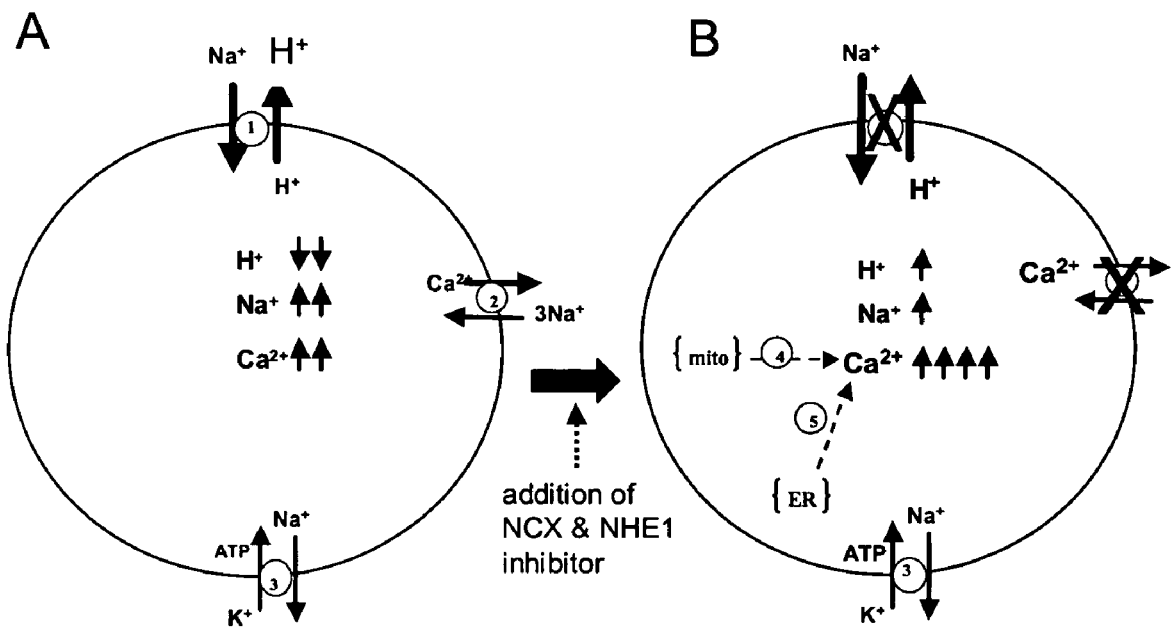
FIG. 1 illustrates a model for tumor cell death induced by the amiloride conjugates of the present invention.

As used herein, the following terms have the meanings ascribed to them unless specified otherwise.

The term "conjugate" refers to a chemical compound that has been formed by the joining or attachment of two or more compounds. In particular, a conjugate of the present invention comprises an amino acid or peptide covalently attached to amiloride or other suitable therapeutic agent.

The term "amino acid" refers to naturally occurring α-amino acids and their stereoisomers, as well as unnatural amino acids such as amino acid analogs, amino acid mimetics, synthetic amino acids, β-amino acids, γ-amino acids, N-methyl amino acids, and N-substituted glycines in either the L- or D-configuration that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Stereoisomers" of naturally occurring amino acids refers to mirror image isomers of the naturally occurring amino acids, such as D-amino acids. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable side chains (e.g., R groups) for β- or γ-amino acids include, but are not limited to, side chains present in naturally occurring amino acids and unnatural amino acids such as amino acid analogs, amino acid mimetics, synthetic amino acids, N-methyl amino acids, and N-substituted glycines.

The term "N-substituted glycine" refers to a glycine amino acid where an amino acid side chain is attached to the glycine nitrogen atom. Suitable amino acid side chains (e.g., R groups) include, but are not limited to, side chains present in naturally occurring amino acids and side chains present in unnatural amino acids such as amino acid analogs, amino acid mimetics, synthetic amino acids, β-amino acids, and γ-amino acids. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)-N-(1-phenylethyl)glycine, N-cyclohexylmethylglycine, N-(2-phenylethyl) glycine, N-(3-phenylpropyl)glycine, N-(6-aminogalactosyl) glycine, N-(2-(3'-indolylethyl)glycine, N-(2-(p-methoxyphenylethyl))glycine, N-(2-(p-chlorophenylethyl) glycine, and N-[2-(p-hydroxyphenylethyl)]glycine. Such N-substituted glycines can have an L- or D-configuration. N-substituted glycine oligomers, referred to herein as "peptoids," have been shown to be protease resistant (Miller et al., *Drug Dev. Res.*, 35:20-32 (1995)). As such, an amiloride-peptoid conjugate is within the scope of the present invention.

Amino acids may be referred to herein by either their commonly known three letter symbols or by the one-letter symbols recommended by the IUPAC-IUB Biochemical Nomenclature Commission. D-amino acids are represented herein by a lower-case one-letter amino acid symbol (e.g., r for D-arginine), whereas L-amino acids are represented by an upper case one-letter amino acid symbol (e.g., R for L-arginine).

With respect to amino acid sequences, one of skill will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acids include, but are not limited to, naturally occurring amino acids such as α-amino acids having an L-configuration, stereoisomers of naturally occurring amino acids such as α-amino acids having a D-configuration, and unnatural amino acids such as amino acid analogs, amino acid mimetics, synthetic amino acids, β-amino acids, and γ-amino acids, in either the L- or D-configuration. For example, the unnatural amino acids of Liu and Lam (*Anal. Biochem.*, 295:9-16 (2001)) are suitable for use in the present invention.

Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1984).

The term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are conjugated via a peptide bond to the C(2) and/or C(5) glycine of C2am-Gly or C5am-Gly. However, the peptides can also be directly conjugated to the C(2) and/or C(5) position of amiloride (e.g., no glycine spacer.) The peptides of the present invention are preferably between 2 and 25 amino acids, more preferably between 2 and 10 amino acids, and most preferably between 2 and 8 amino acids in length. In a particularly preferred embodiment, the free amino-terminus and/or carboxyl-terminus on peptides are protected by an amide, a methyl ester, a succinyl, or an acetyl group. Further chemical modifications at positions 1, 3, 4, or 6 of the amiloride ring structure do not fundamentally alter the properties conferred by the primary chemical additions to the guandine moiety at C(2) and/or the amine moiety at C(5).

The terms "linker" and "spacer" are used interchangeably herein to refer to an amino acid or a doubly functionalized hydrocarbon chain that connects a peptide or an active pharmaceutical compound to the C(2) and/or C(5) position of amiloride. Preferably, the amino acid linker on amiloride is glycine, e.g., C2am-Gly, C5am-Gly, or C2,5am-(Gly)$_2$. Preferably, the doubly functionalized hydrocarbon chain on amiloride is a diamine, e.g., $NH_2$—$(CH2)_n$—$NH_2$, wherein n is from 1 to 6. Preferably, the peptide connected to amiloride via a linker is selectively cleaved by a peptidase. Preferably, the active pharmaceutical compound connected to amiloride via a linker is tamoxifen, e.g., for breast cancer therapy.

The term "cancer" refers to any of various malignant neoplasms characterized by the proliferation of cells with altered cell cycle regulation that tend to invade surrounding tissue and metastasize to new body sites. Examples of different types of cancer suitable for treatment using the present invention include, but are not limited to, lung cancer, breast cancer, bladder cancer, thyroid cancer, liver cancer, pleural cancer, pancreatic cancer, ovarian cancer, cervical cancer, testicular cancer, colon cancer, B-cell lymphoma, non-Hodgkin's lymphoma, Burkitt's lymphoma, fibrosarcoma, neuroblastoma, glioma, melanoma, monocytic leukemia, myelogenous leukemia, meningioma, schwannoma, and oligodendroglioma.

The term "central nervous system disease or disorder" refers to a disease or disorder that affects any component of the brain (e.g., the cerebral hemispheres, diencephalon, brain stem, cerebellum), spinal cord, or a combination thereof. Examples of different types of central nervous system diseases or disorders suitable for treatment using the present invention include, but are not limited to, brain diseases such as akinetic mutism, amblyopia, amnesia, auditory diseases, basal ganglia diseases, brain abscess, brain damage, brain death, metabolic brain diseases, brain edema, brain injuries, brain neoplasms, cerebellar diseases, cerebrovascular disorders, dementia, diffuse cerebral sclerosis of Schilder, encephalitis, encephalomalacia, epilepsy, headache disorders, hydrocephalus, hypothalamic diseases, intracranial hypertension, intracranial hypotension, Kluver-Bucy syndrome, neuroaxonal dystrophies, subdural effusion, and thalamic diseases; central nervous system infections such as bacterial, fungal, parasitic, and viral infections, subdural empyema, encephalomyelitis, epidural abscess, meningitis, meningoencephalitis, myelitis, perimeningeal infections, and prion diseases; movement disorders such as Angelman syndrome, choreatic disorders, dystonic disorders, essential tremors, Hallervorden-Spatz syndrome, hepatolenticular degeneration, multiple system atrophy, Parkinsonian disorders, progressive supranuclear palsy, and tic disorders; and spinal cord diseases such as amyotrophic lateral sclerosis, spinal muscular atrophy, poliomyelitis, spinal cord compression, spinal cord injuries, spinal cord neoplasms, spinal cord vascular diseases, spinocerebellar degenerations, Stiff-Person syndrome, syringomyelia, and tabes dorsalis. Preferably, the central nervous system disease or disorder is a stroke, traumatic brain injury, epilepsy, brain edema, tissue hypoxia-ischemia, or ischemia-reperfusion injury in the brain or myocardium.

The term "ischemia" refers to an interruption or decrease in blood supply to a bodily tissue or organ caused by constriction or obstruction of blood vessels, leading to oxygen deprivation of the tissue or organ, which can result in tissue or organ damage. The term "myocardial ischemia" refers to a condition characterized by a blockage or constriction of one or more of the coronary arteries that can occur with atherosclerotic plaque occlusion or rupture. The term "reperfusion" refers to the restoration of blood flow to a bodily tissue or organ that has had its blood supply cut off, leading to reoxygenation of the tissue or organ, such as, e.g., after a heart attack. The term "ischemia-reperfusion injury" refers to tissue or organ damage caused by oxygen deprivation followed by reoxygenation of the tissue or organ. In certain instances, reperfilsion with subsequent reoxygenation of the tissue or organ causes additional tissue or organ injury such as, e.g., oxidative stress.

The term "peptidase" refers to any of various enzymes that catalyze the degradation of peptides, polypeptides, and proteins by hydrolyzing at least one of their peptide bonds. Suitable peptidases for use in the present invention include, but are not limited to, endopeptidases (e.g., serine proteases and metalloproteinases) and exopeptidases (e.g., carboxypeptidases and aminopeptidases). In particular, peptidases such as opioid neuropeptide peptidases (e.g., enkephalinases), metalloproteinases (e.g., matrix metalloproteinases, disintegrin-metalloproteinases (ADAMs)), plasminogen activators, cathepsins, calpains, and caspases are suitable for use in the present invention.

The terms "enkephalinase" and "endopeptidase 24.11" are used interchangeably herein to refer to a cell surface, zinc-containing metallopeptidase that is present in brain, endothelial cells, liver, and lung, and is abundant in the brush border membrane of the kidney proximal tubules. The peptidase contains an arginine in the active site that interacts with the carboxyl-terminal carboxylate of peptide substrates. Peptidase activity is specifically directed toward the selective cleavage on the amino side of hydrophobic residues.

The term "matrix metalloproteinase" refers to members of a family of proteolytic enzymes that have a zinc ion at their active sites and can degrade collagen, elastin, and other components of the extracellular matrix. Preferably, the matrix metalloproteinase is MMP-2 or MMP-9. The substrate specificity of MMP-2 is collagen (e.g., types IV, V, VII, and X), elastin, type I gelatin, and peptide fragments thereof containing the MMP-2 cleavage site. Peptide sequences that are selectively cleaved by MMP-2 or MMP-9 are described in Chen et al., *J. Biol. Chem.*, 277:4485-4491 (2002).

The term "selectively cleaved" refers to the hydrolysis of a peptide bond by a protease upon recognition of a specific amino acid residue or amino acid sequence in a peptide, polypeptide, or protein. For example, trypsin selectively cleaves peptide bonds on the carboxyl-terminal side of lysine (K) and arginine (R) amino acid residues. Chymotrypsin selectively cleaves peptide bonds on the carboxyl-terminal side of phenylalanine (F), tryptophan (W), and tyrosine (Y) residues. Enkephalinase selectively cleaves peptide bonds on the amino-terminal side of hydrophobic residues.

The term "therapeutically effective amount" refers to the amount of an amiloride conjugate of the present invention that is capable of achieving a therapeutic effect in a subject in need thereof. For example, a therapeutically effective amount of an amiloride conjugate of the present invention can be the amount that is capable of treating cancer, treating a central nervous system disease or disorder, or preventing or reducing ischemia-reperfusion injury.

As used herein, "administering" means oral administration, administration as a suppository, topical contact, intravenous, intraperitoneal, intramuscular, intralesional, intraarterial, intrathecal, intranasal or subcutaneous administration, or the implantation of a slow-release device e.g., a mini-osmotic pump, to a subject. Adminsitration is by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

II. General Overview

The present invention provides novel amiloride conjugates that advantageously display high specificity and potency, are low in toxicity, and traverse the blood brain barrier (BBB) into the central nervous system, as well as methods of use thereof.

Amiloride is an FDA-approved diuretic that inhibits tumor cell proliferation and exhibits cytotoxic effects on tumor cells at high concentrations. However, due to the hydrophobic nature of amiloride (i.e., high toxicity associated with significant intracellular accumulation), its low potency for producing cytotoxic effects (i.e., high ($\geq$500 µM) concentrations required), and its inability to cross the blood brain barrier (BBB), amiloride is unsuitable as an effective drug for treating cancers such as gliomas. By contrast, the present invention provides novel amino acid and peptide conjugates of amiloride that are potent and effective NHE1 and/or NCX inhibitors, display cytotoxic and/or anitproliferative effects on tumor cells such as glioma cells, are hydrophilic (i.e., low toxicity), are selectively cleaved by brain-specific, tumor-specific, or tissue injury-induced peptidases, and are able to cross the BBB.

In particular, the amiloride conjugates of the present invention have the following advantages: (1) amiloride-peptide conjugates with peptidase cleavage sites are not only capable of traversing the BBB, but upon cleavage by brain- or tumor-specific peptidases in the central nervous system, release hydrophilic proteolytic products (e.g., C2am-Gly, C5am-Gly) that act at the tumor cell surface, thus minimizing toxic side effects; and (2) the conjugates kill tumor cell populations residing in hypoxic-ischemic tumor microenvironments (i.e., tumor cells with little or no blood supply) that are normally resistant to conventional chemotherapy or radiotherapy. These unique features make the amiloride conjugates of the present invention particularly useful therapeutic agents for the treatment of cancer (e.g., glioma, breast cancer) as well as other diseases and disorders such as central nervous system disorders (e.g., traumatic brain injury, seizure), stroke, cardiac arrthymia, etc.

The novel amiloride conjugates of the present invention are also useful as therapeutic agents for the prevention or reduction of ischemia-reperfusion injury, e.g., to brain or heart tissue. Although inhibition of $Na^+$—$H^+$ exchangers such as NHE1 are important in reducing tissue damage during ischemia-reperfusion injury, currently available pharmacological inhibitors of NHE1 such as amiloride are unable to access the ischemic tissue due to severely compromised tissue perfusion. The present invention overcomes this limitation by advantageously providing a biologically inactive NHE1 inhibitor prodrug (e.g., an amiloride-peptide conjugate) that is administered prior to the onset of ischemia. During an ischemic event, peptidases selectively expressed or activated by the ischemic tissue activate the prodrug, thereby preventing or reducing ischemia-reperfusion injury in the affected tissue. For example, the peptidases can selectively release hydrophilic proteolytic products (e.g., C2am-Gly, C5am-Gly) from the prodrug that act at the cell surface of the ischemic tissue, thus minimizing toxic side effects. The prodrugs described herein are particularly useful for preventing or reducing ischemia-reperfusion injury in brain or heart tissue.

III. Description of the Embodiments

In one aspect, the present invention provides a conjugate having the formula:

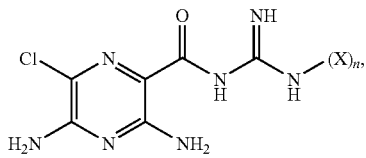

wherein X is n independently selected amino acids and n is an integer greater than or equal to 1.

The amino acid (i.e., when n equals 1) or peptide (i.e., when n is greater than 1) is conjugated to the C(2) position of amiloride via an amide bond. When n is greater than 1, X is a peptide comprising a combination of independently selected amino acids or a polymer of one amino acid. In one embodiment, the amino acids are selected from the group consisting of α-amino acids, β-amino acids, γ-amino acids, N-methyl amino acids, N-substituted glycines, and combinations thereof. In another embodiment, the amino acids are selected from the group consisting of L-amino acids, D-amino acids, and combinations thereof. In yet another embodiment, the α-amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, hydroxyproline, tyrosine, and combinations thereof.

In a preferred embodiment, the amino acid or peptide is connected to the C(2) position of amiloride via a linker. Suitable linkers include glycine and a diamine. Preferably, the linker is glycine. In another preferred embodiment, n equals 1 and the amino acid is glycine, phenylalanine, (2,4-dichloro)-phenylalanine, serine, or O-benzyl serine. In still yet another embodiment, X is a peptide and n is between 2 and 50, preferably between 2 and 25, more preferably between 2 and 10, and most preferably between 2 and 8. In yet another preferred embodiment, the peptide contains one or more amino acids selected from the group consisting of (2,4-dichloro)-phenylalanine, O-benzyl serine, and combinations thereof.

In a further embodiment, the peptide comprises a sequence having at least two glycine residues. Preferably, the peptide is selectively cleaved by a peptidase, such as a brain-specific or tumor-specific peptidase, or an enzyme activated during tissue injury. In certain instances, the peptidase is an endogenous peptidase. Alternatively, the peptidase can be an exogenous peptidase. In one embodiment, the peptide is selectively cleaved by an enkephalinase. For example, the peptide can contain an amino acid sequence recognized by an enkephalinase or a related endopeptidase such as a sequence comprising an enkephalin, a derivative thereof, or an analog thereof (e.g., [Leu]⁵-enkephalin amide). In another embodiment, the peptide is selectively cleaved by a metalloproteinase such as a matrix metalloproteinase (e.g., MMP-2, MMP-9) or a disintegrin-metalloproteinase (e.g., ADAM). In yet another embodiment, the peptide is selectively cleaved by a plasminogen activator, a cathepsin, a calpain, or a caspase. In still yet another embodiment, the peptide is selected from the group consisting of Gly-Gly-Gly-Gly-Phe-Leu (SEQ ID NO:1), Tyr-D-Ala-Gly-Phe-Gly-NH₂ (SEQ ID NO:2), Glu-Ser-Leu-Ala-Tyr-Tyr-Thr-Ala-Gly-NH₂ (SEQ ID NO:3), Arg-Ser-Leu-Ser-Arg-Leu-Thr-Ala-Gly-NH₂ (SEQ ID NO:4), Glu-Ser-Leu-D-Ala-Tyr-Tyr-Thr-Ala-Gly-NH₂ (SEQ ID NO:5), Arg-Ser-Leu-Ser-Arg-D-Leu-Thr-Ala-Gly-NH₂ (SEQ ID NO:6), and Arg-Ser-Leu-Ser-Arg-Leu-Thr-Ala-Gly-Gly-NH₂ (SEQ ID NO:7). In a preferred embodiment, the peptide is Gly-Gly-Gly-Gly-Phe-Leu (SEQ ID NO:1).

In a particularly preferred embodiment, the conjugate has the formula:

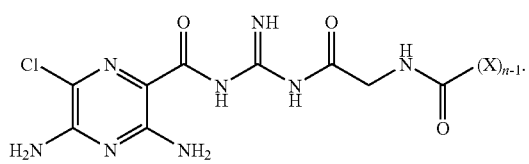

In another particularly preferred embodiment, the conjugate has the formula:

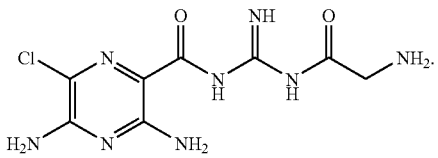

In another aspect, the present invention provides a conjugate having the formula:

wherein X is n independently selected amino acids and n is an integer greater than or equal to 1.

The amino acid (i.e., when n equals 1) or peptide (i.e., when n is greater than 1) is conjugated to the C(5) position of amiloride via an amine bond. When n is greater than 1, X is a peptide comprising a combination of independently selected amino acids or a polymer of one amino acid. In one embodiment, the amino acids are selected from the group consisting of those amino acids described above. In a preferred embodiment, the amino acid or peptide is connected to the C(5) position of amiloride via a linker. Suitable linkers are described above. In another preferred embodiment, n equals 1 and the amino acid is glycine, phenylalanine, (2,4-dichloro)-phenylalanine, serine, or O-benzyl serine. In another embodiment, X is a peptide and n is between 2 and 50, preferably between 2 and 25, more preferably between 2 and 10, and most preferably between 2 and 8. In yet another preferred embodiment, the peptide contains one or more amino acids selected from the group consisting of (2,4-dichloro)-phenylalanine, O-benzyl serine, and combinations thereof.

In a further embodiment, the peptide comprises a sequence having at least two glycine residues. Preferably, the peptide is selectively cleaved by a peptidase, such as a brain-specific or tumor-specific peptidase, or an enzyme activated during tissue injury. Suitable peptidases and peptide sequences are described above.

In a particularly preferred embodiment, the conjugate has the formula:

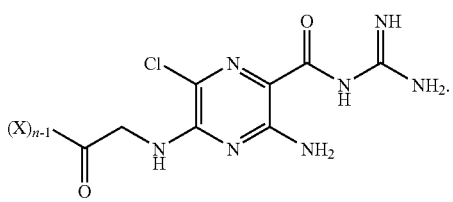

In another particularly preferred embodiment, the conjugate has the formula:

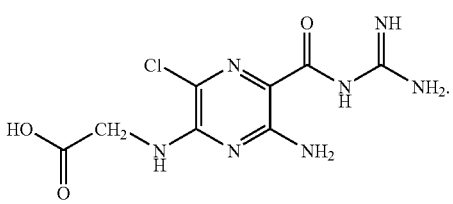

In yet another aspect, the present invention provides a conjugate having the formula:

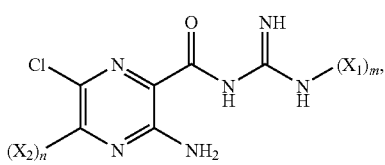

wherein $X_1$ and $X_2$ are m and n independently selected amino acids, respectively, and m and n are independently selected integers greater than or equal to 1.

The $X_1$ amino acid (i.e., when m equals 1) or peptide (i.e., when m is greater than 1) is conjugated to the C(2) position of amiloride via an amide bond and the $X_2$ amino acid (i.e., when n equals 1) or peptide (i.e., when n is greater than 1) is conjugated to the C(5) position of amiloride via an amine bond. When m and n are both greater than 1, $X_1$ and $X_2$ are either identical or different peptides comprising a combination of independently selected amino acids or a polymer of one amino acid. In one embodiment, the amino acids are selected from the group consisting of those amino acids described above. In a preferred embodiment, the amino acid or peptide is connected to the C(2) and/or C(5) position of amiloride via a linker. Suitable linkers are described above. In another preferred embodiment, m and/or n equals 1 and the amino acid is glycine, phenylalanine, (2,4-dichloro)-phenylalanine, serine, and/or O-benzyl serine. In still yet another embodiment, $X_1$ and $X_2$ are peptides and m and n are each independently between 2 and 50, preferably between 2 and 25, more preferably between 2 and 10, and most preferably between 2 and 8. In yet another preferred embodiment, the peptide contains one or more amino acids selected from the group consisting of (2,4-dichloro)-phenylalanine, O-benzyl serine, and combinations thereof.

In a further embodiment, at least one of the peptides comprises a sequence having at least two glycine residues. Preferably, the peptide is selectively cleaved by a peptidase, such as a brain-specific or tumor-specific peptidase, or an enzyme activated during tissue injury. Suitable peptidases and peptide sequences are described above.

In a particularly preferred embodiment, the conjugate has the formula:

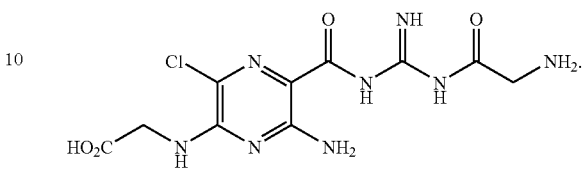

In still yet another aspect, the present invention provides a conjugate having the formula:

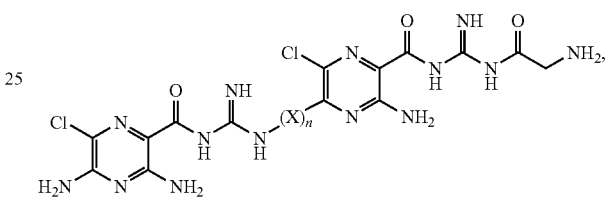

wherein X is n independently selected amino acids and n is an integer greater than or equal to 1.

The amino acid (i.e., when n equals 1) or peptide (i.e., when n is greater than 1) is conjugated to the C(2) position of one amiloride molecule via an amide bond and to the C(5) position of a second amiloride molecule via an amine bond. When n is greater than 1, X is a peptide comprising a combination of independently selected amino acids or a polymer of one amino acid. In one embodiment, the amino acids are selected from the group consisting of those amino acids described above. In a preferred embodiment, the amino acid or peptide is connected to the C(2) position of one amiloride molecule via one linker and to the C(5) position of a second amiloride molecule via another linker. Suitable linkers are described above. In another preferred embodiment, n equals 1 and the amino acid is glycine, phenylalanine, (2,4-dichloro)-phenylalanine, serine, or O-benzyl serine. In still yet another embodiment, X is a peptide and n is between 2 and 50, preferably between 2 and 25, more preferably between 2 and 10, and most preferably between 2 and 8. In yet another preferred embodiment, the peptide contains one or more amino acids selected from the group consisting of (2,4-dichloro)-phenylalanine, O-benzyl serine, and combinations thereof.

In a further embodiment, the peptide comprises a sequence having at least two glycine residues. Preferably, the peptide is selectively cleaved by a peptidase, such as a brain-specific or tumor-specific peptidase, or an enzyme activated during tissue injury. Suitable peptidases and peptide sequences are described above.

In a particularly preferred embodiment, the conjugate has the formula:

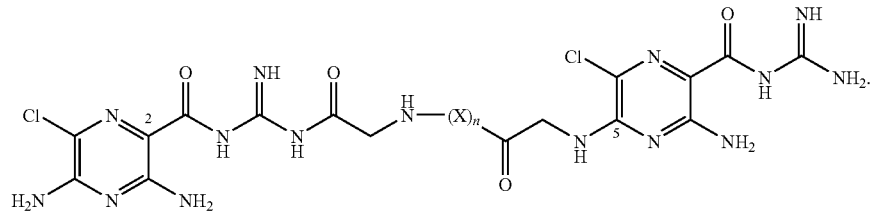

In a further aspect, the present invention provides a method for treating cancer in a subject in need thereof, the method comprising:
administering to the subject a therapeutically effective amount of a conjugate having the formula:

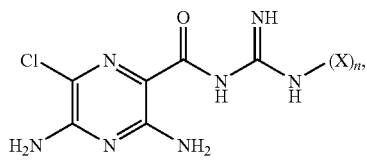

wherein X is n independently selected amino acids and n is an integer greater than or equal to 1.

In one embodiment, the cancer is lung cancer, breast cancer, bladder cancer, thyroid cancer, liver cancer, pleural cancer, pancreatic cancer, ovarian cancer, cervical cancer, testicular cancer, colon cancer, B-cell lymphoma, non-Hodgkin's lymphoma, Burkitt's lymphoma, fibrosarcoma, neuroblastoma, glioma, melanoma, monocytic leukemia, myelogenous leukemia, meningioma, schwannoma, oligodendroglioma, and combinations thereof. Preferably, the cancer is a glioma. In another embodiment, the cancer is treated by killing cancer cells, inhibiting the proliferation of cancer cells, or a combination thereof.

In yet another embodiment, X is a peptide and n is greater than 1, and X is selectively cleaved by a peptidase. Preferably, n is between 2 and 25, more preferably between 2 and 10, and most preferably between 2 and 8. In certain instances, the method further comprises co-administering to the subject an agent (e.g., small organic molecule, peptide, protein, polypeptide, peptidase, oligosaccharide, etc.) that activates an endogenous peptidase (e.g., a tumor-specific peptidase) which in turn selectively cleaves the peptide. See, e.g., Levicar et al., *Acta Neurochir. (Wien)*, 145:825-838 (2003); Lah et al., *Int. J. Biol. Markers*, 15:90-93 (2000). Alternatively, the method further comprises co-administering to the subject a peptidase that selectively cleaves the peptide. One of skill in the art will appreciate that administration of the agent or peptidase may occur either at the same time as the administration of the amiloride conjugate, or may be administered sequentially in a predetermined order.

In a preferred embodiment, the co-administered agent or peptidase is present in an amount effective to increase the release of an active (i.e., bioactive) proteolytic product from the conjugate relative to the amount of release of the proteolytic product in the absence of the agent or peptidase. Preferably, the proteolytic product is amiloride or any enzymatic cleavage product such as a C2am-amino acid cleavage product or a C2am-peptide cleavage product. In a particularly preferred embodiment, the proteolytic product is C2am-Gly.

In certain instances, the co-administered agent activates an endogenous peptidase such as, for example, an opioid neuropeptide peptidase (e.g., enkephalinase), a metalloproteinase (e.g., matrix metalloproteinase, disintegrin-metalloproteinase (ADAM)), a plasminogen activator, a cathepsin, a calpain, a caspase, or combinations thereof. Alternatively, one or more of the above-described peptidases is co-administered to the subject.

In another aspect, the present invention provides a method for treating cancer in a subject in need thereof, the method comprising:
administering to the subject a therapeutically effective amount of a conjugate having the formula:

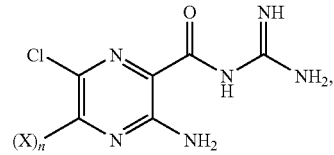

wherein X is n independently selected amino acids and n is an integer greater than or equal to 1.

In one embodiment, the cancer is any of the above-described cancers. In another embodiment, X is a peptide and n is greater than 1, and X is selectively cleaved by a peptidase. As described above, the method can further comprise co-administering to the subject either an agent that activates an endogenous peptidase which in turn selectively cleaves the peptide, or, alternatively, a peptidase that selectively cleaves the peptide. In a preferred embodiment, the co-administered agent or peptidase is present in an amount effective to increase the release of an active (i.e., bioactive) proteolytic product from the conjugate relative to the amount of release of the proteolytic product in the absence of the agent or peptidase. Preferably, the proteolytic product is amiloride or any enzymatic cleavage product such as a C5am-amino acid cleavage product or a C5am-peptide cleavage product. In a particularly preferred embodiment, the proteolytic product is C5am-Gly. In certain instances, the co-administered agent activates one or more of the above-described peptidases, or, alternatively, one or more of the above-described peptidases is co-administered to the subject.

In yet another aspect, the present invention provides a method for treating cancer in a subject in need thereof, the method comprising:

administering to the subject a therapeutically effective amount of a conjugate having the formula:

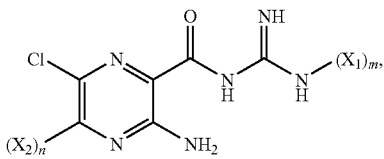

wherein $X_1$ and $X_2$ are m and n independently selected amino acids, respectively, and m and n are independently selected integers greater than or equal to 1.

In one embodiment, the cancer is any of the above-described cancers. In another embodiment, at least one of $X_1$ and $X_2$ is a peptide, the peptide has greater than one amino acid (i.e., m and/or n are independently greater than 1), and the peptide is selectively cleaved by a peptidase. In certain instances, $X_1$ and $X_2$ are different peptides that are selectively cleaved by different peptidases. As described above, the method can further comprise co-administering to the subject either an agent that activates an endogenous peptidase which in turn selectively cleaves at least one of the peptides, or, alternatively, a peptidase that selectively cleaves at least one of the peptides. In a preferred embodiment, the co-administered agent or peptidase is present in an amount effective to increase the release of an active (i.e., bioactive) proteolytic product from the conjugate relative to the amount of release of the proteolytic product in the absence of the agent or peptidase. Preferably, the proteolytic product is amiloride or any enzymatic cleavage product such as a C2,5am-amino acid cleavage product or a C2,5am-peptide cleavage product. In a particularly preferred embodiment, the proteolytic product is C2,5am-(Gly)$_2$. In certain instances, the co-administered agent activates one or more of the above-described peptidases, or, alternatively, one or more of the above-described peptidases is co-administered to the subject.

In still yet another aspect, the present invention provides a method for treating cancer in a subject in need thereof, the method comprising:

administering to the subject a therapeutically effective amount of a conjugate having the formula:

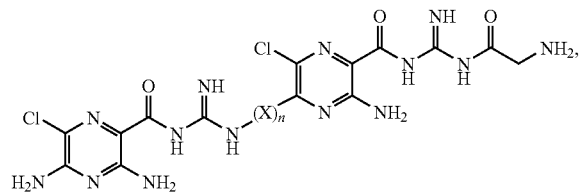

wherein X is n independently selected amino acids and n is an integer greater than or equal to 1.

In one embodiment, the cancer is any of the above-described cancers. In another embodiment, X is a peptide and n is greater than 1, and X is selectively cleaved by a peptidase. As described above, the method can further comprise co-administering to the subject either an agent that activates an endogenous peptidase which in turn selectively cleaves the peptide, or, alternatively, a peptidase that selectively cleaves the peptide. In a preferred embodiment, the co-administered agent or peptidase is present in an amount effective to increase the release of an active (i.e., bioactive) proteolytic product from the conjugate relative to the amount of release of the proteolytic product in the absence of the agent or peptidase. Preferably, the proteolytic product is amiloride or any enzymatic cleavage product such as a C2am-amino acid cleavage product (e.g., C2am-Gly), a C5am-amino acid cleavage product (e.g., C5am-Gly), a C2am-peptide cleavage product, a C5am-peptide cleavage product, or a combination thereof. In a particularly preferred embodiment, the proteolytic product is a combination of C2am-Gly and C5am-Gly. In certain instances, the co-administered agent activates one or more of the above-described peptidases, or, alternatively, one or more of the above-described peptidases is co-administered to the subject.

In a further aspect, the present invention provides a method for treating a central nervous system disease or disorder in a subject in need thereof, the method comprising:

administering to the subject a therapeutically effective amount of a conjugate having the formula:

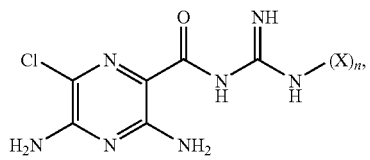

wherein X is a peptide comprising n independently selected amino acids and n is an integer greater than 1, and wherein the peptide contains a cleavage site recognized (i.e., selectively cleaved) by a peptidase in the central nervous system.

In one embodiment, the central nervous system disease or disorder is any brain disease, central nervous system infection, movement disorder, or spinal cord disease described above. Preferably, the central nervous system disease or disorder is brain edema, traumatic brain injury, tissue hypoxia-ischemia, ischemia-reperfusion injury, epilepsy, brain tumor (e.g., glioma), or stroke.

In another embodiment, the method further comprises co-administering to the subject an agent (e.g., peptidase) that activates the central nervous system peptidase. In certain instances, the conjugate is a prodrug that releases an active (i.e., bioactive) proteolytic product upon selective cleavage by the central nervous system peptidase. In a preferred embodiment, the prodrug is capable of crossing the blood brain barrier (BBB). Preferably, the proteolytic product is amiloride or any enzymatic cleavage product such as a C2am-amino acid cleavage product or a C2am-peptide cleavage product. In a particularly preferred embodiment, the proteolytic product is C2am-Gly.

In yet another embodiment, the peptide is a substrate for a central nervous system peptidase such as a brain-specific peptidase, a tumor-specific peptidase, a brain injury-activated calpain, a brain injury-activated caspase, a nervous system-specific peptidase, or 20 combinations thereof. In certain instances, the central nervous system peptidase is selected from the group consisting of an enkephalinase, a metalloproteinase such as MMP-2 or MMP-9, and combinations thereof. Preferably, the peptide is selected from the group consisting of Gly-Gly-Gly-Gly-Phe-Leu (SEQ ID NO:1), Tyr-D-Ala-Gly-Phe-Gly-NH$_2$ (SEQ ID NO:2), Glu-Ser-Leu-Ala-Tyr-Tyr-Thr-Ala-Gly-NH$_2$ (SEQ ID NO:3), Arg-Ser-Leu-Ser-Arg-Leu-Thr-Ala-Gly-NH$_2$ (SEQ ID NO:4), Glu-Ser-Leu-D-Ala-Tyr-Tyr-Thr-Ala-Gly-NH$_2$ (SEQ ID NO:5), Arg-Ser- Leu-Ser-Arg-D-Leu-Thr-Ala-Gly-NH$_2$ (SEQ ID NO:6), and Arg-Ser-Leu-Ser-Arg-Leu-Thr-Ala-Gly-Gly-NH$_2$ (SEQ ID NO:7).

In another aspect, the present invention provides a method for treating a central nervous system disease or disorder in a subject in need thereof, the method comprising:

administering to the subject a therapeutically effective amount of a conjugate having the formula:

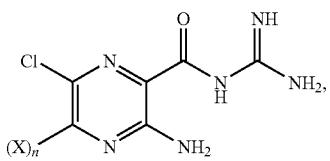

wherein X is a peptide comprising n independently selected amino acids and n is an integer greater than 1, and wherein the peptide contains a cleavage site recognized (i.e., selectively cleaved) by a peptidase in the central nervous system.

In one embodiment, the central nervous system disease or disorder is any brain disease, central nervous system infection, movement disorder, or spinal cord disease described above. In another embodiment, the method further comprises co-administering to the subject an agent (e.g., peptidase) that activates the central nervous system peptidase. In certain instances, the conjugate is a prodrug that releases an active (i.e., bioactive) proteolytic product upon selective cleavage by the central nervous system peptidase. In a preferred embodiment, the prodrug is capable of crossing the BBB. Preferably, the proteolytic product is amiloride or any enzymatic cleavage product such as a C5am-amino acid cleavage product or a C5am-peptide cleavage product. In a particularly preferred embodiment, the proteolytic product is C5am-Gly. Suitable central nervous system peptidases and peptide sequences are described above.

In yet another aspect, the present invention provides a method for treating a central nervous system disease or disorder in a subject in need thereof, the method comprising:

administering to the subject a therapeutically effective amount of a conjugate having the formula:

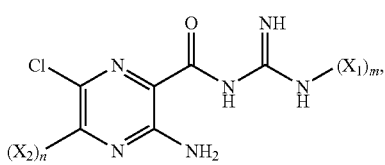

wherein X$_1$ and X$_2$ are peptides comprising m and n independently selected amino acids, respectively, and m and n are independently selected integers greater than 1, and wherein the peptide contains a cleavage site recognized (i.e., selectively cleaved) by a peptidase in the central nervous system.

In one embodiment, the central nervous system disease or disorder is any brain disease, central nervous system infection, movement disorder, or spinal cord disease described above. In another embodiment, the method further comprises co-administering to the subject an agent (e.g., peptidase) that activates the central nervous system peptidase. In certain instances, the conjugate is a prodrug that releases an active (i.e., bioactive) proteolytic product upon selective cleavage by the central nervous system peptidase. In a preferred embodiment, the prodrug is capable of crossing the BBB. Preferably, the proteolytic product is amiloride or any enzymatic cleavage product such as a C2,5am-amino acid cleavage product or a C2,5am-peptide cleavage product. In a particularly preferred embodiment, the proteolytic product is C2,5am-(Gly)$_2$. Suitable central nervous system peptidases and peptide sequences are described above.

In still yet another aspect, the present invention provides a method for treating a central nervous system disease or disorder in a subject in need thereof, the method comprising:

administering to the subject a therapeutically effective amount of a conjugate having the formula:

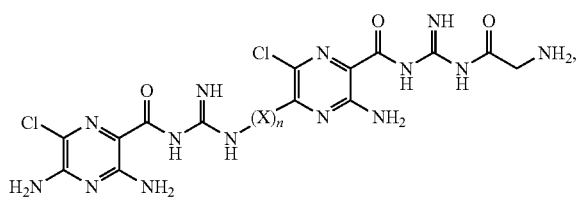

wherein X is a peptide comprising n independently selected amino acids and n is an integer greater than 1, and wherein the peptide contains a cleavage site recognized (i.e., selectively cleaved) by a peptidase in the central nervous system.

In one embodiment, the central nervous system disease or disorder is any brain disease, central nervous system infection, movement disorder, or spinal cord disease described above. In another embodiment, the method further comprises co-administering to the subject an agent (e.g., peptidase) that activates the central nervous system peptidase. In certain instances, the conjugate is a prodrug that releases one or more active (i.e., bioactive) proteolytic products upon selective cleavage by the central nervous system peptidase. In a preferred embodiment, the prodrug is capable of crossing the BBB. Preferably, the proteolytic product is amiloride or any enzymatic cleavage product such as a C2am-amino acid cleavage product (e.g., C2am-Gly), a C5am-amino acid cleavage product (e.g., C5am-Gly), a C2am-peptide cleavage product, a C5am-peptide cleavage product, or a combination thereof. In a particularly preferred embodiment, the proteolytic product is a combination of C2am-Gly and C5am-Gly. Suitable central nervous system peptidases and peptide sequences are described above.

In a further aspect, the present invention provides a method for preventing or reducing ischemia-reperfusion injury in a subject in need thereof, the method comprising:

administering to the subject prior to the onset of ischemia a therapeutically effective amount of a conjugate having the formula:

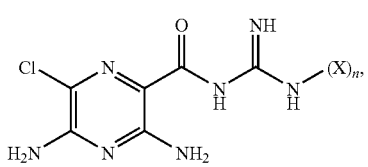

wherein X is a peptide comprising n independently selected amino acids and n is an integer greater than 1, and wherein the peptide contains a cleavage site recognized (i.e., selectively cleaved) by a peptidase in the ischemic tissue.

In one embodiment, the subject is at risk of a first or subsequent ischemic event or requires a surgical procedure that increases the risk of ischemia-reperfusion injury. Examples include individuals with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (e.g., a myocardial ischemic event such as a myocardial infarction or a neurovascular ischemic event such as a cerebrovascular accident). Risk factors for stroke (or a subset of these risk factors) that can demonstrate a subject's risk for ischemia of brain tissue include, without limitation, hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. See, Ingall, "Preventing ischemic stroke: current approaches to primary and secondary prevention," *Postgrad. Med.*, 107(6):34-50 (2000). Further, complications of untreated infectious diarrhea in the elderly can include myocardial, renal, cerebrovascular, and intestinal ischemia. See, Slotwiner-Nie & Brandt, "Infectious diarrhea in the elderly," *Gastroenterol, Clin. N. Am.*, 30(3):625-635 (2001). Alternatively, subjects could be selected based on risk factors for ischemic bowel, kidney, or liver disease. For example, treatment would be initiated in elderly subjects at risk of hypotensive episodes (e.g., surgical blood loss). Other conditions that may result in ischemia include cerebral arteriovenous malformation.

An at-risk subject can be selected by physical testing or eliciting the potential subject's medical history to determine whether the subject has any indications of risk for an ischemic event. In certain instances, the subject selected for treatment is at risk of future ischemia, but has no present evidence of ischemia (e.g., crushing substernal chest pain or arm pain, shortness of breath, diaphoresis, etc.). The amiloride conjugates of the present invention can also be administered prior to procedures in which ischemia may occur, e.g., prior to angioplasty or surgery such as coronary artery bypass graft surgery. As such, administration of the amiloride conjugates of the present invention is useful in preventing or reducing injury from ischemia-reperfusion in the heart, brain, liver, gut, kidney, bowel, or in any other tissue or organ.

In another embodiment, the method further comprises co-administering to the subject an agent (e.g., peptidase) that activates the ischemic tissue peptidase. In certain instances, the conjugate is a prodrug that releases an active (i.e., bioactive) proteolytic product upon selective cleavage by the ischemic tissue peptidase. Preferably, the proteolytic product is amiloride or any enzymatic cleavage product such as a C2am-amino acid cleavage product or a C2am-peptide cleavage product. In a particularly preferred embodiment, the proteolytic product is C2am-Gly.

In yet another embodiment, the peptide is a substrate for an ischemic tissue peptidase such as, for example, an opioid neuropeptide peptidase (e.g., enkephalinase), a metalloproteinase (e.g., matrix metalloproteinase, disintegrin-metalloproteinase (ADAM)), a plasminogen activator, a cathepsin, a calpain, a caspase, or combinations thereof. Preferably, the peptide is selected from the group consisting of Gly-Gly-Gly-Gly-Phe-Leu-OH, Tyr-D-Ala-Gly-Phe-Gly-NH$_2$, Glu-Ser-Leu-Ala-Tyr-Tyr-Thr-Ala-Gly-NH$_2$, Arg-Ser-Leu-Ser-Arg-Leu-Thr-Ala-Gly-NH$_2$, Glu-Ser-Leu-D-Ala-Tyr-Tyr-Thr-Ala-Gly-NH$_2$, Arg-Ser-Leu-Ser-Arg-D-Leu-Thr-Ala-Gly-NH$_2$, and Arg-Ser-Leu-Ser-Arg-Leu-Thr-Ala-Gly-Gly-NH$_2$.

In another aspect, the present invention provides a method for preventing or reducing ischemia-reperfusion injury in a subject in need thereof, the method comprising:
  administering to the subject prior to the onset of ischemia a therapeutically effective amount of a conjugate having the formula:

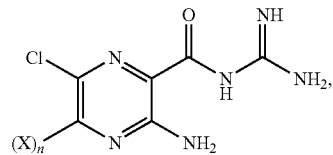

wherein X is a peptide comprising n independently selected amino acids and n is an integer greater than 1, and wherein the peptide contains a cleavage site recognized (i.e., selectively cleaved) by a peptidase in the ischemic tissue.

In one embodiment, the subject is at risk of a first or subsequent ischemic event or requires a surgical procedure that increases the risk of ischemia-reperfusion injury. In another embodiment, the method further comprises co-administering to the subject an agent (e.g., peptidase) that activates the ischemic tissue peptidase. In certain instances, the conjugate is a prodrug that releases an active (i.e., bioactive) proteolytic product upon selective cleavage by the ischemic tissue peptidase. Preferably, the proteolytic product is amiloride or any enzymatic cleavage product such as a C5am-amino acid cleavage product or a C5am-peptide cleavage product. In a particularly preferred embodiment, the proteolytic product is C5am-Gly. Suitable ischemic tissue peptidases and peptide sequences are described above.

In yet another aspect, the present invention provides a method for preventing or reducing ischemia-reperfusion injury in a subject in need thereof, the method comprising:
  administering to the subject prior to the onset of ischemia a therapeutically effective amount of a conjugate having the formula:

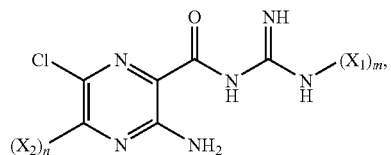

wherein $X_1$ and $X_2$ are peptides comprising m and n independently selected amino acids, respectively, and m and n are independently selected integers greater than 1, and wherein the peptide contains a cleavage site recognized (i.e., selectively cleaved) by a peptidase in the ischemic tissue.

In one embodiment, the subject is at risk of a first or subsequent ischemic event or requires a surgical procedure that increases the risk of ischemia-reperfusion injury. In another embodiment, the method further comprises co-administering to the subject an agent (e.g., peptidase) that activates the ischemic tissue peptidase. In certain instances, the conjugate is a prodrug that releases an active (i.e., bioactive) proteolytic product upon selective cleavage by the ischemic tissue peptidase. Preferably, the proteolytic product is amiloride or any enzymatic cleavage product such as a C2,5am-amino acid cleavage product or a C2,5am-peptide cleavage product. In a particularly preferred embodiment, the proteolytic product is C2,5am-(Gly)$_2$. Suitable ischemic tissue peptidases and peptide sequences are described above.

In still yet another aspect, the present invention provides a method for preventing or reducing ischemia-reperfusion injury in a subject in need thereof, the method comprising:

administering to the subject prior to the onset of ischemia a therapeutically effective amount of a conjugate having the formula:

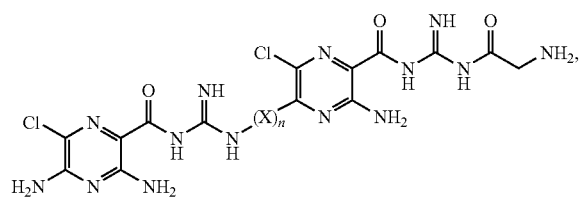

wherein X is a peptide comprising n independently selected amino acids and n is an integer greater than 1, and wherein the peptide contains a cleavage site recognized (i.e., selectively cleaved) by a peptidase in the ischemic tissue.

In one embodiment, the subject is at risk of a first or subsequent ischemic event or requires a surgical procedure that increases the risk of ischemia-reperfusion injury. In another embodiment, the method further comprises co-administering to the subject an agent (e.g., peptidase) that activates the ischemic tissue peptidase. In certain instances, the conjugate is a prodrug that releases an active (i.e., bioactive) proteolytic product upon selective cleavage by the ischemic tissue peptidase. Preferably, the proteolytic product is amiloride or any enzymatic cleavage product such as a C2am-amino acid cleavage product (e.g., C2am-Gly), a C5am-amino acid cleavage product (e.g., C5am-Gly), a C2am-peptide cleavage product, a C5am-peptide cleavage product, or a combination thereof. In a particularly preferred embodiment, the proteolytic product is a combination of C2am-Gly and C5am-Gly. Suitable ischemic tissue peptidases and peptide sequences are described above.

In a further aspect, the present invention provides a kit for the treatment of a central nervous system disease or disorder, the kit comprising:

(a) a container holding a conjugate having the formula:

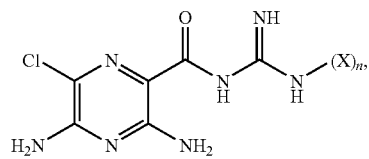

wherein X is a peptide comprising n independently selected amino acids, n is an integer greater than 1, and the peptide contains a cleavage site recognized by a peptidase in the central nervous system; and (b) directions for use of the conjugate in the treatment of the central nervous system disease or disorder.

In another aspect, the present invention provides a kit for the treatment of a central nervous system disease or disorder, the kit comprising:

(a) a container holding a conjugate having the formula:

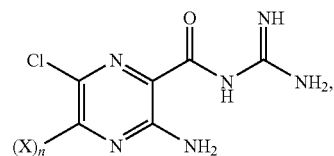

wherein X is a peptide comprising n independently selected amino acids, n is an integer greater than 1, and the peptide contains a cleavage site recognized by a peptidase in the central nervous system; and (b) directions for use of the conjugate in the treatment of the central nervous system disease or disorder.

In yet another aspect, the present invention provides a kit for the treatment of a central nervous system disease or disorder, the kit comprising:

(a) a container holding a conjugate having the formula:

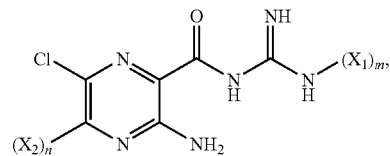

wherein $X_1$ and $X_2$ are peptides comprising m and n independently selected amino acids, respectively; and m and n are independently selected integers greater than 1, and at least one of the peptides contains a cleavage site recognized by a peptidase in the central nervous system; and (b) directions for use of the conjugate in the treatment of the central nervous system disease or disorder.

In still yet another aspect, the present invention provides a kit for the treatment of a central nervous system disease or disorder, the kit comprising:

(a) a container holding a conjugate having the formula:

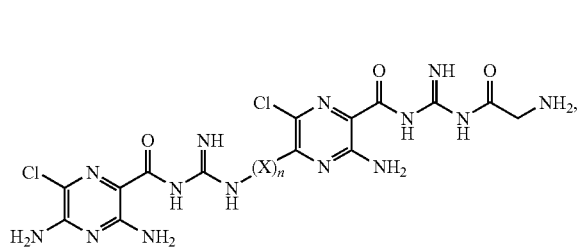

wherein X is a peptide comprising n independently selected amino acids, n is an integer greater than 1, and the peptide contains a cleavage site recognized by a peptidase in the central nervous system; and (b) directions for use of the conjugate in the treatment of the central nervous system disease or disorder.

Any of the above-described kits for the treatment of a central nervous system disease or disorder can further comprise a second container holding a co-administered peptidase inhibitor that does not cross the blood brain barrier (BBB) and directions for use of the conjugate and the co-administered peptidase inhibitor. Without being bound to any particular theory, co-administration of the peptidase inhibitor prevents the activation and/or degradation of the inactive amiloride conjugate prodrug prior to its crossing the BBB.

In a further aspect, the present invention provides a kit for the prevention or reduction of ischemia-reperfusion injury, the kit comprising:

(a) a container holding a conjugate having the formula:

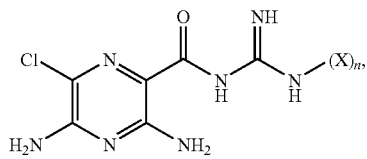

wherein X is a peptide comprising n independently selected amino acids, n is an integer greater than 1, and the peptide contains a cleavage site recognized by a peptidase in the ischemic tissue; and (b) directions for use of the conjugate in the prevention or reduction of the ischemia-reperfusion injury.

In another aspect, the present invention provides a kit for the prevention or reduction of ischemia-reperfusion injury, the kit comprising:

(a) a container holding a conjugate having the formula:

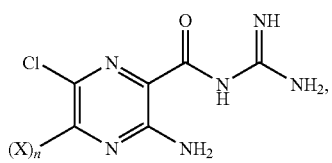

wherein X is a peptide comprising n independently selected amino acids, n is an integer greater than 1, and the peptide contains a cleavage site recognized by a peptidase in the ischemic tissue; and (b) directions for use of the conjugate in the prevention or reduction of the ischemia-reperfusion injury.

In yet another aspect, the present invention provides a kit for the prevention or reduction of ischemia-reperfusion injury, the kit comprising:

(a) a container holding a conjugate having the formula:

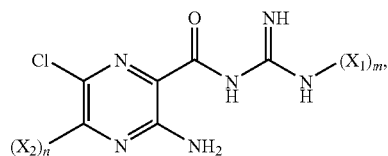

wherein $X_1$ and $X_2$ are peptides comprising m and n independently selected amino acids, respectively; and m and n are independently selected integers greater than 1, and at least one of the peptides contains a cleavage site recognized by a peptidase in the ischemic tissue; and (b) directions for use of the conjugate in the prevention or reduction of the ischemia-reperfusion injury.

In still yet another aspect, the present invention provides a kit for the prevention or reduction of ischemia-reperfusion injury, the kit comprising:

(a) a container holding a conjugate having the formula:

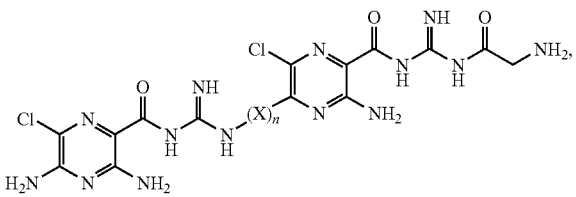

wherein X is a peptide comprising n independently selected amino acids, n is an integer greater than 1, and the peptide contains a cleavage site recognized by a peptidase in the ischemic tissue; and (b) directions for use of the conjugate in the prevention or reduction of the ischemia-reperfusion injury.

Any of the above-described kits for the prevention or reduction of ischemia-reperfusion injury can further comprise a second container holding a co-administered peptidase inhibitor and directions for use of the conjugate and the co-administered peptidase inhibitor. Without being bound to any particular theory, the peptidase inhibitor inhibits the activation and/or degradation of the inactive amiloride conjugate prodrug prior to the onset of ischemia.

IV. Compositions: Amiloride Amino Acid and Peptide Conjugates

The present invention provides novel amino acid and peptide conjugates of amiloride that are effective NHE1 and/or NCX inhibitors and display cytotoxic and/or anitproliferative effects on tumor cells such as glioma cells. Table 1 presents selected inhibitors of NHE1 and NCX as described in the literature and the novel amiloride conjugates of the present invention.

TABLE 1

NHE1 and NCX inhibitors from the literature and novel amiloride conjugates.

| | Structure | Rel. Activity | Glioma Effect |
|---|---|---|---|
| Literature | | | |
| Amiloride | (pyrazine structure with Cl, $R^1R^2N$, $NH_2$, and acylguanidine $NHR^3$) | NHE > NCX | $\geq$500 µM cytotoxic <50 µM antiproliferative |
| 2,4-Dichloro-benzamil | (amiloride analog with 2,4-dichlorobenzyl on guanidine) | NCX > NHE | 15 µM cytotoxic |
| SEA0400 | (EtO-phenyl-O-phenyl-O-CH$_2$-difluorophenyl with NH$_2$) | NCX only, no NHE activity ($Ca^{2+}$ influx mode > $Ca^{2+}$ efflux mode) | unknown |
| KB-R4793 | ($O_2N$-benzyl-O-phenyl-ethyl-S-C(NH)NH$_2$) | NCX > NHE (blocks $Ca^{2+}$ influx) | not cytotoxic not antiproliferative |
| Present Work | | | |
| C2am-Gly | (amiloride with Gly-NH$_2$ on guanidine) | NCX > NHE | $\leq$10 µM cytotoxic |
| C5am-Gly | (amiloride with HO$_2$C-CH$_2$-NH at 5-position) | NHE >> NCX | $\leq$100 µM antiproliferative |
| C2,5am-(Gly)$_2$ | (amiloride with Gly on guanidine and HO$_2$C-CH$_2$-NH at 5-position) | NCX ~ NHE | |

TABLE 1-continued

NHE1 and NCX inhibitors from the literature and novel amiloride conjugates.

|  | Rel. Activity | Glioma Effect |
|---|---|---|

C2–C5 Dimer

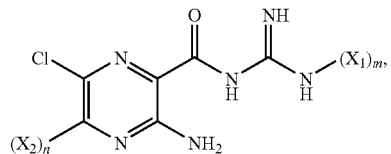

(X)$_n$ = peptide spacer
NCX > NHE prior to cleavage
NCX ~ NHE after cleavage

In addition to the C2am-Gly conjugate shown in Table 1, C2am-X conjugates, wherein X is an amino acid or a peptide, are within the scope of the present invention. As such, the present invention provides a C2am conjugate comprising the following structure:

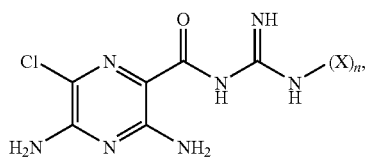

wherein X is n independently selected amino acids and n is an integer greater than or equal to 1. The amino acid or peptide is conjugated to the C(2) position of amiloride via an amide bond. When n is greater than 1, X is a peptide comprising a combination of independently selected amino acids or a polymer of one amino acid as described above. Preferably, the peptide is selectively cleaved by a peptidase, such as a brain-specific or tumor-specific peptidase, or an enzyme activated during tissue injury. In one embodiment, the peptide is a poly-glycine peptide. In a preferred embodiment, the amino acid or peptide is connected to the C(2) position of amiloride via a linker.

Likewise, in addition to the C5am-Gly conjugate shown in Table 1, C5am-X conjugates, wherein X is an amino acid or a peptide, are within the scope of the present invention. As such, the present invention provides a C5am conjugate comprising the following structure:

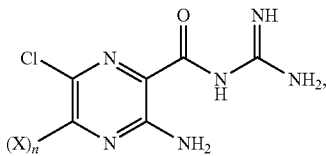

wherein X is n independently selected amino acids and n is an integer greater than or equal to 1. The amino acid or peptide is conjugated to the C(5) position of amiloride via an amine bond. When n is greater than 1, X is a peptide comprising a combination of independently selected amino acids or a polymer of one amino acid as described above. Preferably, the peptide is selectively cleaved by a peptidase, such as a brain-specific or tumor-specific peptidase, or an enzyme activated during tissue injury. In one embodiment, the peptide is a poly-glycine peptide. In a preferred embodiment, the amino acid or peptide is connected to the C(5) position of amiloride via a linker.

Further, in addition to the C2,5am-(Gly)$_2$ conjugate shown in Table 1, C2,5am-X$_1$-X$_2$ conjugates, wherein X$_1$ and X$_2$ independently comprise at least one amino acid, are within the scope of the present invention. As such, the present invention provides a C2,5am conjugate comprising the following structure:

wherein X$_1$ and X$_2$ are m and n independently selected amino acids, respectively, and m and n are independently selected integers greater than or equal to 1. The X$_1$ amino acid or peptide is conjugated to the C(2) position of amiloride via an amide bond and the X$_2$ amino acid or peptide is conjugated to the C(5) position of amiloride via an amine bond. When m and n are both greater than 1, X$_1$ and X$_2$ are either identical or different peptides comprising a combination of independently selected amino acids or a polymer of one amino acid as described above. Preferably, the peptide is selectively cleaved by a peptidase, such as a brain-specific or tumor-specific peptidase, or an enzyme activated during tissue injury. In one embodiment, the peptide is a poly-glycine peptide. In a preferred embodiment, the amino acid or peptide is connected to the C(2) and/or C(5) position of amiloride via a linker.

In another embodiment, both X$_1$ and X$_2$ are glycine residues and m and n are both 1 (i.e., C2,5am-(Gly)$_2$). C2,5am-(Gly)$_2$ is suitable for use as a pseudopeptide residue that is likely non-hydrolyzable by peptidases and which can be internally incorporated into peptides known to cross the blood brain barrier. For example, the following analogs of [Leu]$^5$-enkephalin amide can be generated that incorporate C2,5am-(Gly)$_2$ into the peptide sequence: (1) Tyr-Gly-am-Gly-Phe-Leu-NH$_2$ (see, FIG. 11); (2) Tyr-Gly-Gly-am-Gly-Gly-Phe-Leu-NH$_2$ (SEQ ID NO:8); and (3) Tyr-D-Ala-Gly-am-Gly-Phe-D-Leu-NH$_2$, wherein Gly-am-Gly is a C2,5am-(Gly)$_2$ conjugate. Such peptides can be tested with purified enkephalinase and fresh brain homogenates to analyze peptide fragmentation by LC-MS.

In a further embodiment, $X_1$ and $X_2$ are peptides wherein the amino-terminus of $X_1$ is coupled to the carboxyl-terminus of $X_2$ by a peptide bond to form a cyclized C2,5am-peptide conjugate. Preferably, the cyclized C2,5am-peptide conjugate comprises from 9 to 14 amino acids (i.e., the sum of m and n is between 9 and 14). The cyclized peptide would be biologically inactive and hydrophobic. However, endopeptidase cleavage of the $X_1$-$X_2$ peptide linker would generate a linear, functional, hydrophilic molecule.

In addition to the C2am-Gly-Peptide-C5am-Gly ("$C_2$-$C_5$ dimer") shown in Table 1, C2am-Amino Acid-C5am and C2am-Peptide-C5am dimers are within the scope of the present invention. As such, the present invention provides a C2,5am dimer conjugate comprising the following structure:

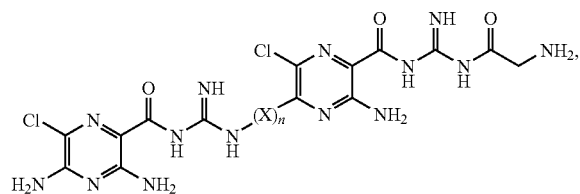

wherein X is n independently selected amino acids and n is an integer ranging from 1 to 50. When n is between 2 to 50, X is a peptide comprising a combination of independently selected amino acids or a polymer of one amino acid as described above. Preferably, n is between 4 and 12. Preferably, the peptide is selectively cleaved by a peptidase, such as a brain-specific or tumor-specific peptidase, or an enzyme activated during tissue injury. In one embodiment, the peptide is a poly-glycine peptide. In a preferred embodiment, the amino acid or peptide is connected to the C(2) position of one amiloride via one linker and to the C(S) position of another amiloride via another linker. C2,2am and C5,5am amino acid and peptide dimer conjugates are also within the scope of the present invention.

The C5am and C2am amino acid and peptide conjugates of the present invention are unique and have the following chemical properties that make them particularly useful therapeutic agents for the treatment of cancer (e.g., glioma, breast cancer), treatment of central nervous system disorders (e.g., traumatic brain injury, seizure), prevention or reduction of ischemia-reperfusion injury, etc.:

a. The C2am and C5am amino acid conjugates are more polar than other amiloride derivatives. Their hydrophilicity has facilitated aqueous solubilization and restricts their activity to ionic exchangers on the cell surface, thereby reducing general toxicity.

b. The C5am-Gly conjugate inhibits NHE1 at greater than 4 times the potency of amiloride in glioma cells, and the inhibition is rapidly reversed when the conjugate is removed from the bath (Palandoken et al., supra). The C2am-Gly conjugate kills glioma cells at greater than 50 times the potency of amiloride.

c. The C2am and C5am amino acid conjugates are efficiently coupled to peptides that can be designed to contain cleavage sites recognized by brain-, tumor-, or ischemic tissue-specific peptidases. Cleavage of the peptide conjugates produces proteolytic products that can be considerably more polar than the parent conjugate. For example, combinatorial peptide chemistry can generate a large number of derivatives that can be screened to optimize glioma cytotoxicity and selectivity.

d. The C2,5am-(Gly)$_2$ conjugate (i.e., 2,5-bis-glycine amiloride) is a "pseudo-peptide" residue that can be introduced within peptides. This pseudo-peptide residue can be resistant to peptidases and can be introduced into peptides that are transported across the blood brain barrier (BBB).

e. The C2,5am-(Gly)$_2$-peptide conjugate (i.e., Peptide 1-Gly-am-Gly-Peptide 2) can be made more hydrophobic by protecting any free carboxylic acid groups, e.g., with a protecting group. Enzymatic cleavage of Peptide 1 and/or Peptide 2 liberates the more hydrophilic, bifunctional molecule Gly-am-Gly, capable of modulating the inhibition of both NHE1 and NCX.

f. The $C_2$-$C_5$ dimeric amiloride conjugates can be coupled to each other through a peptide linkage that generates a hydrophobic, di-amide molecule. Blocking C-terminal carboxylates by amidation or methylation has been shown to facilitate access across the BBB. For example, the more hydrophilic C2am-Gly and C5am-Gly can be released following cleavage of the internal peptide linkage from a hydrophobic $C_2$-$C_5$ dimeric amiloride glycine conjugate by brain-, tumor-, or ischemic tissue-specific peptidases.

In view of the above and the Examples below, the present invention provides methods for administering hydrophobic peptide-drug conjugates that can then be converted in vivo to hydrophilic agents upon the action of a peptidase. These methods permit efficient accessibility and penetration of the conjugates into a tissue (e.g., ischemic tissue) or other site of action (e.g., across the blood brain barrier) and utilize peptidases present in the tissue or site of action to selectively cleave the conjugate and liberate a hydrophilic agent that acts at the level of the cell surface, thereby reducing general toxicity. Suitable drugs for use in the peptide-drug conjugates include, without limitation, anti-cancer agents, anti-inflammatory agents, anti-viral agents, antifungal agents, and antibacterial agents, wherein the peptide conjugated to the drug is selectively cleaved by a peptidase expressed at the intended site of drug action, e.g., a tumor, an injured tissue, an organ, etc., to generate the hydrophilic agent.

The amiloride conjugates of the present invention can be provided in pharmaceutical compositions for administration to a subject in need thereof. Such compositions will contain, in addition to at least one amiloride conjugate as the active agent(s), one or more pharmaceutically acceptable excipients, carriers, diluents, tissue permeation enhancers, solubilizers, and adjuvants. Other therapeutic agents may be included, e.g., anticancer agents, vasoconstrictors, anti-inflammatory agents, antibiotics, and counter-irritants. Suitable anticancer agents include, but are not limited to, cytotoxins and agents such as antimetabolites, alkylating agents, anthracyclines, antibiotics, antimitotic agents, procarbazine, hydroxyurea, asparaginase, corticosteroids, interferons, radiopharmaceuticals, and conjugates of peptides with anti-tumor activity, e.g., TNF-α. The compositions may be formulated using conventional techniques such as those described in Remington's Pharmaceutical Sciences, Mace Publishing Co., Philadelphia, Pa. 17$^{th}$ Ed. (1985) and "Modern Pharmaceutics," Marcel Dekker, Inc. 3$^{rd}$ Ed. (G. S. Banker & C. T. Rhodes, Eds.). Pharmaceutically acceptable salts of the amiloride conjugates (e.g., acid addition salts) may be prepared using standard procedures known to those skilled in the art of synthetic organic chemistry and described, e.g., by J.

March, *Advanced Organic Chemistry: Reactions, Mechanisms and Structure*, 4th Ed. (New York: Wiley-Interscience, 1992).

For topical administration, the compositions of the present invention comprising amiloride conjugates can be in the form of emulsions, creams, jelly, solutions, and ointments. For parenteral administration, the compositions can be in the form of sterile injectable solutions and sterile packaged powders. Preferably, injectable solutions are formulated at a pH of about 4.5 to about 7.5. For oral administration, the compositions can be in the form of tablets, capsules, emulsions, suspensions, solutions, syrups, sprays, and lozenges. Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, and methylcellulose. The compositions can additionally include lubricating agents such as talc, magnesium stearate, and mineral oil; wetting agents, emulsifying and suspending agents; preserving agents such as methyl- and propylhydroxy-benzoates, sweetening agents, and flavoring agents. The compositions may also comprise biodegradable polymer beads and dextran and cyclodextrin inclusion complexes.

Design, Synthesis, and In Vitro Evaluation of Novel Amiloride Compounds

In a preferred embodiment, the C5am and C2am peptide conjugates of the present invention are selectively cleaved within the brain by an opioid neuropeptide peptidase (e.g., enkephalinase), a metalloproteinase (e.g., matrix metalloproteinase, disintegrin-metalloproteinase (ADAM)), a plasminogen activator, a cathepsin, a calpain, a caspase, or combinations thereof. Typically, peptides are designed to identify the minimum number of amino acid residues that optimally (1) discriminate between glioma cells and astrocytes; and (2) inhibit NCX and/or NHE1. In addition, enzymatic recognition sequences are designed within the peptides to permit selective cleavage by enzymes (e.g., brain and/or tumor peptidases). For example, C5am-Gly or C2am-Gly conjugates containing peptides that mimic opioid peptides or MMP-2 substrates attached to the glycine are within the scope of the present invention. Such conjugates can be evaluated for any of various structure-activity relationships (SAR) such as enzymatic specificity and biological activity in glioma cells. In a particularly preferred embodiment, the C5am-Gly or C2am-Gly conjugates are coupled to [Leu]$^5$-enkephalin analogs (e.g., Gly-Gly-Gly-Gly-Phe-Leu (SEQ ID NO:1)) that closely resemble members of the opioid peptide family that effectively enter the brain following intravenous injection (Cornford et al., *Lancet Neurol.*, 1:306-315 (2002)). Any of the peptide conjugates of the present invention are useful for enhancing the efficacy and selectivity (i.e., specificity) of the antiproliferative and cytotoxic effects of amiloride conjugates in killing and/or inhibiting the proliferation of tumor cells such as glioma cells. Recognition sequences within the conjugates are designed to be cleaved by brain or tumor peptidases to increase the hydrophilicities of the active compounds to impede their intracellular permeation, thereby reducing toxicity.

The C2am-Gly, C5am-Gly, and peptide conjugates thereof are synthesized with high overall yields. Preferably, the conjugates demonstrate cytotoxic and/or antiproliferative effects on U87 glioma cells that correspond with their predicted inhibition of NCX and NHE1. Although solubilization is a common problem with peptides, the peptide conjugates of the present invention are soluble in mixtures of aqueous buffers containing approximately <20% of DMSO. As peptide derivatives frequently need modified amino acid residues in order to be clinically effective and/or to prevent unwanted cleavage by endogenous peptidases, D-amino acids, N-methyl amino acids, N-substituted glycines, cyclic amino acid derivatives, and combinations thereof may be introduced into the peptide conjugates of the present invention. For example, "peptidomimetism" introduces hydrocarbon bonds that retain the confomeric structure of the peptide backbones, while retaining critical amino acid sidechains to overcome problems of peptide instability, poor absorption, and rapid metabolism (Marshall, *Biopolymers*, 60:246-277 (2001)). Further, combinatorial peptide syntheses can rapidly generate novel sets of amiloride derivative compounds that can be examined to optimize efficacies using high throughput, tetrazolium-based screening assays of viable cell numbers of glioma cells and primary astrocytes.

A particularly appealing feature of the synthesis strategies of the present invention is the flexibility with which the peptide side chains can be incorporated onto the amiloride core. For example, partial or complete peptide sequences may be assembled prior to the reaction with resin-bound amiloride, as opposed to a step-wise amino acid sequence construction. This option provides the opportunity to incorporate radiolabels into the synthetic scheme by using radiolabeled peptide sequences. The incorporation of radiolabels could be particularly useful following preliminary LC-MS analyses to further assess the partitioning of compounds from the vascular compartment into brain tissue, their intracerebral efflux, and stability.

Peptidases, Peptide Substrates, and Amiloride-Peptide Conjugates

The endopeptidase subclass of peptidases (EC3.4) is divided into sub-subclasses on the basis of catalytic mechanism, and their specificity is used to identify individual enzymes within the groups. These are the sub-subclasses of serine endopeptidases (EC 3.4.21), cysteine endopeptidases (EC 3.4.22), aspartic endopeptidases (EC 3.4.23), metalloendopeptidases (EC 3.4.24), and threonine endopeptidases (EC 3.4.25). Endopeptidases that cannot be assigned to any of the sub-subclasses listed above are provided in sub-subclass EC 3.4.99.

The endopeptidases shown in Table 2 are activated by tissue injury, hypoxia-ischemia, and/or in infiltrative cancers, including grade III and IV malignant gliomas. Any peptidase uniquely or selectively expressed by a tumor, tissue, or organ could provide a target for selective cleavage of an amiloride-peptide conjugate of the present invention. Table 2 shows various known peptide substrates for: (1) peptidases activated by tissue injury or hypoxia-ischemia (e.g., heart and brain), such as calpains and caspases; and (2) peptidases activated by tumors (e.g., brain tumors), such as matrix metalloproteinases and urokinase plasminogen activators. Further, Table 2 shows amiloride-peptide conjugates that can be selectively cleaved with the specific peptidase(s).

TABLE 2

Peptidases, Known Peptide Substrates, and Amiloride-Peptide Conjugates.

| Peptidase | Known Peptide Substrates | Amiloride-Peptide Conjugates* |
|---|---|---|
| Calpain I (EC 3.4.22.52) and Calpain II (EC 3.4.22.32) | N-Succinyl-Leu-Tyr-7-amido-4-Methylcoumarin | N-Succinyl-Leu-Tyr-$(X)_n$-C5am; $(X)_m$-Leu-Tyr-$(Y)_n$-C5am; C2am-$(X)_m$-Leu-Tyr-$(Y)_n$-amide; C2am-$(X)_m$-Leu-Tyr-$(Y)_n$-methyl ester; C2am-$(X)_m$-Leu-Tyr-$(Y)_n$-C5am dimer |
| Calpain II (EC 3.4.22.32) | N-Succinyl-Leu-Leu-Val-Tyr-7-Amido-4-Methylcoumarin | N-Succinyl-Leu-Leu-Val-Tyr-$(X)_n$-C5am; $(X)_m$-Leu-Leu-Val-Tyr-$(Y)_n$-C5am; C2am-$(X)_m$-Leu-Leu-Val-Tyr-$(Y)_n$-amide; C2am-$(X)_m$-Leu-Leu-Val-Tyr-$(Y)_n$-methyl ester; C2am-$(X)_m$-Leu-Leu-Val-Tyr-$(Y)_n$-C5am dimer |
| Caspase 3 | N-Acetyl-Asp-Glu-Val-Asp-p-nitroanilide | N-Acetyl-Asp-Glu-Val-Asp-$(X)_n$-C5am; $(X)_m$-Asp-Glu-Val-Asp-$(Y)_n$-C5am; C2am-$(X)_m$-Asp-Glu-Val-Asp-$(Y)_n$-amide; C2am-$(X)_m$-Asp-Glu-Val-Asp-$(Y)_n$-methyl ester; C2am-$(X)_m$-Asp-Glu-Val-Asp-$(Y)_n$-C5am dimer |
| Caspase 9 | N-Acetyl-Leu-Glu-His-Asp-p-nitroaniline | N-Acetyl-Leu-Glu-His-Asp-$(X)_n$-C5am; $(X)_m$-Leu-Glu-His-Asp-$(Y)_n$-C5am; C2am-$(X)_m$-Leu-Glu-His-Asp-$(Y)_n$-amide; C2am-$(X)_m$-Leu-Glu-His-Asp-$(Y)_n$-methyl ester; C2am-$(X)_m$-Leu-Glu-His-Asp-$(Y)_n$-C5am dimer |
| MMP-2 (EC 3.4.24.24) | See, Chen et al., J. Biol. Chem., 277:4485–4491 (2002) | $(X)_m$-Glu-Ser-Leu-Ala-Tyr-Tyr-Thr-Ala-$(Y)_n$-C5am; C2am-$(X)_m$-Glu-Ser-Leu-Ala-Tyr-Tyr-Thr-Ala-$(Y)_n$-amide; C2am-$(X)_m$-Glu-Ser-Leu-Ala-Tyr-Tyr-Thr-Ala-$(Y)_n$-methyl ester; C2am-$(X)_m$-Glu-Ser-Leu-Ala-Tyr-Tyr-Thr-Ala-$(Y)_n$-C5am dimer $(X)_m$-Arg-Ser-Leu-Ser-Arg-Leu-Thr-Ala-$(Y)_n$-C5am; C2am-$(X)_m$-Arg-Ser-Leu-Ser-Arg-Leu-Thr-Ala-$(Y)_n$-amide; C2am-$(X)_m$-Arg-Ser-Leu-Ser-Arg-Leu-Thr-Ala-$(Y)_n$-methyl ester; C2am-$(X)_m$-Arg-Ser-Leu-Ser-Arg-Leu-Thr-Ala-$(Y)_n$-C5am dimer $(X)_m$-Arg-Ser-Leu-Ser-Arg-Leu-Thr-Ala-Gly-$(Y)_n$-C5am; C2am-$(X)_m$-Arg-Ser-Leu-Ser-Arg-Leu-Thr-Ala-Gly-$(Y)_n$-amide; C2am-$(X)_m$-Arg-Ser-Leu-Ser-Arg-Leu-Thr-Ala-Gly-$(Y)_n$-methyl ester; C2am-$(X)_m$-Arg-Ser-Leu-Ser-Arg-Leu-Thr-Ala-Gly-$(Y)_n$-C5am dimer |
| Urokinase Plasminogen Activator | p-Tosyl-Arg-methyl ester | |

*X and Y are amino acids and m and n are each independently 0–6 amino acid residues.

When the compositions of the present invention are administered orally, the peptide sequences in the amiloride-peptide conjugate are preferably designed to be resistant to digestive enzymes such as trypsin, chymotrypsin, elastase, and carboxypeptidases. When the compositions are administered intravenously, the conjugates are preferably resistant to plasma proteases such as those of the thrombolytic pathway (e.g., thrombin).

As discussed above, peptide derivatives frequently need modified amino acid residues in order to be clinically effective and/or to prevent unwanted cleavage by endogenous peptidases. Therefore, D-amino acids, N-methyl amino acids, N-substituted glycines, cyclic amino acid derivatives, and combinations thereof may be introduced into the amiloride-peptide conjugates of the present invention, and peptidomimetism can be used to overcome problems of peptide instability, poor absorption, and rapid metabolism (Marshall, supra). For example, an MMP-2-cleavable peptide linker can contain modified amino acid residues flanking the MMP-2 cleavage sequence in order to confer resistance to endogenous peptidases other than MMP-2.

Utility of Novel Amiloride Compounds

The C5am-amino acid and peptide conjugates are particularly useful as highly selective and potent inhibitors of sodium-proton exchange (i.e., NHE1) whereas C2am-amino acid and peptide conjugates are particularly useful as selective and potent inhibitors of sodium-calcium exchange (i.e., NCX). Thus, C5am conjugates are particularly useful for reducing tissue swelling (e.g., acute brain swelling from stroke or head trauma) and C2am conjugates in conjuction with C5am conjugates are particularly useful for killing cancer cells that reside in hypoxic-ischemic environments and/or for serving as a neuroprotectant during stroke or cardiac ischemia by preventing sodium and calcium entry into cells via NHE1 and NCX, respectively. Further, conjugates produced by peptide additions to both the C2 and C5 positions of amiloride are particularly useful because they would likely change the ratio of NCX/NHE1 inhibition and affect the selectivity for inhibiting the different transporter subtypes present in different tissues. This could be assessed using high throughput screens for each transporter.

Mechanisms of Action of Novel Amiloride Compounds

Without being bound to any particular theory, it is thought that the amiloride conjugates of the present invention provide cytotoxic and/or antiproliferative effects by at least one of the following mechanisms: (1) reduction in intracellular pH ($pH_i$); (2) impairment of glycolysis; and (3) increase in intracellular calcium levels ($[Ca^{2+}]_i$). Such effects are mediated by inhibition of NHE1, NCX, a combination of NHE1 and NCX, or through inhibition of other ionic transporters (e.g., other cell-surface $Na^+$ exchangers).

FIG. 1 illustrates a model for amiloride conjugate-induced tumor cell death. In FIG. 1A, increased activation of NHE1 (1) in tumor cells (e.g., glioma cells) causes intracellular alkalosis with an accumulation of $[Na^+]_i$ and $[Ca^{2+}]_i$. However, either the addition of (1) an amiloride conjugate that inhibits both NHE1 and NCX or (2) a combination of NHE1- and NCX-specific amiloride conjugates, causes a dramatic increase in intracellular calcium levels, ultimately leading to tumor cell death. In particular, FIG. 1B shows that the cell death is achieved by the inhibition of NCX (2), which results in $[Ca^{2+}]_i$ accumulation, and the inhibition of NHE1, which results in a reduction in $pH_i$, impairing glycolysis and leading to the release of additional calcium from energetically sensitive intracellular stores such as the mitochondria (mito, 4) and the endoplasmic reticulum (ER, 5).

V. Methods of Administration

The compositions of the present invention comprising an amiloride conjugate may be administered by any of the accepted modes of administration of agents having similar utilities, for example, by oral administration, administration as a suppository, topical contact, intravenous, intraperitoneal, intramuscular, intralesional, intraarterial, intrathecal, intranasal or subcutaneous administration, or the implantation of a slow-release device, e.g., a mini-osmotic pump, to a subject. Administration is by any route, including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The compositions may be administered as a single injection or continuously through an indwelling catheter, or administered topically to the skin, mucus membranes, etc. The composition containing the amiloride conjugate may be administered repeatedly, e.g., at least 2, 3, 4, 5, 6, 7, 8, or more times, or the composition may be administered by continuous infusion.

The compositions can be formulated in a unit dosage form. The term "unit dosage form" refers to physically discrete units suitable as unitary dosages for human subjects and other mammals, each unit containing a predetermined quantity of active material calculated to produce the desired onset, tolerability, and therapeutic effects, in association with a suitable pharmaceutical excipient (e.g., an ampule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of the amiloride conjugate.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. In one embodiment of the present invention, the lyophilized composition is provided in a syringe, optionally packaged in combination with the buffer for reconstitution, such that the reconstituted anesthetic composition can be immediately administered to a patient.

The dose administered will vary depending on a number of factors, including, but not limited to, the type of cancer or ischemic tissue, the location of the tumor or ischemic tissue, and/or the physical condition of the patient. Preferably, the smallest dose and concentration required to produce the desired result should be used. Dosage should be appropriately adjusted for children, the elderly, debilitated patients, and patients with cardiac and/or liver disease. However, the reduced toxicity associated with the amiloride conjugates of the present invention permits a wider margin of safety for dosage concentrations and for repeated dosing.

In certain instances, the methods of the present invention further comprise co-administering to the subject an agent (e.g., small organic molecule, peptide, protein, polypeptide, peptidase, oligosaccharide, etc.) that activates an endogenous peptidase (e.g., a tumor-specific peptidase) which in turn selectively cleaves a peptide on the amiloride conjugate. In certain other instances, the methods of the present invention further comprise co-administering to the subject a peptidase that selectively cleaves a peptide on the amiloride conjugate. Administration of the agent or peptidase may occur either at the same time as the administration of the amiloride conjugate, or may be administered sequentially in a predetermined order. In a preferred embodiment, the agent or peptidase is administered to a subject after the amiloride conjugate is administered. The time of agent or peptidase administration following amiloride conjugate administration, or "intervention time," is influenced by a number of factors, such as blood clearance rates and tumor uptake and clearance rates. Preferably, the intervention time is between 1 and 24 hours. More preferably, the intervention time is at about 6 hours. The intervention time should be such that the agent or peptidase increases the release of an active (i.e., bioactive) proteolytic product from the conjugate relative to its release in the absence of the agent or peptidase. In a preferred embodiment, the proteolytic product is amiloride ("am"), C2am-Gly, C5am-Gly, C2,5am-(Gly)$_2$, or combinations thereof.

VI. Examples

The following examples are offered to illustrate, but not to limit, the claimed invention.

Example 1

Figure 2:
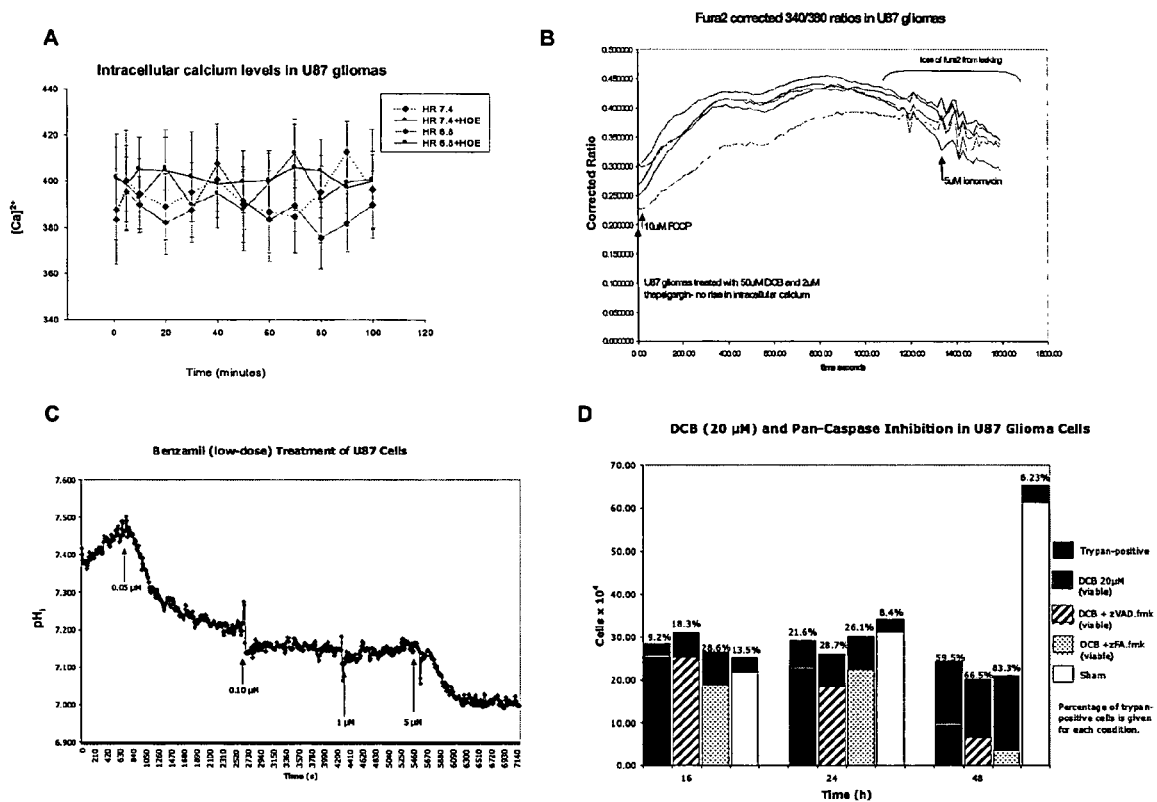
FIG. 2A shows the elevated levels of $[Ca^{2+}]_i$ in U87 gliomas at $pH_O$ 7.4 and 6.8. NHE1 inhibition with HOE694 did not alter $[Ca^{2+}]_i$.
FIG. 2B shows that pretreatment with DCB caused FCCP-induced $[Ca^{2+}]_i$ to increase to cytotoxic levels that preceded the leakage of fura-2 from dying cells.
FIG. 2C shows that DCB is an NCX inhibitor that at concentrations between 50-100 nM also inhibits NHE1 and acidifies U87 glioma cells loaded with BCECF.
FIG. 2D shows that DCB at $\geq$20 μM killed glioma cells. Cell death was minimally affected by caspase inhibitors.

Calcium-Dependent Cytotoxic Effects of High Concentrations of Amiloride on Human Malignant Gliomas This example shows that high concentrations of amiloride (e.g., $\geq$500 µM) selectively killed glioma cells, but not astrocytes, within 48-72 hours. Glioma cell death was morphologically necrotic with swollen cytoplasm and pycknotic nuclei, and cells were killed by a predominantly caspase-independent mechanism, except at later stages of cell death. Amiloride inhibits NCX with an IC$_{50}$ of 500 µM (Frelin et al., *Biochimie*, 70:1285-1290 (1988)). Manual cell counts with the trypan blue cell exclusion assay demonstrated that cariporide, a selective NHE1 inhibitor, and direct acidification (pH$_o$ 6.6, pH$_i$ 6.9) were also cytotoxic to glioma cells. Further, the NCX inhibitor, 2,4-dichlorobenzamil (DCB), killed glioma cells at concentrations of $\geq$20 µM (FIG. 2D). However, KB-R7943, which blocks the reverse mode of NCX, was non-toxic to glioma cells. These pharmacological data indicate that inhibition of sodium-dependent calcium efflux best explains the cytotoxicity of DCB and high doses of amiloride (Hedge et al., supra).

NHE1 inhibition reduced pH$_i$ in U87 glioma cells from 7.38 to 6.90. Previous studies have demonstrated in C6 glioma cells that a modest pH$_i$ reduction impairs glycolysis and reduces intracellular levels of ATP (Erecinska et al., id; Silver et al., *Glia*, 21:35-45 (1997)). ATP- and NADH-depletion has been shown to release calcium from intracellular stores in metabolically compromised astrocytes (Chini et al., *Biochem. J*, 335:499-504 (1998); Wu et al., *Glia*, 21:315-326. (1997)), but their effects on glioma cells with elevated basal levels of [Ca$^{2+}$]$_i$ are unknown. Therefore, the levels of [Ca$^{2+}$]$_i$ in U87 glioma cells loaded with fura-2AM were measured using quantitative fluorescent microscopy. U87 glioma cells were found to have [Ca$^{2+}$]$_i$ levels of 400 nM that were 5-fold higher than that of primary astrocytes (FIG. 2A). The ATP-dependent calcium regulatory mechanisms within U87 glioma cells containing fura-2 were then examined. Inhibition of Na$^+$-K$^+$ ATPase by oubain did not demonstrably alter [Ca$^{2+}$]$_i$ levels. Inhibition of ER-associated Ca$^{2+}$ ATPase (SERCA) by thapsigargin produced a modest and transient increase in [Ca$^{2+}$]$_i$. Inhibition of F$_0$F$_1$ATPase with oligomycin generated large [Ca$^{2+}$]$_i$ transients of >800 nM that were comparable to those produced by collapsing the transmitochondrial membrane potential ($\Psi$m) with FCCP. The large calcium release from mitochondrial stores with oligomycin is consistent with ATP synthase utilizing cytosolic ATP to maintain the $\Psi$m. ATP synthase operates in reverse when milimolar concentrations of calcium are stored by the mitochondrion (Nicholls, *Bioenergetics*, 3, Academic Press, London, 3$^{rd}$ edition (2002)).

The increased levels of [Ca$^{2+}$]$_i$ generated by oligomycin or FCCP persisted when external sodium was replaced with the impermeant analog, N-methylglucamine (NMDG). This demonstrated that a sodium-dependent calcium efflux pathway was being used by glioma cells to regulate calcium release from intracellular stores. DCB pretreatment followed by either oligomycin or FCCP also caused a persistent increase of [Ca$^{2+}$]$_i$ to >800 nM and was followed by fura-2 leaking from dying cells (FIG. 2B). By contrast, pretreatment with KB-R7943 did not cause a persistent increase in [Ca$^{2+}$]$_i$ following calcium release from mitochondrial stores. Similar to amiloride, DCB was observed to inhibit NHE1 and reduce the pH$_i$ of U87 glioma cells at low concentrations of 50-100 nM (FIG. 2C). Thus, inhibition of the sodium-dependent calcium efflux mode of NCX further increased the elevated basal levels of [Ca$^{2+}$]$_i$ in glioma cells. In addition, impaired glycolysis from NHE1 inhibition led to calcium release from intracellular stores that further contributed to calcium-mediated cytotoxicity.

Example 2

Effect of Amiloride on Glioma Cell Proliferation and Cell Death

This example shows that amiloride infusion slowed the rate of tumor doubling in intracerebral glioma xenografts and caused glioma cell death in poorly vascularized regions of the tumor. U87 glioma cells were stereotaxically implanted into the corpus striatum of brains of athymic (i.e., T-cell deficient) rats and characterized as an in vivo treatment model. Nissl-stained coronal sections were used to calculate tumor volumes from day 4 to day 28 post-implantation. T1-weighted NMR images were acquired from a separate set of animals to serially measure tumor volumes of intracerebral U87 glioma xenografts. There was close correspondence between tumor volumes determined independently by the two methodologies, and tumor growth rates closely approximated a Gompertzian kinetic model (Rygaard et al., *Breast Cancer Res. Treat.*, 46:303-312 (1997)). Therefore, U87 tumor growth was monitored serially by NMR as the animals were infused with amiloride for 5 days using Alzet pumps that were fitted with nonparamagnetic plastic hubs and cannulas.

Figure 3:
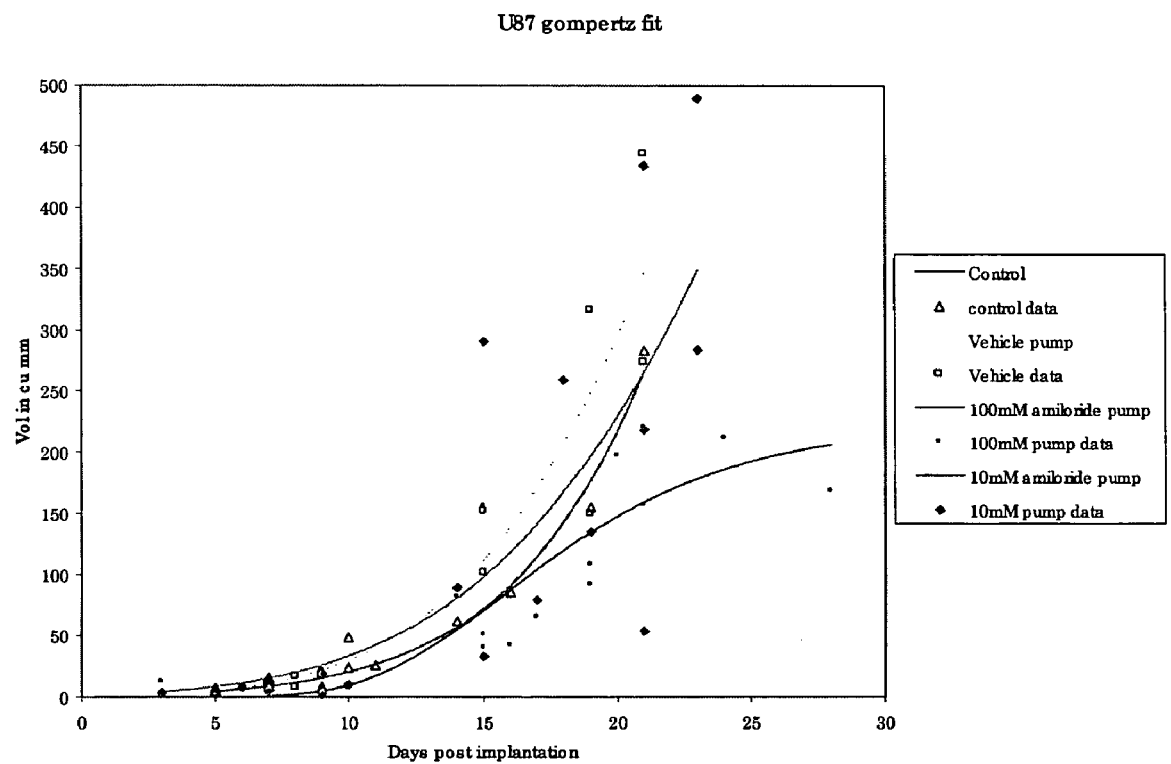
FIG. 3 shows the tumor growth kinetics of intracerebral U87 glioma xenografts with different intracerebral treatments.

As shown in FIG. 3 and Table 3, infusing 276 pmol per 24 h of amiloride for 5 days (100 mM reservoir, 276 pmol/24 h, 1.4 nmol total dose) increased the tumor doubling rate 3-fold compared to vehicle-treated animals. However, infusing less amiloride (10 mM reservoir, 28 pmol/24 h, 0.14 nmol) did not affect the tumor growth rate (Table 3). BrdU was injected intraperitoneally 3 h prior to perfusion fixation with paraformaldehyde in deeply anesthetized animals. Histological analyses demonstrated that normal brain cell types were unaffected by intracerebral amiloride infusion. Eosin staining identified necrotic glioma cell death that was confined to poorly vascularized tumor regions. Treated tumors, but not vehicle-treated controls, contained glioma cells with damaged double-stranded, nuclear DNA that were identified using an antibody against H2Ax, a histone protein that binds to damaged double-stranded, nuclear DNA that can be produced by radiotherapy (Rogakou et al., *J. Biol. Chem.*, 273: 5858-5868 (1998)).

TABLE 3

Altered tumor doubling times following 5 days of amiloride or vehicle infusion.

| day postimplant | Doubling time 10 | 12* | 15* | 17* | # of animals | # of measurements | R (gompertzian fit) |
|---|---|---|---|---|---|---|---|
| control | 2.65 | 2.81 | 3.10 | 3.25 | 9 | 15 | 0.98915219 |
| Vehicle pump | 2.46 | 2.80 | 3.40 | 3.81 | 3 | 10 | 0.92141969 |
| 10 mM amiloride reservoir | 3.07 | 3.40 | 3.99 | 4.44 | 3 | 18 | 0.84935900 |
| 100 mM amiloride reservoir | 1.23 | 1.98 | 4.58+ | 11.65++ | 8 | 32 | 0.90521755 |

*drug infusion day 12–17;
+statistically significant at P < 0.01;
++statistically significant at P < 0.001

These data indicate that the intracerebral infusion of amiloride at relatively high doses significantly slowed tumor growth rates and killed glioma in poorly vascularized tumor regions compared with vehicle-treated controls. Glioma cells in hypoxic-ischemic tumor environments lack extracellular $CO_2/HCO_3^-$ and rely entirely upon increased activity of NHE1 to maintain their intracellular pH (McLean et al., supra). Histochemical analysis of intracerebral C6 glioma xenografts containing large areas of necrosis which spontaneously occur within poorly vascularized tumor regions were also performed. Glioma cells bordering regions of spontaneous necrosis in intracerebral C6 xenografts were found to survive, undergo cell cycle arrest, and appear to rely predominantly upon non-oxidative glycolysis (Gorin et al., Acta Neuropathol. 107:235-244 (2004)). Such glioma cells were also found to be scattered throughout the poorly vascularized tumor regions and continued to incorporate BrdU. Amiloride infusion killed glioma cells in poorly vascularized, hypoxic tumor environments that can be resistant to conventional chemotherapies and radiation therapy and are therefore prone to recurrence. As such, the elevated level of $[Ca^{2+}]_i$ caused by increased NHE1 activity in these poorly vascularized glioma cells increases their susceptibility to pharmacological inhibitors of NCX and NHE1.

Figure 4:
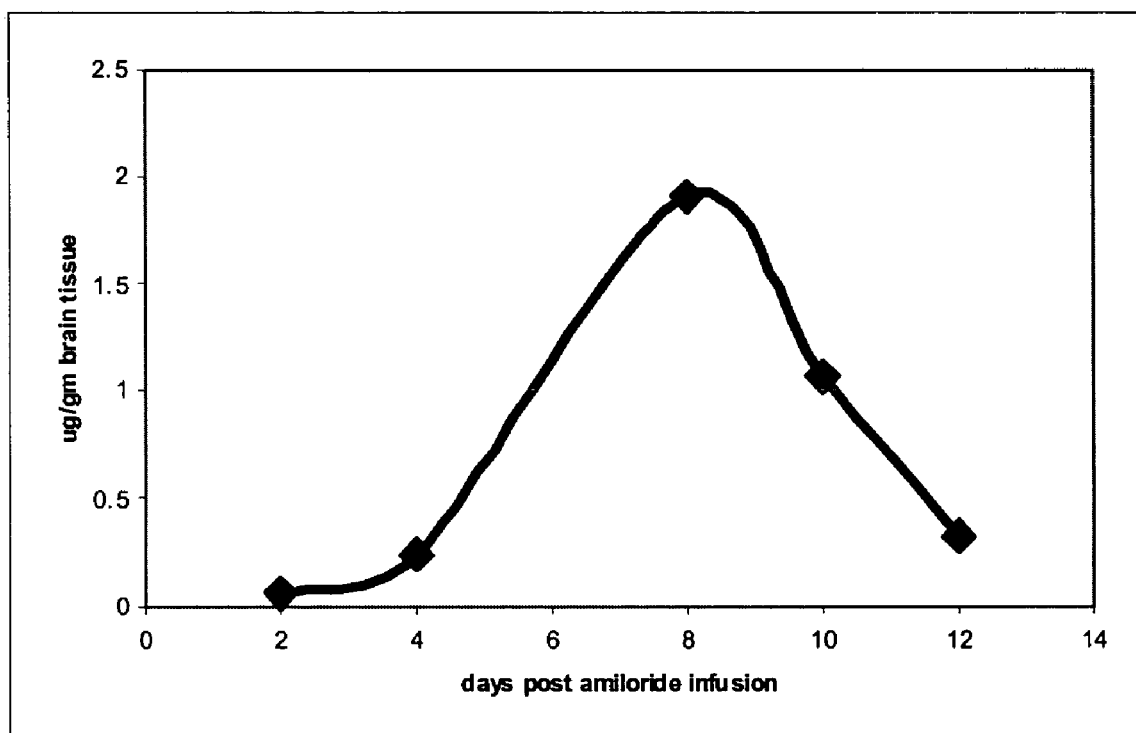
FIG. 4 shows that 100 mM amiloride in the reservoir of an Alzet pump optimally releases 276 pmol/24 h for 14 days. A total of 3.3 nmoles of amiloride were infused intracerebrally over 12 days with maximal accumulation occurring by 8 days.

The amiloride release profile from the reservoir in the Alzet pumps over 12 days was also determined and is shown in FIG. 4. Liquid chromatography coupled to electrospray mass spectroscopy (LCMS) was used to measure amiloride levels in the brain following 12 days of amiloride infusion (276 pmol/24 h). An extraction method of brain powder with dimethylacetamide (DMA) produced a 68% recovery of amiloride. LCMS (UCD Molecular Structure Facility) was capable of quantitatively detecting 10 pg (0.15 fmol) of amiloride.

Example 3

Neuropathological and Neurobehavioral Effects of Amiloride or DCB Intracerebral Administration Neuropathological changes were not observed in normal brain cell types of 250-280 gm Sprague-Dawley (S-D) control rats that received 12 days of intracerebral amiloride infusion (276 pmol/24 h). Parasaggital sections were stained with hematoxylin and eosin in addition to using specialized stains for neuronal damage (FluoroJade) and for myelinated fiber tracts (luxol fast blue). Intrathecal infusion of amiloride (276 pmol/24 h) in 250 gm S-D male rats did modestly affect spatial performance (see, FIG. 5B). Although Morris water maze (MWM) performance improved significantly (i.e., shorter swim time to find the platform) for both groups across training days indicating acquisition of the learning task, there was a persistent difference in performance between vehicle and amiloride groups. Intermittent seizures were also observed in 3 of 8 animals receiving amiloride infusion. There were no premature deaths.

Figure 5:
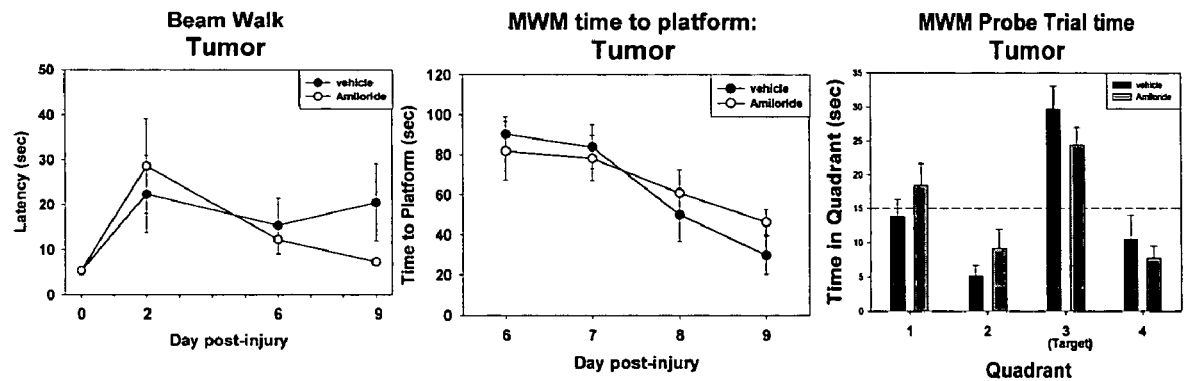
FIG. 5 shows the behavioral testing over 9 days of rats receiving intrathecal amiloride infusion.

FIG. 5A shows that intrathecal infusion of amiloride in rats did not affect balance and fine motor control. Both amiloride- and vehicle-treated groups displayed moderate deficits in fine motor coordination and balance ability indicated by increased latency to cross the beam compared to baseline (Day 0). No significant differences in performance were observed between amiloride and vehicle treated groups (n=6/group; means+/−SEM). FIG. 5C shows that intrathecal infusion of amiloride in rats did not affect memory in a spatial learning task. Rats were subjected to a "probe" trial following the last acquisition trial in MWM assessment following tumor and drug administration. The hidden platform was removed and the rat was allowed to swim for 60 seconds. The duration of time spent in the "target" quadrant (formerly containing the platform) was recorded. The dashed line indicates chance performance at 15 seconds. Both groups of rats demonstrated memory for the position of the hidden platform by increased time spent in the target quadrant. There was no significant difference in performance between amiloride and vehicle groups. Thus, amiloride infused at 276 pmol/24 h was associated with modest impairment of spatial learning and with occasional seizures, but no demonstrable neuropathology.

A single intracerebral infusion of DCB (10 pmol over 2 h) in 5 animals produced histological evidence of extensive glioma death within poorly vascularized tumor regions. Unfortunately, DCB was associated with 4 of 5 animals dying during the following 12 to 24 h. DCB is fluorescent ($\lambda_{ex}$ 382 nm, $\lambda_{em}$ 416 nm), and confocal microscopy with 0.8 μm optical sections demonstrated that the hydrophobic DCB enters glioma cells and primary astrocytes within 150 minutes and associates with the endoplasmic reticulum (ER). Rapid cell permeation and association with the ER was also observed with ethylisopropylamiloride (EIPA), an NHE1 inhibitor that is also toxic to many cell types. Thus, the lack of specificity, rapid cell permeation, and intracellular effects of DCB and EIPA likely contribute to their general cellular toxicity (Palandoken et al., supra).

Example 4

Synthesis of C(5)-Amino Acid Conjugates

Three C(5)-amino acid conjugates of amiloride were synthesized (see, Scheme 1, compounds 3a-c) using a strategy pioneered by Cragoe et al, for the preparation of C(5)-amino, alkoxy, and thio analogs of amiloride (Cragoe et al., *J. Med. Chem.*, 10:66-75 (1967)). The reaction of C-terminal benzyl-protected amino acids (1a-c) with a guanidine derivative (2) proceeded in the presence of base to regioselectively deliver C(5)-amino acid conjugates. Hydrogenolysis removed the benzyl protection group and afforded conjugates 3a-c in about 30-50% overall yield.

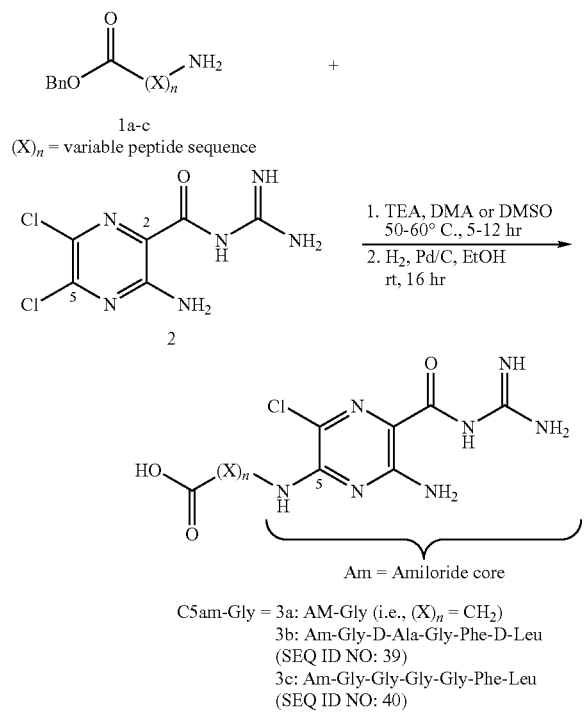

Figure 6:
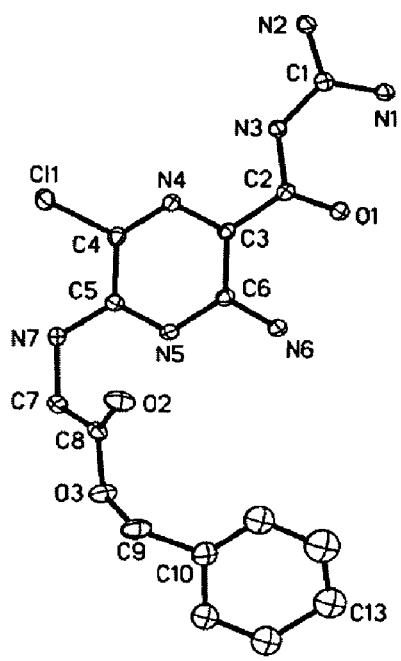
FIG. 6 shows an X-ray crystal structure of C(5)-amino acid conjugate 3a as its benzyl ester.

The conjugates were purified by column chromatography ($SiO_2$) and their structural integrity confirmed by spectroscopic analyses ($^1H$ and $^{13}C$ NMR) as well as mass spectral analysis (LCMS). To unequivocally assign C(5) as the position of amino acid attachment, an X-ray crystal structure of adduct 3a as its benzyl ester was obtained (see, FIG. 6). FIG. 6 clearly shows that the amino acid moiety resides para to the guanidine sidechain.

Example 5

Synthesis of C(2)-Amino Acid Conjugates

A glycine was conjugated to the C(2) guanidine sidechain of amiloride (see, Scheme 2, compound 5) by reaction of Boc-protected glycine (4) with isobutylchloroformate followed by treatment with amiloride. Conjugate 5 was obtained as a hydrochloride salt in 57% overall yield after HCl-mediated deprotection, and was purified by recrystallization. Mass and spectral analyses confirmed the structure.

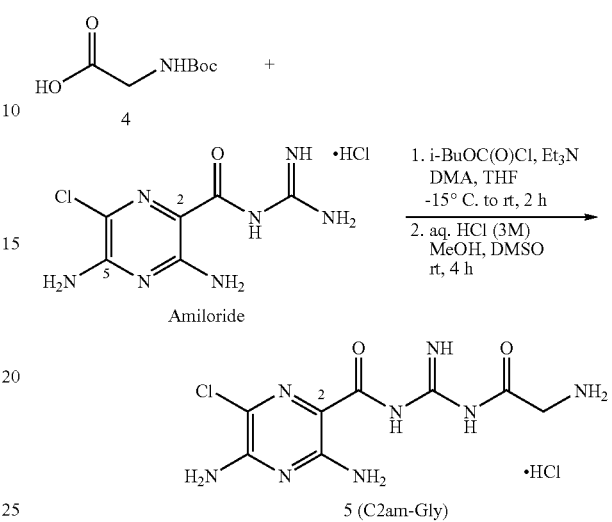

Example 6

Effect of C(5)- and C(2)-Amino Acid Conjugates on Glioma Cell Proliferation and Cell Death C(5)-amiloride glycine conjugate (C5am-Gly) inhibits NHE1 in U87 glioma cells and is antiproliferative. In U87 glioma cells containing BCECF, spectrofluorometric measurements demonstrated that ≦10 µM C5am-Gly (Scheme 1, compound 3a) inhibited NHE1 in gliomas. Manual cell counts with trypan blue demonstrated that C5am-Gly at ≦100 µM inhibited the proliferation of U87 glioma cells to 22% of stage-matched controls by 48 h. The inhibitory activity of C5am-Gly against NCX was tested and a systematic log dose screen of C5am-Gly against a panel of glioma cells and primary astrocytes was performed.

C(2)-amiloride glycine conjugate (C2am-Gly) kills glioma cells. C2am-Gly (Scheme 2, compound 5) killed U87 glioma cells at ≦10 µM concentration within 24 h, as compared to amiloride (500 µM) and DCB (15 µM). Morphologically, dying cells appeared swollen with pyknotic nuclei consistent with necrosis. Quantitative fluorescent microscopy demonstrated that C2am-Gly increased $[Ca^{2+}]_i$ in U87 glioma cells, analogous to the effects of DCB or high doses of amiloride. Further, C2am-Gly is more polar than DCB and was not visualized entering the glioma cells by confocal microscopy after 90-240 minutes. Log dose screening of C2am-Gly using the MTT assay in a panel of 5 glioma cells and primary astrocytes was performed, followed by assessment of its antiproliferative and cytotoxic effects using manual cell counts coupled with trypan blue and its ability to inhibit colony formation.

Example 7

Selective Cleavage of C5am-Gly-Peptide Conjugates

This example shows the results of enzyme degradation assays performed on the C5am-Gly conjugates from Example 4 (see, Scheme 1, compounds 3a-c). Compound 3b is a C5am-Gly-peptide conjugate containing two D-amino acids, and compound 3c is a C5am-Gly-peptide conjugate coupled to a peptide to generate an analog of opioid peptides that cross the blood brain barrier (BBB). The resultant conjugates (compounds 3a-c) were tested for selective cleavage by the brain peptidase enkephalinase (neutral endopeptidase 24.11; Calbiochem) via incubation for 24 h in the presence or absence of the enzyme, and aliquots from the reaction solutions were then analyzed by LC-MS to identify the C5am-Gly conjugate (compound 3a), starting material, and enzymatic cleavage products (see, Scheme 3). As negative control experiments, the conjugates were analyzed following treatment with (1) bovine pancreatic trypsin (Calbiochem) or (2) the buffer solutions without enzymes.

Scheme 3

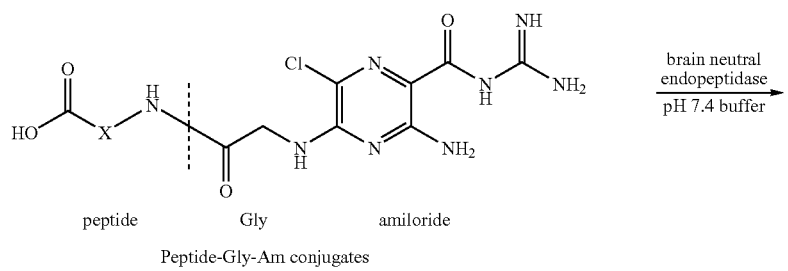

peptide | Gly | amiloride

Peptide-Gly-Am conjugates

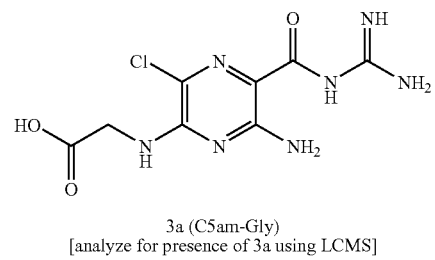

3a (C5am-Gly)
[analyze for presence of 3a using LCMS]

The results from the enkephalinase and trypsin digests of C5am-Gly-peptide conjugates are shown in Table 4. Compound 3a (C5am-Gly) was unaffected by enkephalinase, trypsin, or control (buffer) digestion. Compound 3b (C5am-Gly-D-Ala-Gly-Phe-D-Leu (SEQ ID NO:39)) was not cleaved by either of the enzymes or in the control (buffer) due to the presence of D-amino acids in the peptide. Compound 3c (C5am-Gly-Gly-Gly-Gly-Phe-Leu (SEQ ID NO:40)) was designed to be a peptide analog of the Leu-enkephalin family of peptides and was selectively cleaved by enkephalinase, generating the predicted C5am-Gly cleavage product. However, as a negative control, treatment of compound 3c with trypsin did not generate C5am-Gly.

TABLE 4

C5am-Gly conjugates tested in the LC-MS enkephalinase assay.

| Conjugate (am = amiloride core) | Structure | MS data[a] |
|---|---|---|
| 3a (C5am-Gly) | 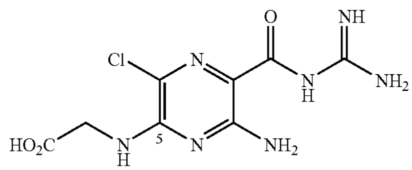 | 288.1 (3a parent)[b]<br>254.1 (M − Cl)[+] |
| 3b (C5am-Gly-D-Ala-Gly-Phe-D-Leu-OH) | 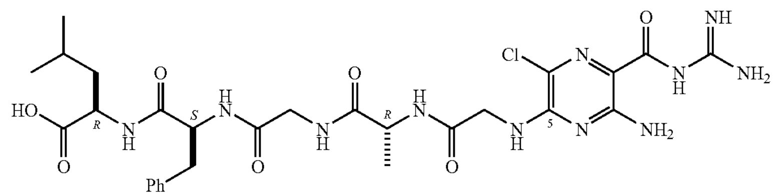 | 676.4 (3b parent)[b]<br>642.4 (M − Cl)[+]<br>288.1 not observed |
| 3c (C5am-Gly-Gly-Gly-Gly-Phe-Leu-OH) | 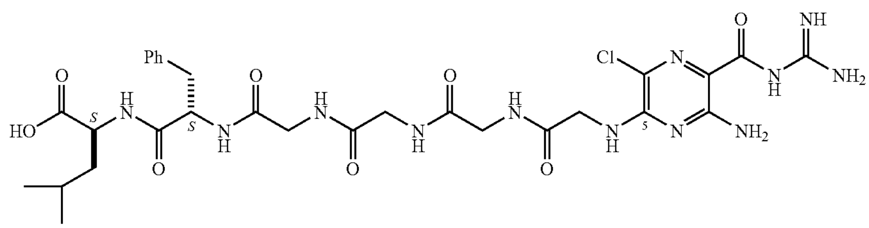 | 719.3 (3c parent)[b]<br>288.1 (C5am-Gly) |

[a] after incubation 6 h;
[b] observable Cl isotope signal

C(5)am-Gly (compound 3a) is considerably more hydrophilic than most amiloride derivatives, a property that restricts its activity to the cell surface (e.g., less toxicity). However, C(5)am-Gly can also be coupled to more hydrophobic peptides, such as a Leu-enkephalin peptide, that are transported across the BBB into the brain (e.g., greater accessibility). The specific enzymatic hydrolysis of compound 3c by enkephalinase demonstrates the feasibility of designing additional C5am-Gly-peptide conjugates that are selectively cleaved by either brain-specific enzymes, tumor-specific enzymes (e.g., matrix metalloproteinases), or enzymes activated during tissue injury (e.g., calpains, caspases) to liberate the more polar C5am-Gly compound.

Example 8

Amiloride-Peptide Conjugates as Prodrugs for NHE Inhibition During Ischemic-Reperfusion Injury This example illustrates that amiloride-peptide conjugates with peptidase cleavage sites are biologically inactive NHE inhibitor prodrugs that can be administered prior to the onset of ischemia and subsequently activated by peptidases selectively expressed by the ischemic tissue for preventing or reducing ischemia-reperfusion injury.

Figure 7:
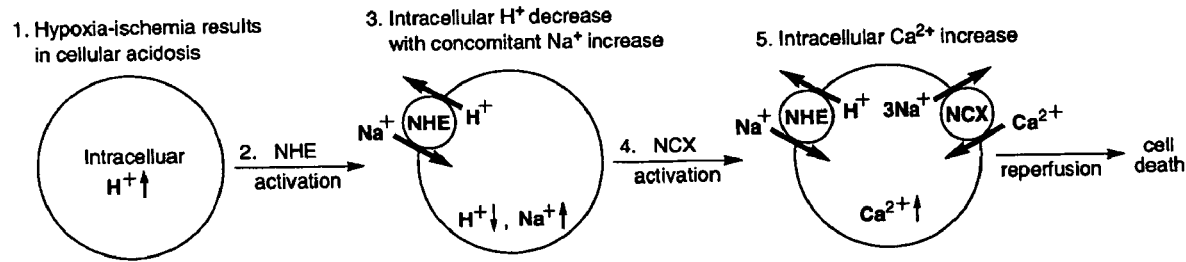
FIG. 7 shows a model for ion transporter activation during ischemia-reperfusion injury.

During an ischemic event, a shift from oxidative to non-oxidative glycolysis causes increased intracellular acidosis in the cells of the ischemic tissue. This reduction in $pH_i$ activates NHE, which increases $[Na^+]_i$ levels (see, FIG. 7) (Orlowski et al., *J. Biol. Chem.*, 272:22373-22376 (1997)). The specifics of normalizing increased $[Na^+]_i$ remain unclear, but include regulation by $Na^+/K^+$ ATPase and sodium-dependent calcium influx ("reverse-mode") by the sodium-calcium exchanger (NCX) (Satoh et al., *Mol. Cell Biochem.*, 242:11-17 (2003)). Persistent activation of the reverse mode of NCX during vascular perfusion further increases $[Ca^{2+}]_i$, which is believed to initiate the irreversible cellular damage observed during ischemia-reperfusion (see, FIG. 7) (Piper et al., *Basic Res. Cardiol.*, 91:191-202 (1996)). Because the sequence of physiological events leading to ischemic-reperfusion injury is initiated by NHE activation, the controlled inhibition of NHE is an area of intense research (Masereel et al., *Eur. J. Med. Chem.*, 38:547-554 (2003)). However, currently available pharmacological inhibitors of NHE are unable to access the ischemic tissue due to severely compromised tissue perfusion during the ischemic event and are thus unsuitable for preventing or reducing the cell death and tissue damage caused by ischemia-reperfusion injury.

The significance of NHE participation in ischemia-reperfusion injury has been shown by demonstrating that NHE inhibitors such as cariporide are effective in preventing cellular damage resulting from cerebral and myocardial ischemia when administered prior to the ischemic event (Klein et al., *Circulation*, 92:912-917 (1995); Scholz et al., *Cardiovasc. Res.*, 29:260-268 (1995); Gumina et al., *Circulation*, 100:2519-2526 (1999), Suzuki et al., *Brain Res.*, 945: 242-248 (2002)). In a recent human clinical study by Tardif et al., *Can. J Cardiol.*, 20:317-322 (2004), cariporide was administered intravenously prior to coronary artery bypass graft surgery and its cardioprotective effects were shown to be greatest when the drug was already present in the myocardial tissue prior to reperfusion. However, as discussed above, a major limitation in the delivery of NHE inhibitors such as cariporide to tissues during the early phases of ischemia is the lack of adequate perfusion. As such, this example describes the synthesis of biologically inactive NHE inhibitor prodrugs that would reside in tissues and be transformed into an active NHE inhibitor during an ischemic event. For example, when the inactive NHE inhibitor prodrugs are administered prior to the onset of ischemia, cellular endopeptidases that are activated during the early stages of ischemia (see, e.g., Denault et al., Chem. Rev., 102:4489-4500 (2002)) can selectively cleave the inactive prodrugs to yield potent NHE inhibitors. Activation of the prodrugs by peptidases eliminates drug delivery concerns, while NHE inhibition is highly specific, low in toxicity, and occurs immediately subsequent to the ischemic event.

Figure 8:
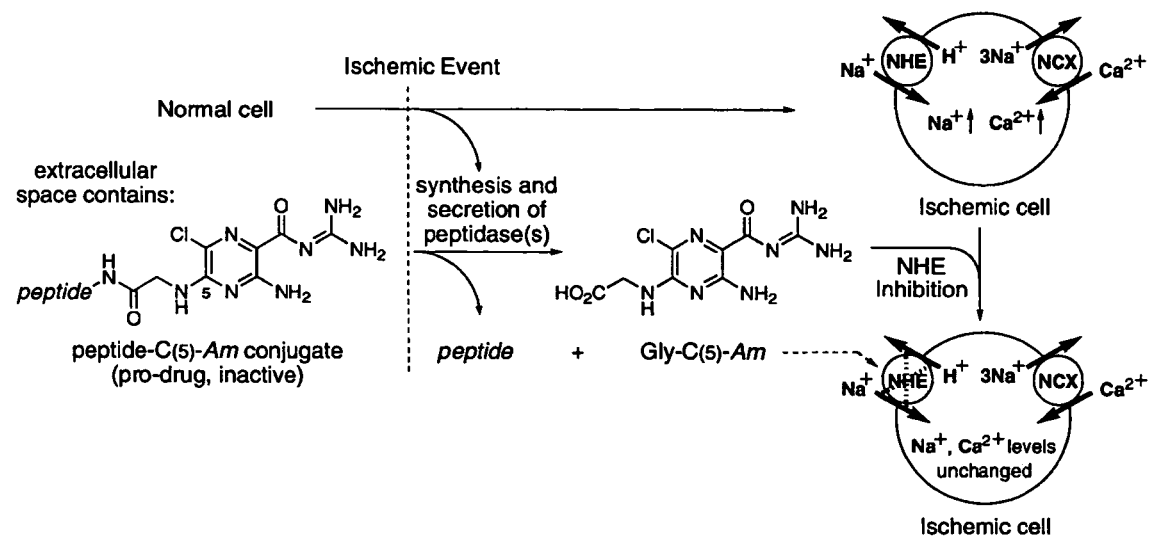
FIG. 8 shows a model of the amiloride-peptide conjugates of the present invention being enzymatically activated to inhibit sodium-proton exchange.

FIG. 8 depicts the strategy for preventing or reducing ischemia-reperfusion injury using the NHE-inhibiting amiloride-peptide prodrugs of the present invention. As shown in FIG. 8, an inactive amiloride-peptide prodrug (e.g., a C(5)am-peptide conjugate) is administered to a subject in need thereof (e.g., a subject at risk for an ischemic event) and resides in the extracellular space of a normal cell. During an ischemic event, the synthesis and secretion of peptidases by an ischemic cell selectively cleaves the amiloride-peptide conjugate and releases the active NHE inhibitor (e.g., C(5) am-Gly), which inhibits NHE on the ischemic cell surface and prevents or reduces the injury associated with ischemia-reperfusion. This strategy offers two distinct advantages: (1) specific peptide sequences permit selective cleavage by peptidases for site-specific tissue activation of amiloride-peptide prodrugs; and (2) the hydrophilic nature of the active NHE inhibitor released from the amiloride-peptide prodrug deters intracellular permeation and limits the inhibitor's action to cell surface transporters. Although it is preferable that the amiloride-peptide prodrugs are inactive prior to selective cleavage by a peptidase, weakly active prodrugs are also within the scope of the present invention.

Methods

Chemistry. The synthesis of compounds 3a-c is described in Scheme 1, above. Compound 3d was also prepared according to Scheme 1, except that the peptide sequence was Gly-Gly-Gly-Phe-Leu (SEQ ID NO:41). Peptides were purchased from Genetel Laboratories (Madison, Wis.) as trifluoroacetic acid (TFA) salts. Amiloride was prepared according to Cragoe et al., J. Med. Chem., 10:66-75 (1967). NMR spectra were recorded with a Varian Inova spectrometer ($^1$H at 400 MHz, $^{13}$C at 100 MHz). Mass spectral analyses (LC-MS/ESI) were performed at the University of California, Davis Molecular Structure Facility using a Thermo Finnigan LCQ fitted to an electrospray source and ion trap mass analyzer with an ABI 120A HPLC. Samples were injected onto a Vydac HPLC column (300 Å, 250×1 mm) and gradient eluted (5% $CH_3CN$ to 90% $CH_3CN$) over 1 hour with 0.1% aqueous formic acid as the secondary solvent prior to spraying (100 µL/min, 220° C., 50µ sheath gas, +3.2 kV needle voltage).

Enzyme digestion. Endopeptidase 24.11 (neutral, porcine kidney) and trypsin (bovine pancreas) were purchased from CalBiochem (San Diego, Calif.) and used as received. Enzymatic cleavage experiments using endopeptidase 24.11 were conducted at 25° C. in a pH 7.4 Tris buffer (150 mM NaCl, 50 mM Tris, 0.1% Triton X-100) as recommended by the manufacturer (see also, Barnes et al., J. Neurochem., 64:1826-1832 (1995), Gafford et al., Biochemistry, 22:3265-3271 (1983)). Similarly, trypsin cleavage experiments were conducted at 25° C. in pH 7.4 Dulbecco's phosphate buffered saline (Gibco; Grand Island, N.Y.). The digestion reactions included 10 µM of the amiloride-peptide conjugate and 10 units of enzyme in 250 µL of buffer. Direct aliquots were analyzed by LC-MS/ESI following a 24 hour incubation period.

Intracellular pH Measurements. U87 glial cells were grown on glass coverslips and incubated for 30 minutes at 37° C. with the pH-sensitive dye, 2',7'-bis(2-carboxyethyl)-5(6)-carboxyfluorescein-AM (BCECF-AM; Molecular Probes, OR). Cells were rinsed with HEPES Ringer buffer twice and maintained at 37° C. for an additional 15 minutes to permit intracellular hydrolysis of the AM ester; trapping BCECF within the cells. Cells on coverslips were placed in a Hitachi F2000 fluorescent spectrophotometer and excited at 440 and 507 nm with fluorescent emissions recorded at 535 nm (Hegde et al., J. Pharmacol. Exp. Ther., 310:67-74 (2004)).

Fluorescence Microscopy. Visualization of intracellular fluorescent amiloride conjugates was conducted using high-speed imaging, epifluorescent microscopy. Excitation light was provided by a xenon arc lamp coupled to the Polychrome IV scanning monochromator (Till Photonics; Grafelfing, Germany) that alternately excites with different wavelengths. Excitation light was delivered by fiber optics to cells through the epifluorescence port of a Nikon E600 microscope coupled to a Nikon Fluor 60× water immersion lens. The detector was an Orca II-ER CCD digital camera (Hamamatsu USA; Bridgewater, N.J.), which is controlled by C-Imaging Simple PCI software (Compix; Cranberry Township, Pa.).

Intracellular emission intensities were collected in regions of interest (ROI) from an average of 4-8 cells/field using Simple PCI imaging software. Emission intensities were subtracted from mean intracellular intensities measured in glioma cells prior to the addition of the fluorescent amiloride conjugates. Statistical significance at $P<0.05$ and $P<0.01$ levels between compound 3a, amiloride, and EIPA were evaluated nonparametrically using the Wilcoxon rank sum test (Sigma Statview v.3.0; Jandel Scientific; San Rafael, Calif.) as described in Vali et al., J. Cell. Physiol., 185:184-199 (2000). Images were captured as TIFF files (C-imaging Simple PCI software), and light and fluorescent images of the same field were imported in Photoshop 6.0 and vector graphics added using Illustrator 9.0.1 (Adobe; San Jose, Calif.).

Results

Enzyme Digestion Study. Compounds 3a-d were each incubated at 25° C. with 10 units of enkephalinase (endopeptidase 24.11) to determine their susceptibility towards enzymatic cleavage. Reaction aliquots were taken following a 24 hour incubation period and analyzed directly by LC-MS/ESI (Thermo Finnigan LCQ) for the presence of the starting material and the targeted cleavage product, compound 3a (C5am-Gly). As shown in Table 5, compound 3c released compound 3a following endopeptidase digestion. Since there are no basic amino acid residues in compounds 3a-d, trypsin was employed as a negative control to ensure that any observed cleavage products could be ascribed only to endopeptidase-specific interactions (Jackson, Protein Science, 8:603-613 (1999)). Trypsin digestion did not cleave any of the amiloride conjugates with the exception of 3c (see, Table 5).

TABLE 5

Enzymatic digestion of compounds 3a–3d with enkephalinase or trypsin.

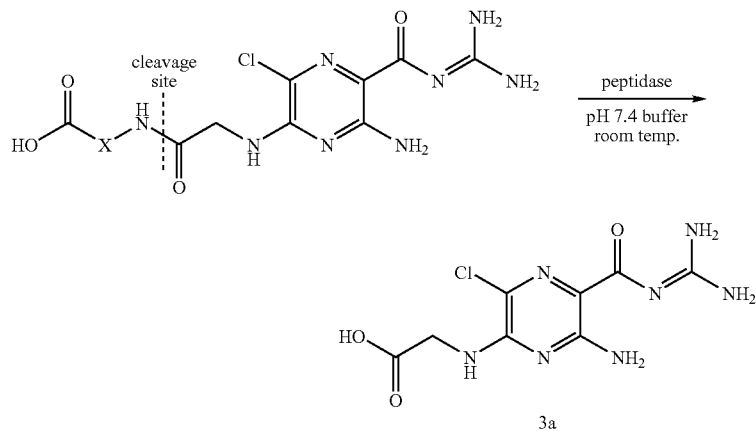

| Compound | Peptidase | LC-MS Fragments[1] | Conclusion |
| --- | --- | --- | --- |
| 3a | Enkephalinase | 254.1 (MH$^+$ – Cl) | Enkephalinase resistant |
| 3a | Trypsin | 254.1 (MH$^+$ – Cl) | Trypsin resistant |
| 3b | Enkephalinase | 676.3 (parent, MH$^+$)<br>288.1 not observed | Enkephalinase resistant |
| 3b | Trypsin | 676.3 (parent, MH$^+$)<br>288.1 not observed | Trypsin resistant |
| 3c | Enkephalinase | 288.1 (3a MH$^+$)<br>254.1 (3a MH$^+$ – Cl)<br>719.3 (parent, MH$^+$) not observed | Enkephalinase-mediated release of 3a |
| 3c | Trypsin | 215.4[2]<br>288.1 not observed | Trypsin-mediated cleavage of the Gly-Am linkage |
| 3d | Enkephalinase | 628.4 (MH$^+$ – Cl)<br>288.1 not observed | Enkephalinase resistant |
| 3d | Trypsin | 628.4 (MH$^+$ – Cl)<br>288.1 not observed | Trypsin resistant |

[1]Principal LC-MS fragments observed on direct injection of an aliquot sampled from the digestion at 24 h.
[2]Fragment corresponding to the pyrazine product obtained on cleavage of the peptide from the Am ring.

Evaluation of NHE Inhibition by Amiloride Conjugates. NHE inhibition by compounds 3a and 3c was evaluated using intracellular pH (pH$_i$) measurements in the U87 human glial cell line (Hegde et al., supra). Cells loaded with BCECF were then acidified using the ammonium chloride pre-pulse method (Roos et al., *Physiol Rev*, 61:296-434 (1981)). The subsequent sodium-dependent recovery of pH$_i$ by these cells in the absence of bicarbonate was monitored using a spectrofluorometer. Sodium-dependent proton extrusion in U87 glial cells and in primary astrocytes is mediated by the type 1 sodium proton exchanger (NHE1) (McLean et al., supra; Hegde et al., supra) and was monitored in the presence or absence of compound 3a or 3c. As shown in Table 6, concentrations of these compounds capable of inhibiting 50% of NHE1 activity (IC$_{50}$) were determined and compared with the known NHE inhibitors, amiloride and cariporide.

TABLE 6

IC$_{50}$ values for amiloride, cariporide, and compounds 3a and 3c.

| NHE Inhibitor Drug | IC$_{50}$ (µM) +/– SD (NHE inhibition) | Relative Potency |
| --- | --- | --- |
| Amiloride | 50 ± 27 | 1 |
| Cariporide | 0.074 ± 0.072 | 676 |
| C5am-Gly (3a) | 13 ± 7 | 4 |
| C5am-Gly-Gly-Gly-Gly-Phe-Leu-OH (3c) | No inhibition < 100 µM | <0.5 |

The IC$_{50}$ of amiloride depends upon external [Na]$^+$, and its value in U87 glial cells (50 µM) is modestly higher than those described in the U118 glial cell line (17 µM) and in primary rat astrocytes (6 µM) (McLean et al., supra). The IC$_{50}$ of cariporide (74 nM) is comparable to values published using CHO cell lines (30 nM) (Kawamoto et al., *Eur. J. Pharmacol.*, 420:1-8 (2001)). Compound 3c did not inhibit NHE1 in U87 glial cells and concentrations exceeding 100 µM produced interfering fluorescent background. By contrast, compound 3a was at least 4-fold more potent than the parent compound, amiloride, but less active than the benzoylguanidine derivative, cariporide. The inhibition of NHE1 was rapidly reversed following the removal of compound 3a, in contrast to the slow and incomplete recovery observed with amiloride and ethylisopropylamiloride (EIPA). This result indicated that intracellular permeation by the more hydrophilic compound 3a differed significantly from that of the more hydrophobic amiloride and the C5am alkyl homolog EIPA.

Figure 9:
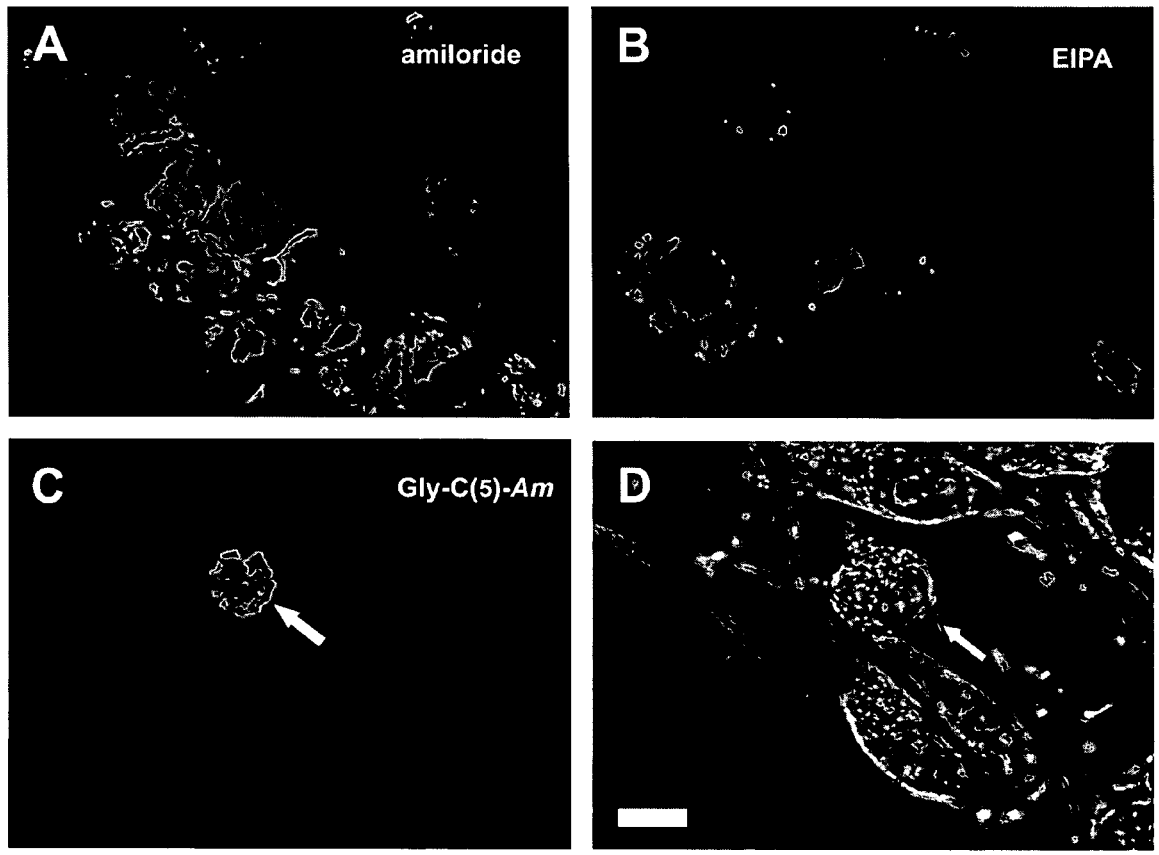

Intracellular Translocation of Amiloride Conjugates. The intracellular translocation of compound 3a into U87 cells was compared with amiloride and EIPA (see, FIG. 9). These three amiloride derivatives are intrinsically fluorescent when excited at 380 nm with 510 nm emission, and their presence inside cells can easily be visualized using a variable wavelength, quantitative fluorescent microscopy system (Kraut et al., *Anal. Biochem.*, 214:413-419 (1993)). Their relative molar absorptivity constants measured with a spectrofluorometer are quite comparable so that intracellular accumulation of amiloride, EIPA, and compound 3a could be visualized using fluorescent microscopy. For example, the relative molar absorptivity constants determined at 380 nm excitation and 510 nm emission for amiloride, EIPA, and compound 3a are 1, 2, and 13, respectively.

U87 cells were incubated with 50 µM of compound 3a, amiloride, or EIPA for 0, 90, and 180 minutes, washed twice at 22° C. with isotonic phosphate buffer, and intracellular fluorescence then was visualized by 380 nm excitation and 510 nm emission. These studies were repeated three times for each compound with the same results. Within 90 minutes, there was intracellular accumulation of amiloride and EIPA that was associated with the endoplasmic reticulum (FIGS. 9A and 9B). By contrast, no intracellular fluorescence above mean intracellular background was detected in intact glioma cells with compound 3a following incubations of either 90 minutes or 180 minutes. Compound 3a demonstrated significant intracellular fluorescence only in the rare dying and dead cells having increased membrane permeabilities. These dying and dead cells were identified by their co-staining with trypan blue, a visible dye that is excluded by viable cells (FIGS. 5C and 5D; Hegde et al., supra). The intracellular detection of compound 3a fluorescence only in trypan blue positive (i.e., dead) cells further verified that the conjugate remains excluded from viable U87 cells after 180 minutes, relative to amiloride and EIPA.

Discussion

There is great interest in the development of inhibitors of sodium-proton (NHE) and sodium-calcium (NCX) exchangers to limit ischemic tissue damage produced during vascular reperfusion. A fundamental impediment to the field has been the delivery of these compounds to poorly vascularized tissues during the early phases of ischemic injury when NHE/NCX inhibition would be most beneficial (Masereel et al., *Eur. J. Med. Chem.*, 38:547-554 (2003), Tardif et al., *Can. J Cardiol.*, 20:317-322 (2004)). Consequently, the novel strategy of using the amiloride-peptide conjugates described herein as inactive prodrugs that can be enzymatically activated to generate inhibitors of NHE overcomes the limitations of current therapies for ischemia-reperfusion cytotoxicity. In particular, the amiloride-peptide conjugate prodrugs are capable of residing in tissues prior to the onset of ischemia. Peptidases generated during the early phases of ischemia then selectively cleave the inactive prodrug and unmask an active NHE inhibitor molecule. This approach is advantageous due to the selective inhibition of NHE in ischemic tissues with prodrug activation during a critical phase where early NHE inhibition can limit the cell death caused by sodium-mediated $Ca^{2+}$ overload (Satoh et al., *Mol. Cell Biochem.*, 242:11-17 (2003)). In addition, the prodrugs can be converted to small, water-soluble molecules whose biological activities are restricted to cell surface exchangers, thereby limiting unintended intracellular toxicity (Numata et al., *J. Biol. Chem.*, 276:17387-17394 (2001)).

The peptide sequences in compounds 3b-3d were selected to mimic analogs of $^5$[Leu]-enkephalin, a member of the opioid neuropeptide family, which has the amino acid sequence Tyr-Gly-Gly-Phe-Leu (SEQ ID NO:42) (Gorin et al., *J. Med. Chem.*, 23:1113-1122 (1980)). Amiloride serves as a $^1$[Tyr] surrogate in the conjugate panel. The enzymatic cleavage of enkephalin by enkephalinase (e.g., neutral endopeptidase 24.11) is well characterized and known to occur selectively between adjacent Gly residues (Rogues et al., *Pharmacol. Rev.*, 45:87-146 (1993)). Compound 3b was designed as a negative control as it contains two D-amino acids in the peptide sequence instead of a Gly-Gly motif to ensure resistance to enkephalinase-mediated cleavage. Enzyme-mediated cleavage of compound 3d was designed to generate compound 3a, provided that the amiloride substitution for $^1$[Tyr] does not alter the Gly-Gly recognition by enkephalinase. The possibility that the Tyr-to-amiloride substitution could alter Gly-Gly substrate recognition by enkephalinase led to the insertion of an additional Gly in the peptide sequence; thus the rationale for compound 3c.

The enzyme digestion data demonstrated that compound 3a was stable and persisted in the presence of both enkephalinase and trypsin (see, Table 5). Compound 3b was also resistant to peptidase cleavage by either enzyme due to the D-amino acid substitutions. Digestion of compound 3d with enkephalinase did not liberate compound 3a, likely because of steric interference by the amiloride residue. However, the inclusion of an additional Gly in the peptide sequence to create compound 3c resulted in a complete digestion by enkephalinase with the release of compound 3a. The additional Gly in compound 3c appears to ameliorate the adverse effect of the Tyr-to-amiloride substitution in compound 3d, thereby restoring enkephalinase specificity.

The enzymatic specificity for release of compound 3a by enkephalinase is supported by the observation that none of the conjugates released compound 3a when digested with trypsin. The digestion of compound 3c by trypsin did not release compound 3a, indicating that the C2-guanidine moiety of the amiloride terminus in compound 3c mimics L-arginine. In addition, the hexapeptide in compound 3c may be capable of forming the requisite peptide loop intermediate for trypsin cleavage (Jackson, *Protein Science*, 8:603-613 (1999)), unlike the shorter pentapeptide found in compound 3d. These enzymatic studies illustrate the feasibility of using a targeted enzyme-mediated strategy to release compound 3a from the amiloride-peptide prodrugs.

The $IC_{50}$ values determined in the glial cell study shown in Table 6 clearly illustrate that compound 3a is a more potent NHE inhibitor than amiloride. By contrast, compound 3c was essentially inactive. The relative $IC_{50}$ values for these two conjugates confirm the ideal activity difference between an inactive peptide prodrug (e.g., compound 3c) and its corresponding active drug form (e.g., compound 3a), which acts as a potent NHE inhibitor.

During the course of the $IC_{50}$ determinations, washout of compound 3a restored the steady-state $pH_i$ of U87 cells in less than 1 min. By contrast, amiloride washout was associated with a prolonged and an incomplete recovery of steady-state $pH_i$. These observations indicate that compound 3a is more effectively removed from the NHE protein than its more hydrophobic parent compound, amiloride. This effect is predicted by their respective cLogP values (i.e., cLogP values for amiloride (−2.22) vs. compound 3a (−6.23, calculated) indicate a substantial difference in hydrophilicity), which also predicts that compound 3a would be less likely to permeate cells, unlike amiloride or EIPA (Kraut et al., *Anal. Biochem.*, 214:413-419 (1993)). The intrinsic fluorescence of the amiloride conjugates permitted the use of a quantitative fluorescent microscopy system to detect their intracellular accumulation. Fluorescent microscopy failed to detect the intracellular accumulation of compound 3a after 180 minutes, in contrast to the rapid cell permeation observed with amiloride and EIPA (see, FIG. 9). The permeation properties of the more polar compound 3a restricts its activity to cell surface exchanger proteins while limiting non-specific intracellular toxicity, which have been observed with amiloride and EIPA.

This example has demonstrated the conversion of an inactive amiloride-peptide conjugate to a potent NHE inhibitor under enzyme-specific conditions. In particular, compound 3a is the first amino acid analog of amiloride that displays several desirable pharmacological and chemical properties for an NHE inhibitor. As a result, the prodrug strategy described herein finds general application as a new therapeutic approach for preventing or reducing the damage caused by ischemia-reperfusion injury. Enkephalinase is present in the brain's cerebrospinal fluid and has been shown to degrade exogenously administered opioid peptides (Molineaux et al., *J. Neurochem.*, 55:611-618 (1990)). Likewise, peptide sequences that are substrates for endopeptidases specifically activated during the early stages of brain or heart ischemia-reperfusion injury can be conjugated to amiloride to generate inactive prodrugs. Furthermore, the selective activation of an NHE inhibitor prodrug by glioma-specific endopeptidases assists with the regional treatment of intracellular edema associated with these aggressive intracerebral tumors (Gorin et al., *Acta Neuropathol.*, 107:235-244 (2004)) and produced during cerebral ischemia and traumatic brain injury.

The prodrug strategy described herein can be adapted to synthesize C2-amino acid and peptide amiloride conjugates, which demonstrate dual NHE and NCX inhibitory activities. Such prodrugs can complement the C5-amino acid and peptide amiloride conjugates to even more effectively limit ischemia-reperfusion tissue damage.

Example 9

Identification of the Cellular Mechanisms by which Inhibition of NCX and NHE1, Respectively, Produce Glioma Cell Death and Inhibit Proliferation This example illustrates experiments to test the proposal that inhibition of the calcium efflux mode of NCX by the C2am-Gly conjugate results in toxic or near-toxic accumulations of intracellular calcium ($[Ca^{2+}]_i$).

Experiment #1: Determine whether amiloride derivatives that inhibit $Na^+$-dependent $Ca^{2+}$ efflux kill glioma cells primarily by increasing $[Ca^{2+}]_i$ to cytotoxic levels.

Rationale: Ionomycin, a calcium ionophore, kills glioma cells within 90-180 minutes. The time course and magnitude of $[Ca^{2+}]_i$ elevations preceding ionomycin-induced cell death can be compared with changes in $[Ca^{2+}]_i$ levels produced by NCX inhibitors.

Experimental Design: The magnitude and time course of $[Ca^{2+}]_i$ elevation produced by amiloride, DCB, and C2am-Gly in U87 glioma cells loaded with fura-2FF can be determined. The time course and magnitude of $[Ca^{2+}]_i$ elevation produced by ionomycin can be measured in U87 glioma cells and astrocytes. The results obtained with fura-2AM (see, FIG. 2B) can be compared with that for the fura-2FF AM ester. The high levels of $[Ca^{2+}]_i$ produced with NCX inhibitors indicate that more accurate quantification could be obtained using an indicator dye with lower calcium affinity (Hyrc et al., *Cell Calcium*, 27:75-86 (2000)). For these temporal studies, cells can be loaded with fura-2FF and imaged using a multi-wavelength inverted fluorescent microscope equipped with a quantitative high speed imaging system as previously described (Vali et al., *J. Cell Physiol.*, 185:184-99 (2000)). The effect of ionomycin on $[Ca^{2+}]_i$ can be compared with that produced by the NCX inhibitors DCB and C2am-Gly.

The dose-dependent inhibition of NCX by DCB and C2am-Gly in U87 gliomas can also be measured. The relative $IC_{50}$ values of these compounds can be compared with those of cariporide and C5am-Gly. Cariporide is a selective inhibitor of NHE1 and C5am-Gly is predicted to inhibit NHE1>>NCX. The dose-dependent inhibition of NCX can be determined in a spectrofluorometer using glioma cells containing fura-2FF. Briefly, cells on coverslips are perfused with sodium-free buffer where non-permeable, N-methyl D-glucamine (NMDG) is used to replace external sodium. Incubation of glioma cells or astrocytes with FCCP causes a persistent elevation in $[Ca^{2+}]_i$ that resolves following the reintroduction of external sodium in the perfusate (Kopper et al., *Amer. J. Physiol. Cell Physiol.*, 282:C1000-1008 (2002)). The inclusion of NCX inhibitors at differing concentrations in the sodium-containing perfusate permits determination of their relative $IC_{50}$ values in the presence of external calcium.

In addition, the morphological similarity between glioma cell death produced by high dose amiloride, DCB, C2am-Gly, and ionomycin can be determined using manual cell counts coupled with Sytox Green. Sytox Green, a stain which binds to cytoplasmic and nuclear nucleic acids, is used to assess morphological changes associated with apoptosis and necrosis (Bien et al, *J. Neurotrauma*, 16:153-163 (1999)). Manual cell counts with trypan blue can be employed to quantify the amount of glioma cell death produced by ionomycin and the amiloride derivatives at 24, 48, and 72 h. Morphological changes associated with cell death can be examined by staining with Sytox Green. The type of cell death produced by the amiloride derivatives can then be compared with the predominantly caspase-independent, morphologically necrotic cell death observed with amiloride. A shared cell death mechanism increases the likelihood that the amiloride derivatives are killing glioma cells through common cellular mechanisms. Whether inhibition of caspase activation or calpain activation affects the magnitude of cell death can also be examined as follows: treated glioma cells can be pre-incubated with the pan-caspase inhibitor z-Val-Ala-Asp-fluoromethyl ketone (zVAD.fmk) or with calpeptin, a cell permeable inhibitor of 1'-calpain and mu-calpain activation. zVAD.fmk-treated and calpeptin-treated cells can be compared with stage-matched cells treated with either a caspase negative control peptide (zFA.fmk) or a calpeptin negative peptide control (Novagen Cat. No. 208902).

Moreover, whether depletion of $[Ca^{2+}]_i$ in glioma cells reduces the cytotoxic efficacies of the amiloride derivatives to kill glioma cells can be determined. Measurements of $[Na^+]_i$, $[Ca^{2+}]_i$, and the resting membrane potential in glioma cells indicate that the calcium efflux mode of NCX is activated when external calcium is <2 µM, based upon the Goldman Field equation. Therefore, cells can be incubated for 6-12 h in calcium-free medium that includes equimolar and isotonically balanced replacement with a $CaEGTA/K_2EGTA$-buffered solution (Bers et al., *Methods Cell Biol.*, 40:3-29 (1994)). The ratio of the two 10 mM EGTA buffers can be adjusted, based on temperature, pH, and ionic strength to yield known concentrations of $[Ca^{2+}]_{ext}$. The reduction of levels of $[Ca^{2+}]_i$ can be measured in glioma cells containing fura-2 using quantitative fluorescent microscopy. As necessary, the depletion of cytosolic free calcium by NCX can be adjusted by manipulating $[Ca^{2+}]_{ext}$ or by isotonically increasing $[Na^+]_o$. The effects of amiloride ($\geq$500 µM), DCB ($\geq$20 µM), and C2am-Gly ($\leq$10 µM) on the proliferation and cell death of calcium-depleted glioma cells can be compared with stage-matched, treated cells maintained in control medium using manual cell counts with the trypan blue exclusion assay. NHE1 inhibitors, including cariporide (80 µM) and amiloride (20 µM), can be included as negative controls.

Results: Growing U87 glioma cells for 12 h in calcium-free DMEM-HEPES with 3:1 $K_2EGTA:CaEGTA$ (0.35 µM at 37° C., pH 7.4) reduced the proliferative rate by 22% but did not affect cell viability. $[Ca^{2+}]_{ext}$ in the buffers were verified using atomic absorption. Incubating cells maintained in calcium-depleted medium with 500 µM amiloride reduced the drug's cytotoxicity by 44% by 48 h, as compared with treated cells in control medium. Calcium is highly buffered by subcellular organelles so that it is important to measure $[Ca^{2+}]_i$ in cells.

Experiment #2: Determine whether inhibition of sodium-mediated calcium efflux (i.e., the forward mode of NCX) is sufficient to cause glioma cell death.

Rationale: SEA0400 is a selective inhibitor of NCX without any NHE1 inhibitory activity (Matsuda et al., *J. Pharmacol. Exp. Ther.*, 298:249-56 (2001)). Whether SEA0400 has cytotoxic and anti-proliferative effects on glioma cells can be determined.

Experimental Design: A log dose screening of SEA0400 on a panel of 5 glioma cells and astrocytes with the MTT assay can be performed and the presence of a reduction in the number of viable glioma cells compared with stage-matched, vehicle-treated control cells can be determined. Concentrations of SEA0400 based upon the log dose screen can be selected and manual cell counts coupled with trypan blue can be employed to determine whether SEA400 has antiproliferative and cytotoxic effects. U87 glioma cells can be loaded with fura-2FF treated with SEA0400 and the time course and magnitude of $[Ca^{2+}]_i$ can be measured using quantitative fluorescent microscopy. Changes in cell viability, proliferation, and $[Ca^{2+}]_i$ levels produced by SEA0400 can be compared to those produced by DCB and the C2am-Gly and C5am-Gly conjugates.

Whether SEA0400 kills glioma cells by a calcium-dependent mechanism can then be determined. Cytosolic calcium can be depleted in U87 glioma cells in a low calcium medium buffered isotonically with CaEGTA/K$_2$EGTA. The cytotoxicity of SEA0400 can be compared to treated cells in control medium. Whether glioma cells treated with SEA0400 have altered their ability to form colonies compared with vehicle-treated, stage-matched controls can also be examined.

Electrical stimulation of cardiomyocytes obtained from transgenic mice that are homozygous for NCX inactivation has demonstrated that SEA0400 inhibits inward calcium currents besides those attributable to NCX (Reuter et al., *Circ. Res.*, 91:90-92 (2002)). These currents are expected to be small, but can be blocked by 0.5 mM $Cd^{2+}$ or 10 mM $Co^{2+}$ so that their contribution to $[Ca^{2+}]_i$ levels can be examined.

Experiment #3: Determine whether NHE1 inhibition augments the glioma cytotoxicity associated with NCX inhibition.

Rationale: Amiloride ($\geqq 500$ µM) and DCB ($\geqq 20$ µM) kill gliomas at concentrations that inhibit both NCX and NHE1. However, either NHE1 inhibition alone or direct acidification impairs glioma cell proliferation. As such, direct intracellular acidification would be comparable to any augmentation in glioma cytotoxicity produced by inhibition of NHE1.

Experimental Design: Whether the addition of a selective NHE1 inhibitor, cariporide, shifts the log dose curve of trypan blue using the MTT assay can be determined. Log dose screening can be followed by manual cell counts coupled with Sytox Green to compare the antiproliferative and cytotoxic effects of a combination of SEA0400 and cariporide with those produced by SEA0400 or DCB. Whether reducing intracellular pH by acidifying the medium to pH 6.6 (pH$_i$ 6.9) contributes to the possible cytotoxicity of SEA0400 with an observed shift of the log dose curve can be determined using the MTT assay. A concentration range can be selected based upon log dose screening of SEA0400. The antiproliferative and cytotoxic effects of SEA0400 at pH$_{ext}$ 6.6 with SEA0400 in control medium can then be determined using manual cell counts coupled with trypan blue. As indicated by manual cell counts, the colony forming ability of glioma cells treated with SEA0400 compared to vehicle-treated, stage-matched controls can be examined. As cariporide could have additional unknown pharmacological effects, a direct reduction of pH$_i$ in glioma cells to a pH$_i$ of 6.9 can be performed by acidifying the medium, and the effects of such direct intracellular acidification can be compared to those produced by cariporide. The cytotoxicity of SEA0400 with acidified cells can also be compared to that of SEA0400 control cells.

Experiment #4: Determine whether NHE1 inhibition is associated with calcium mobilization from intracellular stores.

Rationale: U87 glioma cells have basal levels of $[Ca^{2+}]_i$ that are 5-fold higher than those of primary astrocytes. The identification of calcium buffering mechanisms in glioma cells that become decompensated in the setting of NCX and NHE1 inhibitors could identify additional therapeutic targets.

Experimental Design: Levels of $[Ca^{2+}]_i$ can be measured in glioma cells with fura2-FF and treated with cariporide, SEA0400, or a combination of the two drugs. The time course of the calcium measurements using quantitative fluorescent microscopy can be based upon the cell death determinations from Experiment #3. If cariporide is found to augment $[Ca^{2+}]_i$ in the presence of NCX inhibition, then the effects of SEA0400 with cells acidified to pH$_i$ 6.9 can be compared to those produced by a combination of SEA0400 and cariporide. The elevated levels of $[Ca^{2+}]_i$ in glioma cells observed in the preliminary studies using fura-2AM can be quantitated using calcium-sensitive dyes having a lower affinity constant. Fura-2FF is relatively pH-insensitive and has a lower $K_d$ ($K_d$=6 µM) for calcium than fura-2 ($K_d$=0.25 µM). Fura-2FF is ratiometric and has a wider dynamic range that can better accommodate increases in $[Ca^{2+}]_i$ to 1000 nM (Hyrc et al., *Cell Calcium*, 2:775-786 (2000)). As such, levels of $[Ca^{2+}]_i$ in cells loaded with either fura-2 or Fura-2FF can be compared.

Experiment #5: Determine whether mobilization of calcium from intracellular stores is associated with reduced cellular ATP levels.

Rationale: Cytosolic ATP levels in hypoxic and ischemic glioma cells rely primarily upon glycolysis (Erecinska et al., *J. Neurosci.*, 11:2410-2421 (1991); Silver et al., *Glia*, 21:35-45 (1997)). However, ATP levels are decreased as a result of impaired glycolysis associated with NHE1 inhibition. Further, ATP-dependent release of calcium from mitochondrial or endoplasmic stores could enhance the cytotoxicity of NCX inhibitors on glioma cells. These studies can identify additional therapeutic targets.

Experimental Design: Total cellular levels of ATP, ADP, AMP, and P$_i$ can be measured at 0, 6, 12, 24, and 48 h in U87 glioma cells following incubation with the NHE1 inhibitor cariporide. The effects of cariporide on levels of ATP, ADP, AMP, and P$_i$ can be compared with levels in cells treated with SEA0400 or a combination of SEA0400 and cariporide. The metabolites can be normalized to cellular protein levels and compared to stage-matched controls. In separate experiments, pH$_i$ and $[Ca^{2+}]_i$ levels can be measured using the same treatment protocols to compare how ionic changes temporally correspond with alterations in cellular energy.

To simulate a hypoxic-ischemic tumor environment, U87 glioma cells with either impaired glycolysis or impaired oxidative phosphorylation can be studied. Glycolysis can be inhibited by culturing the glioma cells for 12 h in DMEM-HEPES medium, pH 7.4, where glucose has been replaced with 2-deoxyglucose (Wu et al., *Glia*, 21:315-326 (1997); Donoso et al., *J. Physiol.*, 448:493-509 (1992)). In separate experiments, oxidative metabolism in U87 glioma cells can be inhibited at either complex I, e.g., with roteonone, or complex III, e.g., with antimycin. Cellular levels of ATP, ADP, AMP, and $P_i$ can be measured in these metabolically compromised glioma cells in the presence or absence of cariporide, SEA0400, and a combination of both drugs. In parallel experiments, the $pH_i$ can be measured in glioma cells loaded with BCECF, while $[Ca^{2+}]_i$ levels can be determined in cells loaded with fura-2FFAM. Changes in ATP, ADP, AMP, and $P_i$ and in $pH_i$ and $[Ca^{2+}]_i$ can be measured at 0, 6, 12, 24, and 48 h in the treated glioma cells and compared with stage-matched, vehicle-treated controls. The effects produced by cariporide can be compared to those produced by glioma cells maintained in acidified medium at $pH_{ext}$ 6.6. Finally, the metabolic and ionic effects produced by cariporide and by SEA0400 can be compared to those produced by DCB, C2am-Gly, C5am-Gly, and peptide conjugates of C2am-Gly and C5am-Gly.

Depletions in cytosolic ATP can alter levels of inositol 1,4,5-triphosphoate ($IP_3$) that has been shown to enhance calcium release from the endoplasmic reticulum (ER) (Hofer et al., *J. Neurosci.*, 22:4850-4859 (2002)). Furthermore, impaired glycolysis can depress the ratio of NADH/NAD and lead to the generation of cyclic adenosine diphosphate ribose (cADPR) and nictotinic acid dinucleotide phosphate (NAADP). cADPR and NAADP have been shown to enhance the calcium release from different ER-associated pools. These metabolites cause the release of intracellular calcium from non-mitochondrial sites. Therefore, changes in the transmitochondrial membrane potential ($\Psi m$) can be measured in metabolically manipulated cells that demonstrate increased $[Ca^{2+}]_i$ levels. Quantitative fluorescent microscopy can measure changes in $\Psi_m$ in glioma cells with the dye rhod-2. Changes in $\Psi_m$ can be compared with $\Delta\Psi_m$ in glioma cells treated with oligomycin or FCCP.

ATP can be quantitated with either luciferase (e.g., determination of cytosolic free ATP) or HPLC (e.g., determination of both ATP and ADP pools that are closely associated with the mitochondria) (Manfredi et al., *Methods*, 26:317-326 (2002)).

Methods

Cell culture. The five human glioma cell lines can be obtained from the American Tissue Culture Collection (ATCC). Primary cultures of rat astrocytes can be isolated from the cerebral cortex of neonatal rats (0-1 day old). For measurements of $[H^+]_i$, $[Ca^{2+}]_i$, and $[Na^+]_i$, cells can be grown on glass coverslips coated with rat tail collagen type I.

MTT assay. MTT (3-(4,5-dimethylthiazol-2-yl)-2,5-diphenyltetrazolium bromide) is reduced from a tetrazolium salt to an insoluble purple formazon in viable cells that is detected spectrophotometrically (Mosmann, *J. Immunol. Methods*, 65:55-63 (1983)). Absorbances can be measured at 570 nm using a Power Wave microtiter plate reader and KC Junior 340 v1.11 software. Mean background absorbances of cell-free media (630 nm) can be subtracted from these values.

Manual cell counts with dye exclusion assays. Identical concentrations of glioma cells can be plated on 60 mm dishes and grown until 50% confluent. Following drug treatments, media containing floating cells can be collected in suspension. Adherent cells can be rinsed in calcium- and magnesium-free phosphate-buffered saline (PBS-CMF) and removed by incubation with 0.25% v/v trypsin for 5 minutes (37° C.). Cell suspensions can be combined with the floating fraction and centrifuged at 350×g for 5 minutes. The resulting pellet (one per dish) can be resuspended in equal volumes of PBS-CMF with 0.4% trypan blue and/or 500 nM Sytox Green. 10 μL aliquots of the suspension can be plated on a hemocytometer, and cells can be counted 5 minutes after staining. Simultaneous staining of cells with trypan (TB) and Sytox Green (SG) can be visualized by switching between visible light and fluorescein green.

Clonogenic assay. Cells can be trypsinized and about $10^3$ cells are plated on 100 mm dishes and incubated for up to 14 days. Control U87 glioma cells have a plating efficiency of about 35% to about 45%. The plates can be stained with crystal violet and colonies can be counted (Pollack et al., *Clin. Cancer Res.*, 7:1362-1369 (2001)).

Spectrofluorometric measurements of intracellular pH. $pH_i$ can be measured using the fluorescent ratio dye 2',7'-bis (carboxyethyl)-5,6-carboxyfluorescein acetoxy-methyl ester (BCECF-AM), as described in McLean et al., supra. Briefly, cells on coverslips can be loaded for 30 min with 0.5 to 1.5 μM of BCECF-AM in HEPES-buffered Ringer's (HR) at 37° C., 0% $CO_2$. Coverslips can be rinsed 3 times in HR, incubated in HR for 30 min at 37° C., 0% $CO_2$, and then transferred to cuvettes that permit continuous perfusion of solution. Calibration of BCECF can be performed using high $K^+$ solutions of known extracellular pH in conjunction with 10 μM nigericin. Complete calibration curves can be constructed over the pH range of 6.2 to 8.2, with the $F_{507}/F_{440}$ ratio normalized to the ratio measured at either pH 7.0 (astrocytes) or 7.4 (gliomas). A single calibration point can then be measured at the end of each experiment.

Spectrofluorometric measurements of intracellular calcium. $[Ca^{2+}]_i$ can be measured by loading cells on coverslips for 60 min with 0.5 to 2.0 μM of fura-2AM or fura-2FFAM in HEPES-buffered Ringer's (HR), 0% $CO_2$, as described in Vali et al., supra. Spectra can be excited at 340 and 380 nm with emission at 505 nm. Complete calibration curves can be constructed over the $[Ca^{2+}]_i$ range of between 1 μM to 100 μM using ionomycin with CaEDTA standards generated by the pH-metric method.

$IC_{50}$ drug determinations for NHE1. This method utilizes spectrofluorometric measurements of $[H^+]_i$ as described above. The ammonium chloride prepulse method can be used to acidify cells in the presence of HR that is sodium-substituted with NMDG. Perfusion of the acidified cells with HR that contains sodium causes activation of NHE1 that is inhibited in a concentration-dependent fashion as described in McLean et al., supra.

High Throughput screening of $IC_{50}$ for NHE1 using glioma cells transfected with a pH-sensitive GFP expression protein. U87 glioma cells can be stably transfected with a construct containing the pH-sensitive, mutant green-fluorescence protein (GFP), pHluorin (Miesenbock et al., *Nature*, 394:192-195 (1998)). This mutant GFP protein is ratiometric with a pH-sensitive emission of 475 nm and an isobestic emission at 395 nm. The $IC_{50}$ of NHE1 inhibitors can be measured using this stably transfected cell line.

$IC_{50}$ drug determinations for NCX. This method utilizes spectrofluorometric measurements of $[Ca^{2+}]_i$ as described above. Treatment of the cells with FCCP (10 μM) elevates $[Ca^{2+}]_i$ levels in the presence of HR that is sodium-substituted with NMDG. Perfusion of the cells with HR that contains sodium causes activation of the forward mode of NCX that is inhibited in a concentration-dependent fashion with NCX inhibitors (Kopper et al., id).

Quantitative fluorescent microscopy of $pH_i$. $pH_i$ can be measured in human U87 glioma cells grown on coverslips at approximately 50% cell densities. Cells can be loaded with BCECF-AM as described above. Excitation light can be delivered by fiber optics to cells through the epifluorescence port of a Nikon E600 microscope coupled to a Nikon Fluor 40× or 60× water immersion lens. The detector can be an Orca II-ER CCD digital camera which is computer controlled by C-Imaging Simple PCI software. Bath temperature and solutions can be regulated by a PDMI-2 open perfusion chamber.

Quantitative fluorescent microscopy of $[Ca^{2+}]_i$ levels. $[Ca^{2+}]_i$ levels can be measured in cells loaded with either fura-2A or fura-2FFAM under the conditions described above.

Measurements of ATP, ADP, and AMP. Levels of ATP, ADP, AMP, and phosphocreatine can be quantitated in skeletal muscle extracts by using an HPLC system as described in Wineinger et al., *Amer. J. Physiol.*, 261:C169-176 (1991). Briefly, cultured cells are washed 3 times with 0.9% saline at 4° C., and then concentrated by centrifugation (200×g) at 4° C. for 5 min. The cell pellet is lysed by rapid freezing in liquid nitrogen and then dissolved into the mobile phase used for fractionation by HPLC. The adenine nucleotides are separated on a 4.6 mm×150 mm reverse-phase C18 ODS column (Dychrom) under isocratic conditions (3.5% acetonitrile, 2.3 mM tetrabutylammonium hydrogen sulfate, 215 mM dipotassium hydrogen phosphate) at a flow of 1-1.3 ml/min. Standard curves for purified samples of ATP, ADP, and AMP (Sigma) are made just prior to analysis of the extracts.

Example 10

Evaluation of Amiloride Amino Acid and Peptide Conjugates in Glioma Cell Lines and Astrocytes This example illustrates: (1) a comparison of the cytotoxic and the antiproliferative efficacies of C2am-Gly and C5am-Gly in a set of five human glioma cell lines and in primary astrocytes; (2) a correlation of the effects of the amiloride amino acid conjugates on glioma cells with their inhibition of the sodium-calcium exchanger (NCX) and of the sodium proton exchanger (NHE1); (3) a utilization of the structure-activity information to design and synthesize amiloride peptide conjugates; and (4) an evaluation of the biological activities of these amiloride peptide compounds in a set of glioma cell lines and in primary astrocytes. Compounds that are efficacious and selective for gliomas can be further evaluated using intracerebral glioma xenograft models.

In particular, the amiloride amino acid and peptide conjugates of the present invention can be analyzed as follows:
1. Evaluation of both protected (e.g., t-butyl oxycarbonyl) and deprotected amiloride conjugates by screening in primary astrocytes and in a set of five glioma cells lines listed in Table 7.
2. Log dose screening of the compounds using the MTT assay to measure the number of live glioma cells and primary astrocytes in 96 well microtiter plates at 24, 48, and 72 h.
3. Manual cell counts coupled with the trypan blue exclusion assay using the most potent and selective compounds to assess cytotoxic and anti-proliferative effects in glioma cells and primary astrocytes.
4. Determination of the $IC_{50}$ of NHE1 in U87 gliomas for the most potent and selective compounds.
5. Determination of the $IC_{50}$ of NCX in U87 gliomas for the most potent and selective compounds.

TABLE 7

Several properties of the human glioma cell lines selected for in vitro screening.

| Glioma Cell Type | U87 | T98G | A172 | U118 | U373 |
|---|---|---|---|---|---|
| p53 | wt | mt | mt | wt | mt |
| pRb | wt | wt | wt | | wt |
| p16ink | mt | mt | mt | | mt |

TABLE 7-continued

Several properties of the human glioma cell lines selected for in vitro screening.

| Glioma Cell Type | U87 | T98G | A172 | U118 | U373 |
|---|---|---|---|---|---|
| p27kip1 | low | normal | low | | |
| PTEN | mt | mt | mt | | |
| tumor formation in athymic mice | yes | no* | no | yes | yes |
| Contact inhibition | no | yes | no | no | no |
| MMP-2 expression | high | high | low | high | |
| EGF Receptor overexpression | yes | no | | no | no |
| G1 arrest with staurosporine | yes | yes | yes | | |
| Low dose hyper radiosensitivity | yes | yes | no | no | no |
| Temozolamide sensitivity | yes | no | | | yes |

*T98G has been used for intracerebral xenografts in nude mice with Matrigel (Rubenstein et al., Methods Find Exp. Clin. Pharmacol., 21: 391–393 (1999)).

Experiment #1: Determine whether C5am peptide conjugates primarily inhibit NHE 1 and exhibit a predominantly antiproliferative effect on glioma cells. Further, determine whether these C5am peptide conjugates reduce intracellular edema by their reduction of $[Na^+]_i$.

C5am peptide conjugates can be prepared using the solution-phase synthesis strategy according to Scheme 1 from Example 4 and the solid-phase synthesis strategy according to Scheme 4, below. As shown in Scheme 4, compound 3a (see, Scheme 1) can be used as the starting material to synthesize additional peptide conjugates (compound 7) as well as their benzyl (compound 8A) and carboxylate derivatives (compound 8B). In particular, the solid-phase synthesis strategy can proceed as follows: compound 3a can be loaded onto the resin by reaction with activated carbonate Wang resin and diisopropylethylamine, according to a procedure developed for the loading of structurally analogous guanidine-containing substrates (Ghosh et al., *J. Org. Chem.*, 66:2161-2164 (2001)). The site of attachment can be regioselective since the guanidine moiety preferentially reacts with acyl electrophiles in the presence of C(3)- and C(5)-amino moieties (e.g., compound 5, Scheme 2). Thus, resin-bound substrate 6 (Scheme 4) can be transformed into a variety of amino acid conjugates by elaboration of the carboxylic acid terminus using standard N- to C-directed (inverse) solid phase peptide conditions (Fmoc-amino acid esters, DIC, HOBT) (Henkel et al., *Liebigs. Ann. Recueil.*, 2161-2168 (1997); Johanson et al., *J. Comb. Chem.*, 2:496-507 (2000)). Fmoc deprotection can be effected using 50% piperidine in DMF. The terminal amino acids of peptide compound 7 can be attached as benzyl (Bn) ester derivatives. Cleavage of the peptide conjugates from the resin can be accomplished by exposure to trifluoroacetic acid (TFA) (Sieber, *Tetrahedron Lett.*, 28:6147-6150 (1987)) to produce the benzyl-terminated conjugates (8A). The corresponding free carboxylic acid derivative (8B) can be prepared by exposure of compound 7 to $H_2$ and $Pd(OAc)_2$ in DMF. Such hydrogenolysis conditions can cleave the benzyl ester as well as liberate the peptide conjugates from the resin (Hauske et al., *Tetrahedron Lett.*, 36:1589-1592 (1995)). The structure and purity of all conjugates can be established by LC-MS in conjunction with $^1H$ and $^{13}C$ NMR spectroscopy. Such solid-phase synthesis strategies allow the preparation and evaluation of multiple peptide sequences via traditional combinatorial methods (Sewald et al., *Peptides: Chemistry and Biology*, Wiley-VCH, Weinheim (2002)).

Scheme 4

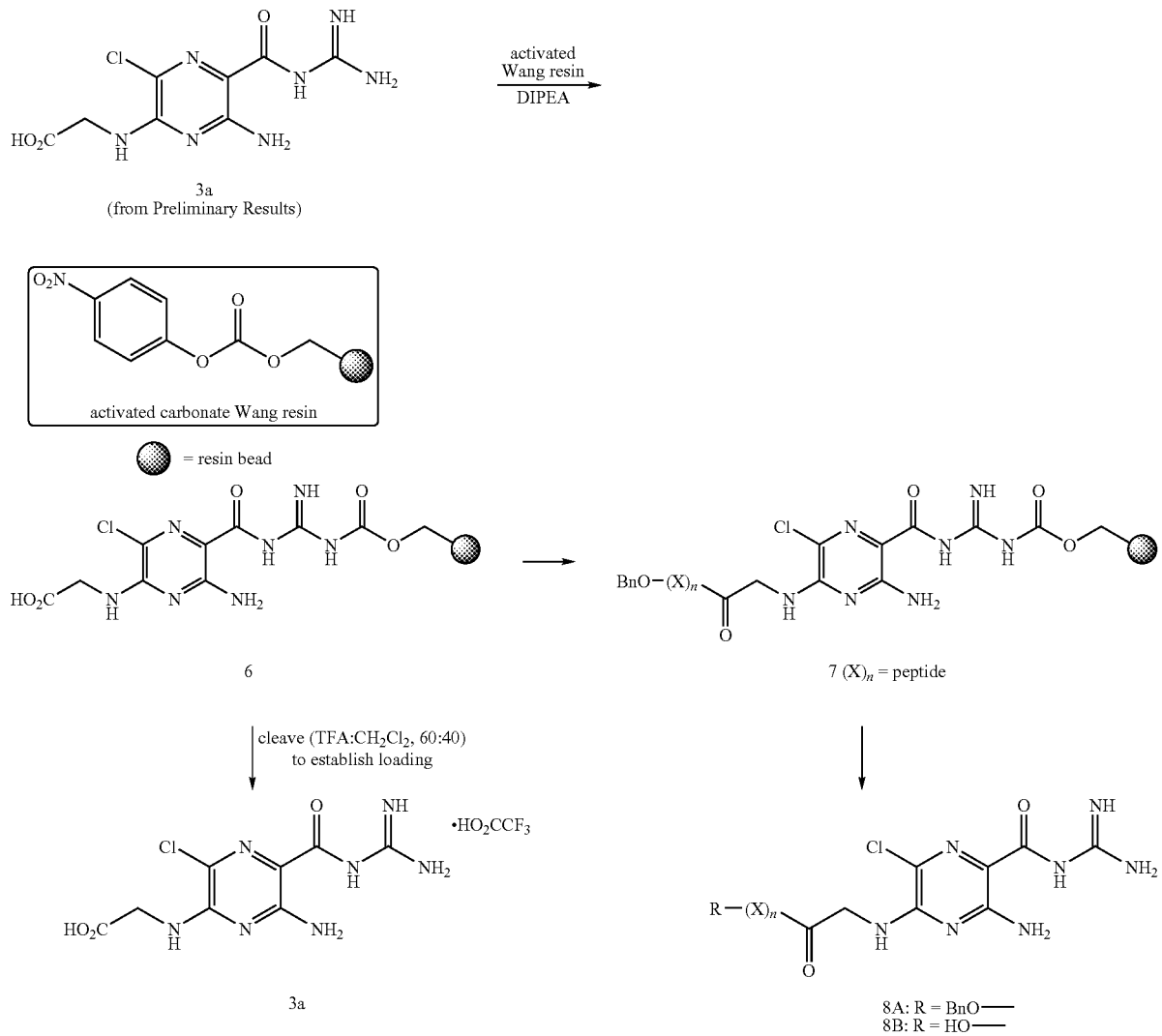

The effect of increasing peptide chain length on glioma cell proliferation and cytotoxicity as compared to primary astrocytes can also be examined. This biological activity can then be compared to their ability to inhibit NHE1 and/or NCX in U87 gliomas. The peptide sequences (depicted N'→C') examined can be: (1) Gly-Gly-am; (2) Gly-Gly-Gly-am; (3) Gly-Gly-Gly-Gly-am (SEQ ID NO:43); (4) Gly-Gly-Gly-Gly-Gly-am (SEQ ID NO:44); etc., wherein "Gly-am" represents the amiloride-glycine conjugate core structure. Such C5am-(Gly)$_n$ conjugates can be evaluated in cell lines and in assays measuring NHE1 and NCX inhibition. Analyses of these peptide conjugates using LC-MS can determine whether these glycine derivatives are stable in culture medium.

A second set of C5am peptide conjugates is modeled on the enkephalin peptide analog, Tyr-D-Ala-Gly-Phe-NH$_2$ (SEQ ID NO:45), which has been shown to enter the brain from the vascular compartment by utilizing several transport mechanisms (Hau et al., J. Pharm. Sci., 91:2140-2149 (2002)). The initial peptide sequences derived from the enkephalin peptide analog can be as follows: (1) Tyr-Gly-am; (2) Tyr-Gly-Gly-am; (3) Tyr-D-Ala-Gly-am; (4) Tyr-Gly-Gly-Gly-am (SEQ ID NO:46); (5) Tyr-Gly-Gly-D-Ala-Gly-am (SEQ ID NO:47); and (6) Tyr-D-Ala-Gly-Phe-Gly-am (SEQ ID NO:48), wherein "Gly-am" represents the amiloride-glycine conjugate core structure. This set of conjugates can be designed to be cleaved or be resistant to brain peptidases by the introduction of D-amino acids. As such, neutral endopeptidase 24.11 in brain would cleave the peptide moieties in the absence of D-amino acids and generate the C5am Gly.

A third set of C5am peptide conjugates can be designed to provide a substrate for matrix metalloproteinase-2 (MMP-2). An analysis of peptide sequences that can be selectively cleaved by MMP-2 or MMP-9 has been described in Chen et al., J. Biol. Chem., 277:4485-4491 (2002). Although not all malignant glioma cells express MMP-2 or MMP-9, at least 3 of the 5 human glioma cell lines in Table 7 have been documented to overexpress MMP-2. As such, C5am conjugates containing an MMP-2 peptide substrate can be incubated with recombinant MMP-2 enzyme (Oncogene #PF023), followed by homogenates prepared from U87 glioma cell lines. For these studies, the following peptides can be conjugated to the glycine at the C(5) position based upon sequences known to be recognized by MMP-2 as compared to other MMP family members, and with other known brain endopeptidases (Chen et al., supra): (1) Glu-Ser-Leu-Ala-Tyr-Tyr-Thr-Ala-Gly-am (SEQ ID NO:49); (2) Arg-Ser-Leu-Ser-Arg-Leu-Thr-Ala-Gly-am (SEQ ID NO:50); (3) Glu-Ser-Leu-D-Ala-Tyr-Tyr-Thr-Ala-Gly am (SEQ ID NO:51); (4) Arg-Ser-Leu-Ser-Arg-D-Leu-Thr-Ala-Gly-am (SEQ ID NO:52); and (5) Arg-Ser-Leu-Ser-Arg-Leu-Thr-Ala-Gly-Gly-am (SEQ ID NO:53). Comparable MMP-2 peptide substrates can be designed for conjugation to C2am Gly.

according to the protocol for the preparation of compound 5 (see, Scheme 2). The peptide side chains can then be elaborated using the well-established Fmoc protocol for solid-phase peptide synthesis. After Fmoc deprotection, treatment of the resin-bound conjugates at this stage with trifluoroacetic acid can deliver conjugate 13B. The corresponding N-benzyl series (13A) requires that the terminal amino acid of the peptide side chain be added as its N-benzyl derivative rather than the N-Fmoc counterpart. In this event, the subsequent TFA-mediated resin cleavage reaction delivers conjugate 13A.

Scheme 5

Experiment #2: Determine whether C2am amino acid and peptide conjugates inhibit NCX more than NHE1 and whether they are more cytotoxic to glioma cells.

C2am peptide conjugates (i.e., guanidino-linked) can be prepared using the solid-phase synthesis strategy outlined below in Scheme 5. In particular, the 5-chloro atom of commercially available ester 9 (Aldrich Chemical Company; Milwaukee, Wis.) can be readily displaced under basic conditions by reaction with amines. Thus, compound 9 can be treated with a PMB-activated amino-resin (e.g., amino-(4-methoxyphenyl)methyl polystyrene, Novabiochem) to obtain resin-loaded pyrazine-ester 10. Subsequent reaction with guanidine can transform the methyl ester into the corresponding guanidine 11. Alternatively, dichloro compound 2 (see, Scheme 1) can be reacted with aminomethylated resin to directly produce 11. Guanidine acylation can be performed First, the impact of peptide chain length of conjugates with the structure of 13A and their corresponding amino derivatives (13B) on glioma cytotoxicity and proliferation can be systematically examined. These biological activities can be compared with their corresponding inhibition of NHE1 and/or NCX in U87 gliomas. The peptide sequences examined can be: (1) am-Gly; (2) am-Gly-Gly; (3) am-Gly-Gly-Gly; (4) am-Gly-Gly-Gly-Gly (SEQ ID NO:54); (5) am-Gly-Gly-Gly-Gly-Gly (SEQ ID NO:55); (6) am-Gly-D-Ala-Gly; (7) am-Gly-D-Ala-Gly-D-Ala-Gly (SEQ ID NO:56); etc., wherein "am-Gly" represents the amiloride-glycine conjugate core structure. Analyses of these C5am peptide conjugates using LC-MS can determine whether these compounds are stable in culture medium or require the addition of protease inhibitors to the culture medium.

Figure 10:
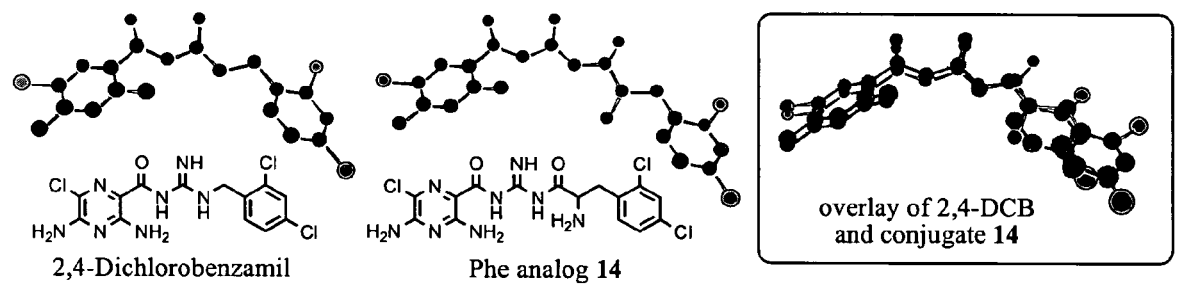
FIG. 10 shows an overlay of MM2-minimized structures with hydrogens omitted for clarity (obtained from Chem3D).

Second, C2am-phenylalanine (C2am-Phe) and C2am-serine (C2am-Ser) conjugates, as well as C2am peptide conjugates containing Phe and Ser analogs such as 2,4-dichloro-Phe and O-benzyl serine can be synthesized and examined for their effects on glioma cytotoxicity and proliferation. These conjugates are similar in structure to the hydrophobic DCB, but represent more polar amiloride derivatives that can position their peptide side chains to overlap with the C(2) dichlorobenzyl group of DCB. In particular, molecular modeling of C2am-(2,4-dichloro)-Phe (compound 14) illustrates how the C(2) peptide side chain may be used to position functionality while maintaining a close structural similarity to DCB (see, FIG. 10). Similarly, the serine hydroxyl group affords the opportunity to position benzyl and 2,4-dichlorobenzyl groups in a manner that closely mimics the potent amiloride analogs benzamil and DCB. This effect can be examined by preparing the following conjugates: (1) am-X-NHBn; (2) am-X-NH$_2$; (3) am-Gly-X-Gly-Phe-NHBn; and (4) am-Gly-X-Gly-Phe-NH$_2$, wherein X represents (2,4-dichloro)-Phe or O-benzyl serine. As such, the potent cytotoxic effects of DCB can be preserved, while the general toxicity and lethality associated with the rapid entry of DCB into cells can be reduced.

Experiment #3: Determine the biological activities of C2,C5am-Gly$_2$ on glioma cell proliferation and cell death and correlate these activities with its inhibitory effects on NCX and NHE1.

Synthesis of C2,C5am-Gly$_2$: Using the procedure for the synthesis of conjugates 3a-c (Scheme 1), a tert-butyl-protected Gly analog (15) can be prepared from commercially available O-t-Bu-glycine as shown in Scheme 6, below. Subsequent attachment of N-Boc-glycine to the guanidine moiety can be performed as described above. Acid-mediated deprotection of the O- and N-protection groups can be effected using HCl in acetic acid to produce compound 17.

Scheme 6

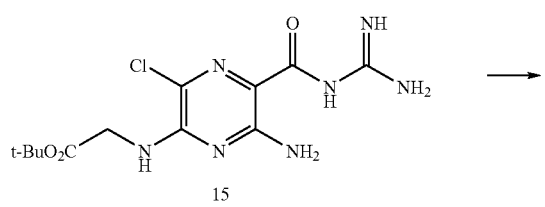

15

-continued

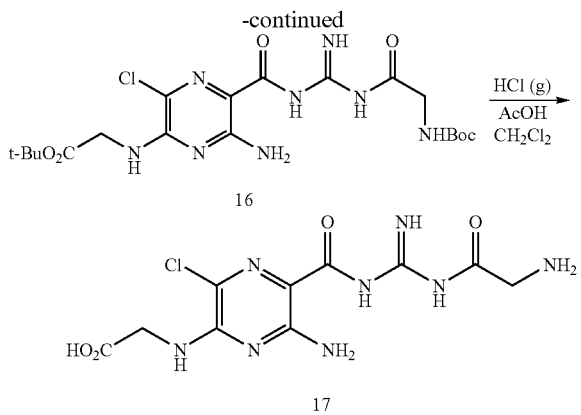

Figure 11:
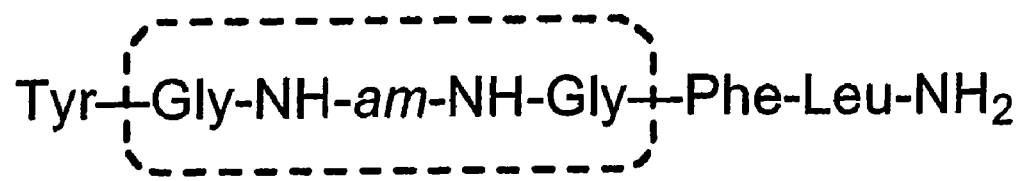
FIG. 11 shows a [Leu]$^5$-enkephalin amide analog that incorporates C2,5am-(Gly)$_2$ into the third residue.

C2,C5am-Gly$_2$ can be used as a "pseudo-peptide residue" that is likely non-hydrolyzable by peptidases and which can be internally incorporated into peptides known to cross the blood brain barrier (see, FIG. 11). The following analogs of [Leu]$^5$-enkephalin amide can be generated that incorporated C2,C5am-Gly$_2$: (1) Tyr-Gly-am-Gly-Phe-Leu-NH$_2$; (2) Tyr-Gly-Gly-am-Gly-Gly-Phe-Leu-NH$_2$ (SEQ ID NO:8); and (3) Tyr-D-Ala-Gly-am-Gly-Phe-D-Leu-NH$_2$, wherein "Gly-am-Gly" represents the C2,C5am-Gly$_2$ core structure. These conjugates can be tested with purified enkephalinase as previously described and fresh brain homogenates to analyze peptide fragmentation by LC-MS.

Experiment #4: Determine the biological activities of C2am-Gly-(Peptide)-C5am-Gly (i.e., $C_2$-$C_5$ dimer) on glioma cell proliferation and cell death and correlate these activities with its inhibitory effects on NCX and NHE1.

Synthesis of C2am-Gly-(Peptide)-C5am-Gly: The resin-bound peptide conjugate 7b (prepared according to Scheme 4) can be coupled to the C2am-Gly analog 18 as shown in Scheme 7, below. Palladium-mediated hydrogenolysis can then be employed to deprotect the C(5)-amino group of compound 18 to obtain compound 19b. These conditions may affect cleavage of the substrate from the resin to furnish dimer 20, and the order in which these hydrogenolyses occur would have no consequence on the formation of the desired target 20. In the event 20 is not liberated from the polymer support, 19a can be subjected to TFA-mediated cleavage conditions to obtain dimer 20.

Scheme 7

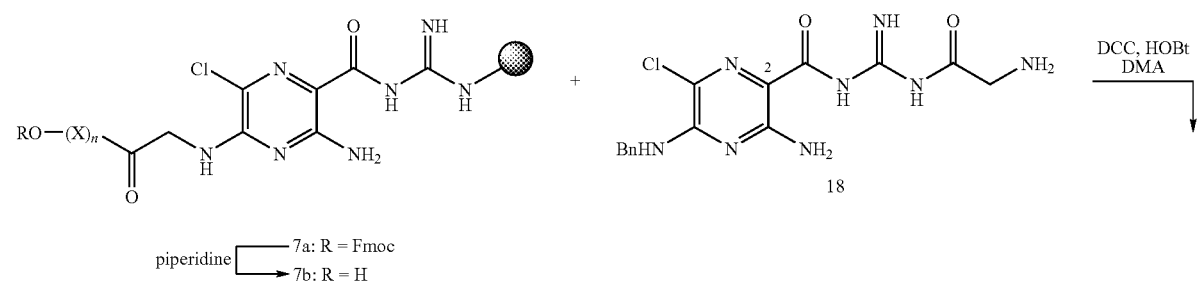

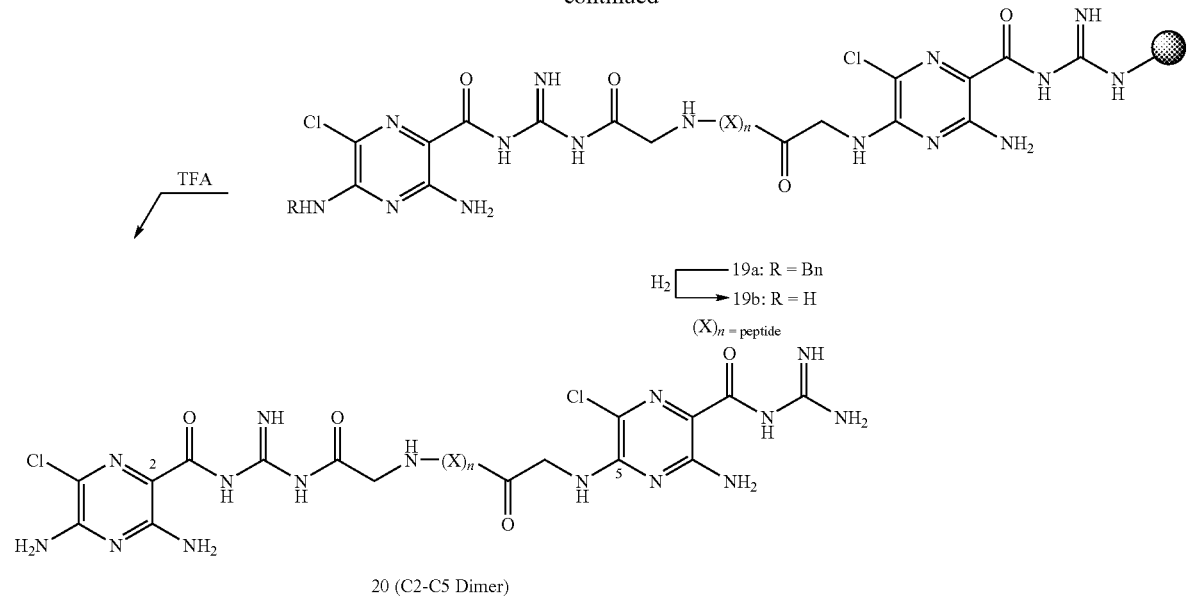

20 (C2-C5 Dimer)

The dimeric C2am-Gly-(Peptide)-C5am-Gly conjugate can be designed to be bifunctional, capable of generating both C5am-Gly and C2am-Gly upon cleavage of the internal peptide linker by a peptidase. The hydrophobic nature of the intact, di-amide peptide conjugate facilitates its transport across the BBB, wherein the more hydrophilic C5am-Gly and C2am-Gly conjugates are released following selective cleavage of the peptide linker by a brain- or tumor-specific peptidase, such as enkephalinase or MMP-2. As a result, these dimeric conjugates provide increased specificity and accessibility, with decreased toxicity to non-targeted (e.g., non-tumor) cells.

Methods

Liquid chromatography/mass spectrometry (LC-MS). The mass spectral analysis can be performed using a Thermo Finnigan LCQ fitted to an Electrospray (ESI) source and Ion Trap mass analyzer with an ABI 120A HPLC. A C18 column (Vydac, 300 A, 250×1 mM) can be used for all analyses. Samples can be injected and a gradient HPLC run can be performed from 5% to 90% acetonitrile over 1 h with 0.1% aqueous formic acid as the secondary solvent. Samples can be sprayed at the flow rate of 100 µl/min.

Enzymatic digestions of C(2)-amiloride and C(5)-amiloride peptide conjugates. Commercially purified enkephalinase (neutral endopeptidase 24.1.1) can be obtained from Calbiochem and recombinant matrix metalloproteinase-2 (MMP-2) and MMP-9 can be obtained from Oncogene. Chymotrypsin, which recognizes peptide sequences containing basic amino acid side chains, can be used as a negative control. The enzymatic digests containing the peptides can be incubated in buffers and at conditions recommended by the manufacturers for 6-12 h. LC-MS can be used to identify the principal mass peaks of the peptides in samples taken from the enzymatic hydrolysates and from buffers without the addition of enzymes.

Additional methods are described in Example 9 above.

Example 11

Evaluation of the C2am and C5am Amino Acid and Peptide Conjugates in Intracerebral Glioma Xenografts This example illustrates further evaluation of the amiloride conjugates of the present invention using an intracerebral glioma xenograft model.

Experiment #1: Determine which amiloride conjugates of the present invention kills or impedes the proliferation of a population of glioma cells surviving in a hypoxic-ischemic tumor microenvironment.

Rationale: Glioma cells in hypoxic-ischemic tumor environments lack extracellular $CO_2/HCO_3^-$ and must rely entirely upon increased activity of NHE1 to maintain an alkalotic $pH_i$ (McLean et al., supra). Perinecrotic glioma cells in C6 and U87 xenografts survive and undergo cell cycle arrest while scattered glioma cells within poorly vascularized tumor regions continue to incorporate BrdU (Gorin et al., *Acta Neuropathol.* 107:235-244 (2004)). Glioma cells in this environment are frequently resistant to radiation therapy and conventional chemotherapy. However, their altered intracellular ionic composition may result in their susceptibility to inhibitors of NCX and NHE1, e.g., compounds of the present invention.

Experimental Design: For these studies, NMR can be used to serially monitor the U87 tumor growth rate of intracerebral U87 glioma xenografts treated intracerebrally with the amiloride conjugates of the present invention. Log dose screening of compounds using a set of five glioma cells lines (see, Table 7) and primary astrocytes can be employed to identify those amiloride amino acid and peptide conjugates that are efficacious in selectively killing and/or inhibiting glioma proliferation. Following the establishment of concentration ranges, manual cell counts can assess drug-induced alterations in cell proliferation and viability.

The in vivo toxicity studies can employ single, daily intracerebral infusions of the candidate compound into Sprague-Dawley rats for 12 days. The infused drug concentration can be based upon the cell line studies and adjusted for the low protein content of the cerebrospinal fluid, which is 0.2% that of serum. Animals can be behaviorally assessed for toxicity. In terminal experiments, brains can be removed at days 4, 6, 8, 10, and 12 and frozen to determine drug levels by LC-MS as performed with amiloride. The behavioral assessment can be conducted as performed with amiloride.

U87 glioma cells can be stereotaxically implanted into the corpus striatum of athymic rats. Tumors can be permitted to grow to 40 mm$^3$ volume based upon established growth rates and verified by NMR. Alzet pumps modified to accommodate NMR imaging and deliver a range of 1-350 pmol/24 h of amiloride amino acid or peptide conjugates for up to 14 days can then be connected. Tumor growth rates for U87 gliomas can be determined with $^1$H-NMR by serially measuring volumes over a 10-day period (4 doubling times of U87 tumor). Following spectroscopic measurements of tumor volumes, animals can be injected i.p. with BrdU 3 h prior to deep anesthesia when they can be infused with paraformaldehyde by cardiac perfusion for histological studies. Those compounds showing significant regression of tumor size and/or inhibition of tumor growth rate can be further evaluated using human U118 and U373 intracerebral xenografts in athymic rats. Tumor volumes can be serially determined prior to and following drug administration using NMR. Brain drug levels can be measured using NMR.

The following table (Table 8) summarizes the number of rats estimated to assess in vivo drug efficacies and neurotoxicological studies for the conjugates of the present invention.

Following completion of the cytological studies that assess the efficacy of the amiloride conjugates of the present invention, a survival study can be performed in a human U87 glioma xenograft model. The protocol follows that of drug suppression of an established xenograft tumor. The efficacy of drug treatment is assessed by the survival rate of animals at each day post-implantation. Based upon published survival studies of the U87 glioma xenograft model (Nagane et al., *Cancer Res.*, 60:847-853 (2000)), about 10 nude rats per treatment group can be compared against sham- and vehicle-treated animals (see, Table 9).

TABLE 9

Survivability studies of established tumors in a human glioma xenograft model. The percent of surviving animals in the treatment groups (n = 10 per group) is compared with sham- and vehicle-treatment groups.

| Glioma Model | Sham-treated suppression of established tumor | Vehicle-treated suppression of established tumor | C5am-Gly optimized dose | C2am-Gly optimized dose | C2am-peptide optimized dose |
|---|---|---|---|---|---|
| U87 | 10 | 10 | 10 | 10 | 10 |
| TOTALS | — | — | — | — | 50 |

High dose amiloride infusion for 12 days with the Alzet pump can demonstrate that levels in the brain peak at day 8 and are decreasing by day 12 (see, Example 2). The accumulation in the brain indicates the possibility that pulsed administration of amiloride or its amino acid or peptide conjugates

TABLE 8

Estimate of the number of Sprague Dawley and athymic rats for drug efficacy and neurotoxicity studies.

| animal models | C(2) amiloride conjugates | C(5) amiloride conjugates | bis (glycine) amiloride deriv | C(2), C(5) amiloride conjugates |
|---|---|---|---|---|
| Sprague-Dawley controls for neurotoxicity studies (total 192) | n~5 cmpds 6 per cmpd total: 30 | n~5 cmpds 6 per cmpd total: 30 | n~3 cmpds 6 per cmpd total: 18 | n~3 cmpds 6 per cmpd total: 18 |
| Intracerebral U87 xenografts 1. Spectroscopy-> Histology studies with fixed brain | n~4 cmpds 6 per cmpd total: 24 | n~4cmpds 6 per cmpd total 24 | n~2cmpds 6 per cmpd total 12 | n~2cmpds 6 per cmpd total 12 |
| 2. Spectroscopy->mapping of hypoxic and acidic regions, measurements of drug levels with frozen brain (total = 240) | 3 per cmpd total 12 | 3 per cmpd total 12 | 3 per cmpd total 6 | 3 per cmpd total 6 |
| Intracerebral U118 xenografts 1. Spectroscopy-> Histology studies with fixed brain | n~2cmpds 6 per cmpd total: 12 | n~2cmpds 6 per cmpd total: 12 | n~1cmpds 6 per cmpd total: 6 | n~1cmPds 6 per cmpd total: 6 |
| 2. Spectroscopy->mapping of hypoxic and acidic regions, measurements of drug levels with frozen brain (total = 54) | 3 per cmpd total 6 | 3 per cmpd total 6 | 3 per cmpd total 3 | 3 per cmpd total 3 |
| Intracerebral U373 xenografts 1. Spectroscopy-> Histology studies with fixed brain | n~2cmpds 6 per cmpd total: 12 | n~2cmpds 6 per cmpd total: 12 | n~1cmpds 6 per cmpd total: 6 | n~1cmpds 6 per cmpd total: 6 |
| 2. Spectroscopy->mapping of hypoxic and acidic regions, measurements of drug levels with frozen brain (total = 54) | 3 per cmpd total 6 | 3 per cmpd total 6 | 3 per cmpd total 3 | 3 per cmpd total 3 |
| Total Sprague Dawley rats over 5 years: 192 | | | | |
| Total Athymic Nude rats over 5 years: 348 | | | | | cmpds = estimated number of amiloride-based derivatives to be tested based upon screening.

could be more efficacious and have less-side effects. LC-MS can be used to measure the levels of the amiloride amino acid and peptide conjugates in the brain. The most therapeutically promising compounds could also be radiolabeled to assess their intracerebral stability and kinetics.

Experiment #2: Measure the number of glioma cells undergoing cell death, DNA damage, and DNA synthesis with amiloride amino acid and peptide conjugates of the present invention using histological and stereological methods.

Rationale: Necrotic glioma death produced by amiloride and DCB in U87 intracerebral xenografts has been detected with eosin and Hoescht 3222, a fluorescent nuclear stain. GLUT-1 immunostaining has been found to occur in U87 and C6 glioma cells bordering regions of necrosis that are stained by eosin. H2Ax immunostaining is more sensitive than TUNEL staining and is suitable for detecting damaged double-stranded DNA in apoptotic cells. Similar staining techniques can be used for the detection of necrotic cells in tumor xenografts infused with amiloride amino acid and peptide conjugates of the present invention.

Experimental Design: Animals with tumor xenografts receiving an infusion of amiloride amino acid and peptide conjugates can be injected with BrdU prior to perfusion fixation with 4% paraformaldehyde (PFO) in terminal experiments. Brains can be post-fixed, dehydrated, embedded in paraffin, and sectioned coronally at 40 µm for stereology and at 4 µm for immunohistology. Stereological methods using optical sectioning of the 4 µm sections can be used to (1) identify and quantitate areas of tumor that have undergone cell death and (2) calculate indices of BrdU-positive glioma cells. These results can be compared to those obtained from tumor xenografts treated with vehicle.

Experiment #3: Determine correlation between tumor regions of glioma cell death and DNA damage with regions of persistent tumor acidosis and hypoxia.

Rationale: Persistent regional acidosis in glioma xenografts at the cytological level is below the spatial resolution of pH microelectrodes. Perfusing rats with neutral red dye is routinely used to semi-quantitatively measure acidotic brain regions following global ischemia (Hoxworth et al., Brain Res., 821:467-479 (1999)) and to evaluate the role of NHE1 in the rat hippocampal slices (Lin et al., Brain Res., 731:108-113 (1996)).

Experimental Design: Neutral red can be perfused in animals pretreated 3 h before with BrdU and then brains can be immediately frozen using the liquid nitrogen funnel technique. Cryostat frozen sections can then be visualized and photographed by CCD camera for subsequent analyses using NIH Image (Hoffman et al., J. Neurosurg., 81:567-573 (1994)). Adjacent facing 4 µm sections can be used to identify BrdU labeling and GLUT-1 expression. GLUT-1 expression is increased in glioma cells under conditions of either hypoxia or acidosis in C6 and U87 intracerebral xenografts.

Experiment #4: Determine correlation between tumor regions of glioma cell death and DNA damage with regions of persistent tumor acidosis and hypoxia.

Rationale: Persistent regional hypoxia in glioma xenografts at the cytological level cannot be measured reliably using oxygen microelectrodes or by immunostaining for increased hypoxic inducible factor (Hif-1) or its gene products (Koch, Methods Enzymol., 352:3-31 (2002)). HIF regulation is complex and very short lived (Agani et al., Amer. J. Physiol. Cell Physiol., 283:C178-186 (2002)), but PTEN mutations, pyruvate/lactate, IGF-1, and nitric oxide have been reported to potentiate Hif expression (Zundel et al., Genes Dev., 14:391-396 (2000)). EF5 can be perfused into tissues, including brain, and forms adducts under hypoxic conditions that are visualized in frozen sections using a commercial monoclonal antibody against EF5. EF5 staining in human tumors is consistent with diffusion-limited hypoxia rather than acute hypoxia measured by HIF-1 (Evans et al., Amer. J. Clin. Oncol., 24:467-472 (2001)).

Experimental Design: EF5 can be perfused transcardially in animals pretreated 3 h before with BrdU and then brains can be immediately frozen. Frozen sections can be immunostained with a monoclonal antibody against EF5 adducts. The maximal binding rate of oxygen to EF5 can be estimated by assuming an "average" oxygen dependence of binding for the contralateral normal cerebral hemisphere in conjunction with the tissue cube method (Koch, supra). The best-fit approximation for existing data is an inverse relationship between binding and $pO_2$, with binding decreasing 50-fold between 0.1% and 10% oxygen.

Experiment #5: Evaluate the neurotoxicities of the amiloride conjugates of the present invention using behaviorial assessments and neuropathological surveys.

General Health and Behavioral Studies. Body weights and behavioral parameters can be assessed daily in drug-treated and vehicle-treated rats for 14 days. Standardized behavior tests, which include quantitative measures of vestibulomotor function, fine motor coordination, ambulation, and spatial memory can be used. A daily neurotoxicity behavioral sign checklist can also be performed to detect neurological signs of toxicity and seizures. Acquisition of spatial memory is particularly sensitive for detecting subtle drug toxicities. Body weight can be used as a measure of general health.

Neuropathological Studies. Cytological studies can be performed in the same drug-treated and vehicle-treated rats at the conclusion of behavioral testing. Fixation and sectioning techniques are described in the Methods below. Hematoxylin and eosin can be used routinely to survey for neuropathological changes. Luxol fast blue stains myelin tracts to evaluate potential white matter changes. The surveyed brain regions can be influenced by symptomatology (e.g., ataxia, spasticity), but can include parasaggital and coronal tissue blocks of the nucleus caudatus, putamen, dentate gyrus, cerebellum, primary somatosensory cortex, cingulate gyrus, and brainstem regions that include the inferior olives, and the vestibular nuclear complex. Assessment of brainstem white matter tracts with luxol fast blue staining can include the spinocerebellar, vestibulospinal, corticospinal, and spinothalamic tracts. Specialized stains for reactive astrocytes, neuronal chromatolysis, etc. can be added if brain lesions are detected. These stains can include Fluoro-Jade to detect neuronal degeneration (Schmued et al., Brain Res., 751:37-46 (1997)) and GFAP immunostaining for glial fibrillary acidic protein as a sensitive detection for reactive glial responses. Analysis of the neuropathology slides can be performed in double-blind experiments.

Experiment #6: Amiloride conjugates of the present invention that are efficacious in the xenograft models can be injected into the tail veins of control rats. Blood and brain levels can be measured using LC-MS and can be subsequently radiolabeled, as needed, for more precise quantitation. A particular level of sensitivity (i.e., detection of 0.01 pmol of amiloride per gram of brain tissue) can be adequate to measure levels of amiloride conjugates that accumulate in the brain and cerebrospinal fluid during intracerebral administration. This information is useful for subsequent studies examining neurotoxicity and for evaluation of whether the conjugates effectively partition across the blood brain barrier following administration into the internal jugular vein. If an effective conjugate is identified, radiolabeling can be performed to accurately assess the transport of the conjugate from blood to the brain as well as its stability within the brain.

Methods

Statistical Analyses. Sample sizes for the experiments can be determined by power analysis using an acceptable level of statistical power (80) to reliably detect treatment effects. Alpha level for Type I error can be set at 0.05 for rejecting null hypotheses. Suppression of tumor volume by NHE1 inhibitors, stereological counts of cytological markers, and dose-response effects of individual drugs can be analyzed with one-way (Treatment Group) ANOVA followed by post hoc Dunnett's test for comparison of individual treatments to control. Differences in survival duration between controls and drug-treated groups for in vivo experiments can be compared using the Cox-Mantel analysis.

Intracerebral Glioma Xenograft Model. Rats (250-280 gm) can be intubated with 4% isoflurane and air:$O_2$ (2:1), maintained on 2% isoflurane, and placed into a Kopf stereotactic apparatus. Glioma cells can be harvested at 80% confluence, trypsinized, and then washed three times in sterile, isotonic phosphate buffered saline. Cells can be counted in a hemocytometer and diluted to a final concentration of $1 \times 10^5$ cells per µl. 5 µl of glioma cells ($5 \times 10^5$) can be stereotaxically injected into a 0.5 mm pocket made by a 23 gauge needle in the left anterior corpus striatum (−1 mm bregma, +4 mm left lateral, −5.0 mm depth) under sterile conditions in a laminar flow hood.

Animal Preparation. Immediately following stereotaxic tumor implantation, male Wistar rats (250-280 gm) can be fitted with a plastic cannula guide that extends 2 mm below the surface of the skull to instill the drug directly into the subdural space via a borosilicate cannula (Plastics One; Roanoke, Va.). The cannula and guide construction can be non-paramagnetic and permits spectroscopic imaging of the animals before and during drug infusion. Utilizing tumor growth kinetics, animals with intracerebral C6 tumor xenografts of 60-80 mm$^3$ volumes can be selected for infusion with amiloride conjugates of the present invention.

NMR spectroscopy. Prior to imaging, the rats can be administered 0.5 cc of Omniscan gadodiamide intraperitoneally (Nycomed, Princeton, N.J.). The rats can be anesthetized by face mask with a 1.5% isoflurane and 0.5 l/min oxygen, placed prone in a Lucite holder, and secured by thin strips of adhesive tapes. A gradient recalled echo sequence can be obtained which furnishes a single slice in sagittal, coronal, and transverse orientations ("triplot") and which serves as a scout image to ensure proper positioning of the animal. Spectroscopic images can be obtained with a 7 Tesla (300 MHz) Bruker BIOSPEC 70/20 system with a 210 mm horizontal bore equipped with B-GA12 shim coils driven by Bruker Shim Power Supply with a maximum of 2A of current for each shim. S116 birdcage design resonator coil (maximum current, 100 A; maximum voltage, 150V) of 72 mm maximum sample diameter with gradient strength of 200 mT/mm can be used for both. T1 weighted images (TR/TE=500/20 msec) can be obtained using the standard spin echo sequence in the transverse, sagittal, and coronal directions. The 2 mm slice thickness encompasses a 64 mm by 64 mm field on a 128×128 matrix, and renders 25 mm$^2$ per pixel resolution. Multiple contiguous slices separated by 1 mm can be collected using 3 sinc pulses of 2 msec duration, which cover the entire tumor in one scan. The average scan time can be approximately 60 sec for the entire T1 weighted protocol. Diffusion weighted images can be obtained using a spin echo sequence that can be modified to include the diffusion sensitizing gradients and images acquired in the same set of slices as in the T1 weighted sequences. Four sets of diffusion-weighted images can be obtained using the following 'b' values: 11.942, 174.275, 549.771, and 1138.429 sec/mm$^2$. The TR/TE can be set at 3600/60 msec and the total collection time can be 30 min. The gradient separation (big delta) time can be 20 msec and the value of small delta (gradient on time) can be 10 msec. Data can be processed mostly using Paravision (Bruker) on a silicon graphics imaging workstation. Apparent diffusion constant (ADC) maps for all the slices can be calculated with the Paravision software using a two parameter exponential fit (Roberts et al., *Eur. J. Radiol.*, 45:185-194 (2003)).

Cytological Staining. The cytological markers have been well established in several models of brain injury and in glioma xenografts. Confirmatory markers can be used on adjacent brain sections when possible to assess their relative sensitivities. For example, the TUNEL assay is a specific but late marker of apoptosis that has reduced sensitivity in vivo. As a positive control, staurosporine-induced apoptosis in astrocytes and gliomas that is associated with annexin V binding can be examined. Therefore, the sensitivities of annexin V binding with the TUNEL assay in vivo can be compared. Errors in detection sensitivities of these cytological markers are systematic as the indices of apoptosis, necrosis, and proliferation between the treatment and control groups can be compared.

The stains used for cytological staining can include: (1) Nissl stain, which provides a high-contrast image of glioma cells for determination of cell volume; (2) Bromodeoxyuridine (BrdU) labeling, in which rats can be injected intraperitoneally with BrdU (60 mg/kg) 1 h before intracardiac perfusion with 4% paraformaldehyde to label proliferating cells and 4 µm sections can be immunostained with a FITC-labeled, polyclonal antibody against GFAP (1:10,000) followed by a cyan-labeled, polyclonal antibody against BrdU (1:1000) as described (Reilly et al., *Exp. Neurol.*, 140:139-150 (1996)); (3) Hematoxylin and eosin stains, which identify necrotic neurons and astrocytes when used at 200× magnification; (4) FITC-labeled annexin V, which binds to a phosphoserine cell membrane marker that is externalized late in apoptosis and efficiently stains apoptotic cells in paraffin-embedded brain sections; (5) Hoescht 3222 or DAPI stains, which are fluorescent nuclear counter stains that permit morphological assessment of nuclear morphological changes associated with apoptosis or necrosis (oncosis); and (6) H2Ax immunostain, which is performed with a purified mouse monoclonal antibody against a peptide fragment (amino acids 178-194) of human H2Ax. Fluorescent identification of necrotic cells permits semi-automated laser microscope cytometry and the fluorescent nuclear stain Hoescht 3222 or Sytox Green has been used to identify apoptotic and necrotic glioma cells treated with staurosporine or amiloride, respectively. A comparison on alternate slides of the necrotic cells identified with Sytox Green with those identified by hematoxylin and eosin staining can be performed.

Stereological methods. Rats can be deeply anesthetized with sodium pentobarbitol (75 mg/kg, i.p.) followed by intracardiac perfusion with phosphate buffer saline followed by 4% buffered paraformaldehyde. Brains can be removed and postfixed in 2% paraformaldehyde at 4° C. for 24 h and then paraffin embedded or placed into sucrose prior to storage at −80° C. Postfixed brains can be cryoprotected in sucrose and sectioned at 40 µm on a freezing stage microtome. These thicker sections can be stained with a high-contrast Nissl stain and tumor volume of sequential sections can then be calculated by the Cavalieri method. Unbiased stereological techniques can be used to estimate tumor volume and cell density.

Tumor volumes can be calculated by the Cavalieri method. This method estimates the volume of a structure (e.g., glial tumor) by measuring the area of the structure in a number of evenly spaced "two-dimensional" sections. For an in vivo tumor model, the procedure involves a systematically random collection of 10 sections evenly spaced through the entire tumor. To perform this, the brain is cut into 40 µm coronal sections and every section is collected to encompass the entire tumor. When the most anterior portion of the tumor becomes visible in the series of sections, a dye is thrown to determine if the first, second, third, fourth, or fifth section from that point should be the initial section saved for staining and area analysis. Henceforth, every tenth section is stained and the tumor area measured. This ensures that each section through the tumor has an equal probability of being analyzed. Tumor area is estimated with suitable precision by applying to each section a point grid with a known area associated with each point (a/p). Tumor volume (V) is then calculated using the formula: $V=(T) \cdot (a/p) \cdot \Sigma P_i$; where "T"=distance between sections and "P"=points landing on the tumor in section "i". The grid generation and volume calculations can be performed with Stereologer (Version 1.0) software on a Windows-based system connected to a Nikon E600 microscope with motorized xyz stage controller (ASI MS-2000). Tumor volumes can be described as mean volumes $(mm^3) \pm S.D.$ Quantitative Measurements of Cell Counts. Unbiased cell counting can be performed using the optical fractionator stereological method. This method is based on the principle that the number of cells in a whole object (e.g., glioma) can be accurately estimated by counting the number of cells in a known fraction of the object. The volume of the area of interest is first calculated by the Cavalieri method described above. The Stereologer software divides the area of interest on each slide into "dissectors," which are small volumes of tissue (e.g., 25×25×20 µm) from which the cell counts are made. It is only necessary to count approximately 10% of the dissectors to arrive at accurate estimates of the number of cells in the entire object. The software randomly selects the dissectors to be counted.

EF5 perfusion. EF5 can be perfused in deeply anethesized animals pretreated 3 h before with BrdU and then the brains can be immediately frozen. Frozen sections can be immunostained for EF5 binding and analyzed by a sensitive CCD camera. The entire optical system, including the CCD camera, can be calibrated by an absolute fluorescence standard (dye in hemocytometer). The maximum binding rate can be estimated using the tissue cube method by calculating an "average" oxygen dependence of the contralateral normal brain hemisphere. The best-fit approximation for existing data can be an inverse relationship between binding and $pO_2$, with binding decreasing 50-fold between 0.1% and 10% oxygen. Using these methods, an estimate of the minimum $pO_2$ (i.e., maximum binding) in experimental rodent and human tumors can be determined.

Neutral red. Neutral Red can be perfused in animals pretreated 3 h before with BrdU and then the brains can be immediately frozen using the liquid nitrogen funnel technique. Cryostat frozen sections can be visualized and photographed by a CCD camera for semiquantitative photometry (Hoffman et al., id; Chavez et al., *J. Neurosci.*, 22:8922-8831 (2002)). The possibility that deeply anesthetized animals can be perfused with EF5 followed by neutral red prior to sacrifice can be investigated. Neutral red sections can be digitally imaged and subsequently immunostained for EF5 using an anti-EF5 monoclonal antibody.

Assessment of Behavioral Effects

Beam Walk. Components of fine motor coordination can be assessed using a beam-walking task. Twenty-four hours prior to tumor implantation, rats can be trained to escape a bright light and loud white noise by traversing an elevated narrow wooden beam (2.5×100.0 cm) to enter a darkened goal box at the opposite end of the beam. Performance for each day can be the mean latency of three trials to traverse the beam.

Morris water maze. Acquisition of reference memory (e.g., spatial learning/memory) performance can be assessed with a Morris water maze task. The test apparatus consists of a large white circular tank (220 cm diameter by 60 cm high) filled with water to a depth of 21 cm. Water temperature can be maintained at 26±2° C. A transparent circular escape platform (12 cm diameter, 19 cm high) can be placed in fixed position in the tank 2 cm below the water surface. Consistent visual cues can be located in the test room outside of the maze. Each trial can be started by placing the rat in the water close to and facing the wall of the tank in one of the four cardinal start locations. Rats can be allowed 120 sec to find and mount the escape platform. Rats can receive 4 trials/day over 5 consecutive days. Data can be recorded using a video tracking system (Poly-Track, San Diego Instruments). Performance for each day can be the mean latency of four trials to find the platform.

Neurotoxicity Behavioral Signs. A standard behavioral checklist (Chang, in *Neurotoxicology* A.-D. M. B., Ed., CRC Press, pp. 223-252 (1993)) can be performed daily to determine neurotoxic effects that might be missed with the above quantitative behavioral tests. Animals that exhibit one or more of the principal signs as shown in Table 10 for three consecutive days can be terminated from further testing and euthanized.

TABLE 10

Neurotoxicity and Behavioral Signs.

| Principal Endpoint | Signs (any one sign for 2 consecutive days constitutes an endpoint) |
|---|---|
| MOTOR | Activity Changes |
| | Uncoordination |
| | Weakness and paralysis |
| | Abnormal movement and posture |
| | Tremor |
| SENSORY | Primary sensory deficits |
| | Pain |
| | Equilibrium disorders |
| AROUSAL OR REACTIVITY | Increased irritability or reactivity; change in CNS excitability |

Drug measurements in blood, cerebrospinal fluid, and brain tissue. Frozen brain homogenates can be spiked with amiloride and a caffeine standard. Dimethylacetamide extraction can reproducibly recover 70% of the amiloride from brain pulverized in liquid nitrogen and LC-MS can be used to measure the amount of amiloride accumulating in brain tissue during 12 days of intrathecal infusion using an Alzet pump.

Statistical Analyses. Body weight, beam walk, and Morris water maze assessments can be analyzed with repeated measures ANOVA (Treatment Group×Days) with assessment days as the repeated variable within subjects. When ANOVA is significant, post hoc Dunnett's test for comparison of individual treatments to control can be performed.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

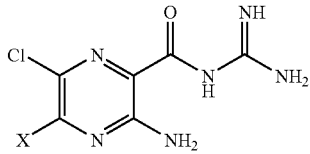

wherein X is an amino acid attached at the N-terminus, selected from the group consisting of glycine, phenylalanine, (2,4-dichloro)-phenylalanine, serine, and O-benzyl serine.

2. The compound of claim 1, wherein X is glycine.

3. A compound having the formula:

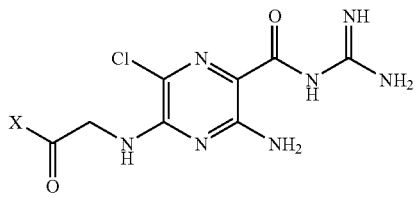

wherein X is a peptide attached at the N-terminus, selected from the group consisting of SEQ ID NOS:2 to 7 and 41.

* * * * *